(12) United States Patent
Søe et al.

(10) Patent No.: US 8,927,036 B2
(45) Date of Patent: *Jan. 6, 2015

(54) ENZYMATIC OIL-DEGUMMING METHOD

(75) Inventors: Jorn Borch Søe, Tilst (DK); Mark Turner, Horshølm (DK)

(73) Assignee: Dupont Nutrition Biosciences APS, Copenhagen (DK)

( * ) Notice: Subject to any disclaimer, the term of this patent is extended or adjusted under 35 U.S.C. 154(b) by 564 days.

This patent is subject to a terminal disclaimer.

(21) Appl. No.: 13/172,679

(22) Filed: Jun. 29, 2011

(65) Prior Publication Data

US 2012/0064192 A1 Mar. 15, 2012

Related U.S. Application Data

(63) Continuation of application No. 11/623,689, filed on Jan. 16, 2007, now Pat. No. 8,192,782, which is a continuation-in-part of application No. PCT/GB2005/002823, filed on Jul. 18, 2005.

(60) Provisional application No. 60/591,185, filed on Jul. 26, 2004.

(30) Foreign Application Priority Data

Jul. 16, 2004 (GB) .................................. 0416035.4
Jul. 7, 2005 (GB) .................................. 0513859.9

(51) Int. Cl.

| | | |
|---|---|---|
| A23L 1/23 | (2006.01) | |
| A23D 7/00 | (2006.01) | |
| C12N 9/00 | (2006.01) | |
| C12N 9/10 | (2006.01) | |
| C12N 15/00 | (2006.01) | |
| C07H 21/04 | (2006.01) | |
| A23J 7/00 | (2006.01) | |
| C12P 7/64 | (2006.01) | |
| A21D 8/04 | (2006.01) | |
| C12N 9/20 | (2006.01) | |
| C11B 3/00 | (2006.01) | |

(52) U.S. Cl.
CPC .................. *C12N 9/1029* (2013.01); *A23J 7/00* (2013.01); *C12P 7/6481* (2013.01); *A21D 8/042* (2013.01); *C12P 7/6445* (2013.01); *C12N 9/20* (2013.01); *C12P 7/6418* (2013.01); *C12Y 301/01003* (2013.01); *C11B 3/003* (2013.01)
USPC ............. 426/33; 426/601; 435/183; 435/193; 435/320.1; 536/23.2

(58) Field of Classification Search
None
See application file for complete search history.

(56) References Cited

U.S. PATENT DOCUMENTS

| | | | |
|---|---|---|---|
| 8,192,782 B2 * | 6/2012 | Soe et al. ....................... | 426/601 |
| 2006/0040357 A1 | 2/2006 | Bandaru et al. | |
| 2008/0070287 A1 | 3/2008 | Soe et al. | |

FOREIGN PATENT DOCUMENTS

| | | |
|---|---|---|
| CA | 2403025 | 8/2004 |
| EP | 1788080 | 5/2007 |
| JP | 11-228986 | 8/1999 |
| WO | WO03006644 | 1/2003 |
| WO | WO03020941 | 3/2003 |
| WO | WO03089620 | 10/2003 |
| WO | WO03100044 | 12/2003 |
| WO | WO2004064537 | 8/2004 |
| WO | WO2005066351 | 7/2005 |
| WO | WO2006008508 | 1/2006 |
| WO | WO2008090395 | 7/2008 |
| WO | WO2008094847 | 8/2008 |
| WO | WO2009002480 | 12/2008 |
| WO | WO2009024736 | 2/2009 |
| WO | WO2009024862 | 2/2009 |
| WO | WO2009081094 | 7/2009 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Banas A. et al., "Cellular sterol ester synthesis in plants is performed by an enzyme . . . ", J. Biol. Chem., 2005, vol. 280, No. 41, p. 34626-34634.
Buckley J. Thomas, "Substrate specificity of bacterial glycerophospholipid", Cholesterol Acyltransferase, Biochemistry 1982, vol. 21, p. 6699-6703.

(Continued)

*Primary Examiner* — Christian Fronda
(74) *Attorney, Agent, or Firm* — Vedder Price P.C.; Thomas J. Kowalski; Deborah L. Lu

(57) ABSTRACT

A process of enzymatic degumming edible oils, comprising treating edible oil with a lipid acyltransferase so as to transfer an acyl group from a major part of the phospholipid to one or more acyl acceptors, wherein the acyl acceptor may be any compound comprising a hydroxyl group. In one embodiment preferably the acyl acceptor is water and in another embodiment preferably the acyl acceptor is one or more sterols and/or stanols. When the acyl acceptor is a stanol and/or sterol, one or more sterol esters and/or stanol esters are produced. The lipid acyltransferase for use in the process of the present invention may comprise one or more of the following amino acid sequences: SEQ ID NO: 1, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, or SEQ ID NO: 15, SEQ ID NO: 16, SEQ ID NO: 17, SEQ ID NO: 18, SEQ ID NO: 36, SEQ ID NO: 38, SEQ ID NO: 40, SEQ ID NO: 41, SEQ ID NO: 45, SEQ ID NO: 47, SEQ ID NO: 50 or an amino acid sequence which has 75% or more identity thereto. A novel lipid acyltransferase comprising the amino acid sequence shown as SEQ ID NO: 16 is also taught.

20 Claims, 37 Drawing Sheets

(56) References Cited

OTHER PUBLICATIONS

Database accession No. P10480 -& Database UniProt 'Online!, Jul. 1, 1989.
Database accession No. Q44268 -& Database UniProt 'Online! Nov. 1, 1996.
Database accession No. Q9F7Y6 Database UniProt 'Online!, Mar. 1, 2001.
EC 2.3.1.43 (downloaded Apr. 21, 2009).
Graille J, Lipid Technology, vol. 5, No. 1, 1993, pp. 11-16.
Hilton S et al, Biochemistry vol. 29, No. 38, 1990, pp. 9072-9078.
Enzyme catalyzed synthesis of structured phospholipids with conjugated linoleic acid and plant sterols, MD. Monjur Hossen, Thesis dissertation, May 2005.
Kalscheuer et al, Synthesis of novel lipids in *Saccharomyces cerivisiae* by heterologous expression of . . . , Applied and Environmental Microbiology, vol. 70, No. 12, p. 7119-7125, 2004.
McIntyre et al., Distribution of glycerophospholipid-cholesterol acyltransferase in selected bacterial species, J. Bacteriol., Jul. 1979, vol. 139, No. p. 132-136.
Peelman F, et al, A proposed architecture for lecithin cholesterol acyl transferase (LCAT): Identification of the catalytic triad and molecular modeling, Protein Science 1998.
Score search results for application 11852274, Glycerophospholipid-cholesterol acyltransferase precursor (run on Jan. 27, 2009).
Thornton et al, Molecular cloning of a phospholipid-cholesterol acyltransferase from *Aeromonas hydrophila*. Sequence homologies. . . , 1988 Biochem. Et Biophys. Acta. 959, 153-159.
van Solingen, Pieter, et al., "The cloning and characterization of the acyltransferase gene of *Penicillium chrysogenum*", Agricultural University, Wageningen, The Netherlands (1989).
Vaysse et al, Fatty hydroxamic acid biosynthesis in aqueous medium in the presence of the lipase-acyltransferase from *Candida parasilosis*, J. of Biotechnology 53 (1997) 41-46.

\* cited by examiner

FIGURE 10

SEQ ID No. 16

```
  1   ADTRPAFSRI  VMFGDSLSDT  GKMYSKMRGY  LPSSPPYYEG  RFSNGPVWLE  QLTKQFPGLT
 61   IANEAEGGAT  AVAYNKISWD  PKYQVINNLD  YEVTQFLQKD  SFKPDDLVIL  WVGANDYLAY
121   GWNTEQDAKR  VRDAISDAAN  RMVLNGAKQI  LLFNLPDLGQ  NPSARSQKVV  EAVSHVSAYH
181   NKLLLNLARQ  LAPTGMVKLF  EIDKQFAEML  RDPQNFGLSD  VENPCYDGGY  VWKPFATRSV
241   STDRQLSAFS  PQERLAIAGN  PLLAQAVASP  MARRSASPLN  CEGKMFWDQV  HPTTVVHAAL
301   SERAATFIET  QYEFLAHG
```

FIGURE 11

(SEQ ID No. 1)

```
  1   MKKWFVCLLG  LVALTVQAAD  SRPAFSRIVM  FGDSLSDTGK  MYSKMRGYLP
 51   SSPPYYEGRF  SNGPVWLEQL  TKQFPGLTIA  NEAEGGATAV  AYNKISWNPK
101   YQVINNLDYE  VTQFLQKDSF  KPDDLVILWV  GANDYLAYGW  NTEQDAKRVR
151   DAISDAANRM  VLNGAKQILL  FNLPDLGQNP  SARSQKVVEA  VSHVSAYHNQ
201   LLLNLARQLA  PTGMVKLFEI  DKQFAEMLRD  PQNFGLSDVE  NPCYDGGYVW
251   KPFATRSVST  DRQLSAFSPQ  ERLAIAGNPL  LAQAVASPMA  RRSASPLNCE
301   GKMFWDQVHP  TTVVHAALSE  RAATFIANQY  EFLAH*
```

FIGURE 12

(SEQ ID No. 2)

```
  1   ivafGDSlTd  geayygdsdg  ggWgagladr  Ltallrlrar  prgvdvfnrg  isGrtsdGrl
 61   ivDalvallF  laqslglpnL  pPYLsgdflr  GANFAsagAt  Ilptsgpfli  QvqFkdfksq
121   vlelrqalgl  lqellrllpv  ldakspdlvt  imiGtNDlit  saffgpkste  sdrnvsvpef
181   kdnlrqlikr  Lrsnngarii  vlitlvilnl  gplGClPlkl  alalassknv  dasgclerln
241   eavadfneal  relaiskled  qlrkdglpdv  kgadvpyvDl  ysifqdldgi  qnpsayvyGF
301   ettkaCCGyG  gryNynrvCG  naglcnvtak  aCnpssylls  flfwDgfHps  ekGykavAea
361   l
```

FIGURE 13

(SEQ ID No. 3)

```
  1   mkkwfvcllg  lvaltvqaad  srpafsrivm  fgdslsdtgk  myskmrgylp  ssppyyegrf
 61   sngpvwleql  tnefpgltia  neaeggptav  aynkiswnpk  yqvinnldye  vtqflqkdsf
121   kpddlvilwv  gandylaygw  nteqdakrvr  daisdaanrm  vlngakeill  fnlpdlgqnp
181   sarsqkvvea  ashvsayhnq  lllnlarqla  ptgmvklfei  dkqfaemlrd  pqnfglsdqr
241   nacyggsyvw  kpfasrsast  dsqlsafnpq  erlaiagnpl  laqavaspma  arsastlnce
301   gkmfwdqvhp  ttvvhaalse  paatfiesqy  eflah
```

FIGURE 14

SEQ ID No. 4

```
  1 mkkwfvcllg lialtvqaad trpafsrivm fgdslsdtgk myskmrgylp ssppyyegrf
 61 sngpvwleql tkqfpgltia neaeggatav aynkiswnpk yqvynnldye vtqflqkdsf
121 kpddlvilwv gandylaygw nteqdakrvr daisdaanrm vlngakqill fnlpdlgqnp
181 sarsqkvvea vshvsayhnk lllnlarqla ptgmvklfei dkqfaemlrd pqnfglsdve
241 npcydggyvw kpfatrsvst drqlsafspq erlaiagnpl laqavaspma rrsasplnce
301 gkmfwdqvhp ttvvhaalse raatfietqy eflahg
```

FIGURE 15

SEQ ID No. 5

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 16

SEQ ID No. 6

```
  1 mpkpalrrvm tatvaavgtl algltdatah aapaqatptl dyvalgdsys agsgvlpvdp
 61 anllclrsta nyphviadtt garltdvtcg aaqtadftra qypgvapqld algtgtdlvt
121 ltiggndnst finaitacgt agvlsggkgs pckdrhgtsf ddeieantyp alkeallgvr
181 arapharvaa lgypwitpat adpscflklp laagdvpylr aiqahlndav rraaeetgat
241 yvdfsgvsdg hdaceapgtr wiepllfghs lvpvhpnalg errmaehtmd vlgld
```

FIGURE 17

SEQ ID No. 7

```
  1 mdyekfllfg dsitefafnt rpiedgkdqy algaalvney trkmdilqrg fkgytsrwal
 61 kilpeilkhe snivmatifl gandacsagp qsvplpefid nirqmvslmk syhirpiiig
121 pglvdrekwe kekseeialg yfrtnenfai ysdalaklan eekvpfvaln kafqqeggda
181 wqqlltdglh fsgkgykifh dellkvietf ypqyhpknmq yklkdwrdvl ddgsnims
```

FIGURE 18

(SEQ ID No. 8)

```
              10         20         30         40         50         60
              |          |          |          |          |          |
       MNLRQWMGAA TAALALGLAA CGGGGTDQSG NPNVAKVQRM VVFGDSLSDI GTYTPVAQAV 70         80         90        100        110        120
              |          |          |          |          |          |
       GGGKFTTNPG PIWAETVAAQ LGVTLTPAVM GYATSVQNCP KAGCFDYAQG GSRVTDPNGI 130        140        150        160        170        180
              |          |          |          |          |          |
       GHNGGAGALT YPVQQQLANF YAASNNTFNG NNDVVFVLAG SNDIFFWTTA AATSGSGVTP 190        200        210        220        230        240
              |          |          |          |          |          |
       AIATAQVQQA ATDLVGYVKD MIAKGATQVY VFNLPDSSLT PDGVASGTTG QALLHALVGT 250        260        270        280        290        300
              |          |          |          |          |          |
       FNTTLQSGLA GTSARIIDFN AQLTAAIQNG ASFGFANTSA RACDATKINA LVPSAGGSSL 310        320        330        340
              |          |          |          |
       FCSANTLVAS GADQSYLFAD GVHPTTAGHR LIASNVLARL LADNVAH
```

FIGURE 19 (SEQ ID No. 9)

```
  1 migsyvavgd sftegvgdpg pdgafvgwad rlavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldlwslrs vqdrrawdad rlhlspeght
181 rvalragqal glrvpadpdq pwpplpprgt ldvrrddvhw areylvpwig rrlrgessgd
241 hvtakgtlsp daiktriaav a
```

FIGURE 20

(SEQ ID No. 10)

```
  1 mqtnpaytsl vavgdsfteg msdllpdgsy rgwadllatr maarspgfry anlavrgkli
 61 gqivdeqvdv aaamgadvit lvgglndtlr pkcdmarvrd lltqaverla phceqlvlmr
121 spgrqgpvle rfrprmealf aviddlagrh gavvvdlyga qsladprmwd vdrlhltaeg
181 hrrvaeavwq slghepedpe whapipatpp pgwvtrrtad vrfarqhllp wigrrltgrs
241 sgdglpakrp dllpyedpar
```

FIGURE 21

(SEQ ID No. 11)

```
  1 mtrgrdggag apptkhrall aaivtlivai saaiyagasa ddgsrdhalq aggrlprgda
 61 apastgawvg awatapaaae pgtettglag rsvmvvhts vggtgaritl snlygqsplt
121 vthasialaa gpdtaaaiad tmrrltfggs arviipaggq vmsdtarlai pyganvlvtt
181 yspipsgpvt yhpqarqtsy ladgdrtadv tavayttptp ywryltaldv lsheadgtvv
241 afgdsitdga rsqsdanhrw tdvlaarlhe aagdgrdtpr ysvvnegisg nrlltsrpgr
301 padnpsglsr fqrdvlertn vkavvvvlgv ndvlnspela drdailtglr tlvdraharg
361 lrvvgatitp fggyggytea retmrqevne eirsgrvfdt vvdfdkalrd pydprrmrsd
421 ydsgdhlhpg dkgyarmgav idlaalkgaa pvka
```

FIGURE 22 (SEQ ID No. 12)

```
  1 mtsmsrarva rriaagaayg gggiglagaa avglvvaevq larrrvgvgt ptrvpnaqgl
 61 yggtlptagd pplrlmmlgd staagqgvhr agqtpgalla sglaavaerp vrlgsvaqpg
121 acsddldrqv alvlaepdrv pdlcvlmvga ndvthrmpat rsvrhlssav rrlrtagaev
181 vvgtcpdlgt iervrqplrw larrasrqla aaqtigaveq ggrtvslgdl lgpefaqnpr
241 elfgpdnyhp saegyataam avlpsvcaal glwpadeehp dalrregflp varaaaeaas
301 eagtevaaam ptgprgpwal lkrrrrrrvs eaepsspsgv
```

FIGURE 23 (SEQ ID No. 13)

```
  1 mgrgtdqrtr ygrrrarval aaltaavlgv gvagcdsvgg dspapsgsps krtrtapawd
 61 tspasvaavg dsitrgfdac avlsdcpevs watgssakvd slavrllgka daaehswnya
121 vtgarmadlt aqvtraaqre pelvavmaga ndacrsttsa mtpvadfraq feeamatllrk
181 klpkaqvyvs sipdlkrlws qgrtnplgkq vwklglcpsm lgdadsldsa atlrrntvrd
241 rvadynevlr evcakdrrcr sddgavhefr fgtdqlshwd wfhpsvdgqa rlaeiayrav
301 taknp
```

FIGURE 24 (SEQ ID No. 14)

```
  1 mrlsrraata sallltpala lfgasaavsa prlqatdyva lgdsyssgvg agsydsssgs
 61 ckrstksypa lwaashtgtr fnftacsgar tgdvlakqlt pvnsgtdlvs itiggndagf
121 adtmttcnlq gesaclaria karayiqqtl paqldqvyda idsrapaaqv vvlgyprfyk
181 lggscavgls eksraainaa addinavtak raadhgfafg dvnttfaghe lcsgapwlhs
241 vtlpvensyh ptangqskgy lpvlnsat
```

FIGURE 25 (SEQ ID No. 15)

```
  1  MKKWFVCLLG  LIALTVQAAD  TRPAFSRIVM  FGDSLSDTGK  MYSKMRGYLP
 51  SSPPYYEGRF  SNGPVWLEQL  TKQFPGLTIA  NEAEGGATAV  AYNKISWNPK
101  YQVINNLDYE  VTQFLQKDSF  KPDDLVILWV  GANDYLAYGW  NTEQDAKRVR
151  DAISDAANRM  VLNGAKQILL  FNLPDLGQNP  SARSQKVVEA  VSHVSAYHNK
201  LLLNLARQLA  PTGMVKLFEI  DKQFAEMLRD  PQNFGLSDVE  NPCYDGGYVW
251  KPFATRSVST  DRQLSAFSPQ  ERLAIAGNPL  LAQAVASPMA  RRSASPLNCE
301  GKMFWDQVHP  TTVVHAALSE  RAATFIETQY  EFLAHG*
```

Figure 2B (SEQ ID NO. 17)

```
Met Arg Tyr Phe Ala Ile Ala Phe Leu Leu Ile Asn Thr Ile Ser Ala
 1               5                  10                  15
Phe Val Leu Ala Pro Lys Lys Pro Ser Gln Asp Asp Phe Tyr Thr Pro
             20                  25                  30
Pro Gln Gly Tyr Glu Ala Gln Pro Leu Gly Ser Ile Leu Lys Thr Arg
         35                  40                  45
Asn Val Pro Asn Pro Leu Thr Asn Val Phe Thr Pro Val Lys Val Gln
     50                  55                  60
Asn Ala Trp Gln Leu Leu Val Arg Ser Glu Asp Thr Phe Gly Asn Pro
 65                  70                  75                  80
Asn Ala Ile Val Thr Thr Ile Ile Gln Pro Phe Asn Ala Lys Lys Asp
                 85                  90                  95
Lys Leu Val Ser Tyr Gln Thr Phe Glu Asp Ser Gly Lys Leu Asp Cys
             100                 105                 110
Ala Pro Ser Tyr Ala Ile Gln Tyr Gly Ser Asp Ile Ser Thr Leu Thr
         115                 120                 125
Thr Gln Gly Glu Met Tyr Tyr Ile Ser Ala Leu Leu Asp Gln Gly Tyr
     130                 135                 140
Tyr Val Val Thr Pro Asp Tyr Glu Gly Pro Lys Ser Thr Phe Thr Val
145                 150                 155                 160
Gly Leu Gln Ser Gly Arg Ala Thr Leu Asn Ser Leu Arg Ala Thr Leu
                 165                 170                 175
Lys Ser Gly Asn Leu Thr Gly Val Ser Ser Asp Ala Glu Thr Leu Leu
             180                 185                 190
Trp Gly Tyr Ser Gly Gly Ser Leu Ala Ser Gly Trp Ala Ala Ala Ile
         195                 200                 205
Gln Lys Glu Tyr Ala Pro Glu Leu Ser Lys Asn Leu Leu Gly Ala Ala
     210                 215                 220
Leu Gly Gly Phe Val Thr Asn Ile Thr Ala Thr Ala Glu Ala Val Asp
225                 230                 235                 240
Ser Gly Pro Phe Ala Gly Ile Ile Ser Asn Ala Leu Ala Gly Ile Gly
                 245                 250                 255
Asn Glu Tyr Pro Asp Phe Lys Asn Tyr Leu Leu Lys Lys Val Ser Pro
             260                 265                 270
Leu Leu Ser Ile Thr Tyr Arg Leu Gly Asn Thr His Cys Leu Leu Asp
         275                 280                 285
Gly Gly Ile Ala Tyr Phe Gly Lys Ser Phe Phe Ser Arg Ile Ile Arg
     290                 295                 300
Tyr Phe Pro Asp Gly Trp Asp Leu Val Asn Gln Glu Pro Ile Lys Thr
305                 310                 315                 320
Ile Leu Gln Asp Asn Gly Leu Val Tyr Gln Pro Lys Asp Leu Thr Pro
                 325                 330                 335
Gln Ile Pro Leu Phe Ile Tyr His Gly Thr Leu Asp Ala Ile Val Pro
             340                 345                 350

Ile Val Asn Ser Arg Lys Thr Phe Gln Gln Trp Cys Asp Trp Gly Leu
             355                 360                 365
Lys Ser Gly Glu Tyr Asn Glu Asp Leu Thr Asn Gly His Ile Thr Glu
    370                 375                 380
Ser Ile Val Gly Ala Pro Ala Ala Leu Thr Trp Ile Ile Asn Arg Phe
385                 390                 395                 400
Asn Gly Gln Pro Pro Val Asp Gly Cys Gln His Asn Val Arg Ala Ser
                405                 410                 415
Asn Leu Glu Tyr Pro Gly Thr Pro Gln Ser Ile Lys Asn Tyr Phe Glu
            420                 425                 430
Ala Ala Leu His Ala Ile Leu Gly Phe Asp Leu Gly Pro Asp Val Lys
        435                 440                 445
Arg Asp Lys Val Thr Leu Gly Gly Leu Leu Lys Leu Glu Arg Phe Ala
    450                 455                 460
Phe
465
```

Figure 29 (SEQ No. 18)

```
Met Arg Tyr Phe Ala Ile Ala Phe Leu Leu Ile Asn Thr Ile Ser Ala
 1               5                  10                  15
Phe Val Leu Ala Pro Lys Lys Pro Ser Gln Asp Asp Phe Tyr Thr Pro
            20                  25                  30
Pro Gln Gly Tyr Glu Ala Gln Pro Leu Gly Ser Ile Leu Lys Thr Arg
        35                  40                  45
Asn Val Pro Asn Pro Leu Thr Asn Val Phe Thr Pro Val Lys Val Gln
    50                  55                  60
Asn Ala Trp Gln Leu Leu Val Arg Ser Glu Asp Thr Phe Gly Asn Pro
 65              70                  75                  80
Asn Ala Ile Val Thr Thr Ile Ile Gln Pro Phe Asn Ala Lys Lys Asp
                85                  90                  95
Lys Leu Val Ser Tyr Gln Thr Phe Glu Asp Ser Gly Lys Leu Asp Cys
            100                 105                 110
Ala Pro Ser Tyr Ala Ile Gln Tyr Gly Ser Asp Ile Ser Thr Leu Thr
        115                 120                 125
Thr Gln Gly Glu Met Tyr Tyr Ile Ser Ala Leu Leu Asp Gln Gly Tyr
    130                 135                 140
Tyr Val Val Thr Pro Asp Tyr Glu Gly Pro Lys Ser Thr Phe Thr Val
145                 150                 155                 160
Gly Leu Gln Ser Gly Arg Ala Thr Leu Asn Ser Leu Arg Ala Thr Leu
                165                 170                 175
Lys Ser Gly Asn Leu Thr Gly Val Ser Ser Asp Ala Glu Thr Leu Leu
            180                 185                 190
Trp Gly Tyr Ser Gly Gly Ser Leu Ala Ser Gly Trp Ala Ala Ala Ile
        195                 200                 205
Gln Lys Glu Tyr Ala Pro Glu Leu Ser Lys Asn Leu Leu Gly Ala Ala
    210                 215                 220
Leu Gly Gly Phe Val Thr Asn Ile Thr Ala Thr Ala Glu Ala Val Asp
225                 230                 235                 240
Ser Gly Pro Phe Ala Gly Ile Ile Ser Asn Ala Leu Ala Gly Ile Gly
                245                 250                 255
Asn Glu Tyr Pro Asp Phe Lys Asn Tyr Leu Leu Lys Lys Val Ser Pro
            260                 265                 270
Leu Leu Ser Ile Thr Tyr Arg Leu Gly Asn Thr His Cys Leu Leu Asp
        275                 280                 285
Gly Gly Ile Ala Tyr Phe Gly Lys Ser Phe Phe Ser Arg Ile Ile Arg
    290                 295                 300
Tyr Phe Pro Asp Gly Trp Asp Leu Val Asn Gln Glu Pro Ile Lys Thr
305                 310                 315                 320
Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350
Ile Val Asn Ser Arg Lys Thr Phe Gln Gln Trp Cys Asp Trp Gly Leu
        355                 360                 365
Lys Ser Gly Glu Tyr Asn Glu Asp Leu Thr Asn Gly His Ile Thr Glu
    370                 375                 380
Ser Ile Val Gly Ala Pro Ala Ala Leu Thr Trp Ile Ile Asn Arg Phe
385                 390                 395                 400
Asn Gly Gln Pro Pro Val Asp Gly Cys Gln His Asn Val Arg Ala Ser
                405                 410                 415
Asn Leu Glu Tyr Pro Gly Thr Pro Gln Ser Ile Lys Asn Tyr Phe Glu
            420                 425                 430
Ala Ala Leu His Ala Ile Leu Gly Phe Asp Leu Gly Pro Asp Val Lys
        435                 440                 445
Arg Asp Lys Val Thr Leu Gly Gly Leu Leu Lys Leu Glu Arg Phe Ala
    450                 455                 460
Phe His His His His His
465                 470
```

Figure 30

```
1DEO    T T V Y   L   A G D S T M A K n - - - - - - - - - - - - - - - - - - - - - - - - - - - G G G S G T N G W G E Y L
        s1s1S1S1 s1  s1s1h?h?h?h?                                                                 h1h1h1h1h1h1
1IVN    A D T L L   I   L G D S L S A G - - - - - - - - - - - - - - - - - - - - - - - - - - - Y R M S A S A A W P A L L
        s1s1S1s1 s1  s1s1h h h h                                                                  h1h1h1h1h1h1
P10480  I V         M   F G D S L S D T g k m y s k m r g y l p s s p p y y e G R F S N G P V W L E Q L

1DEO    A S Y L S   A   T V - - - - - - - - - - - - - - - - - - - - V N D   A V A G R S - - A R S Y T R B G R F E N I A D V V
        h1h1h1   s2 s2  s2                                           s2 s2   h3                h3h3h3h3h3h3h3h3h3h3h3h3
1IVN    N D K W q s K - - - - - - - - - - - - - - - - - - - - - - - t s V   S I S G D T - - - S Q Q G L A R L P A L L K Q
        h1h1h1   s2?s2?                                              s2 s2
P10480  T N E F P G   L T i a n e a e g g p t a v a y   I S W N P K Y q v I N N L D Y E V T Q F L Q K D S F
                                           s2?s2s2s2s2 s2     h3h3h3h3h3h3h3h3h3h3h3h3h3h3h3h3

1DEO    T A G D Y   V   I V E F G H N D G g - - - - - - - - - - t d c s g g t g   a E V C Y S V Y D G V N E T I L T F P
        s4s4        s4  s4s4s4s4            g ?  ?        ? ?   s? s?s?s?s?s?s?s?s?h4h4h4
1IVN    H Q P R W   V   L V E L G G N D G - - - - - - - - - - n ?   g ?             - - - L R G F Q P Q Q T E
        h3          s4s4s4s4                                                                     h4h4h4h4h4
P10480  K P D D L   V   I L W V G A N D Y - - - - - - - - - - - - - - - - - - - - L A Y G W N T E Q D A K R V R

1DEO    A Y L E N   A   A K L F T - A K G A K - - - - - - - V I   L S S Q T P - - - - - N N P W E T G T F V N S P T R
        h4h4h4h4h4  h4  h4h4h4h4       h4        s5        s5 s5  s5 s5
1IVN    Q T L R Q   I   L Q D V K A A N A E P   l i m q i R L P A N Y G R - - - - - - - - - - - - - - - - - R Y
        h4h4h4h4h4  h4  h4h4h4h4       s5s5s5   s5s5s5s5?s5?s5?                                             h5
P10480  D A I S D   A   A N R M V - L N G A K - - - - - - - E I L L F N L P d - - - l g q n P S A R S Q K V V E A A S H V

1DEO    F V E Y A   E   L A A E V A - - - - - - - - - - - - - - - G V E Y V   D H W S Y V V D S I Y E T L G N A t v n
        h5h5h5h5h5  h5  h5h5h5h5h5h5h5                               s6s6s6s6?h6h6h6h6h6h6h6h6h6h6     h h h -
1IVN    N E A F S   A   I Y P K K L A k e - - - - - - - - - - - - f D V P L L   P F F M E E V Y L K P Q W - - - -
        h5h5h5h5h5  h5  h5h5h5h5h5h5h5h5                                        s
P10480  Q L L L N L A r g l a p t g m v k - - - - - - l f   e i D K Q F A   E M L R D P P Q N F G L S D Q R N a c y

1DEO    - - - - - - - - - - - - - - - - - - - - - - - - - - - - - - - - - - - - - - - - - - - - - - - -
1IVN    - - - - - - - - - - - - - - - - - - - - - - - - - - - - - - - - - - - - - - - - - - - - - - - -
P10480  g g s Y v - - w k p f a s r s a a s t d s q l s a f n p g e r l a i a g n p l l a g q a v a s p m a a r s a

1DEO    - - - s Y F P I D H T H T S   P A G A   E V V   A B A F L K A   V V C T G T S L K S V L T T T S F E G
        - -  h        s?s?s?    h7h7h7h7       h7  h7   h7h7h7h7h7h7h7 h7h7h7h7h7    h?h?h?
1IVN    - - - - M Q D D G I H P N   R D A Q   P P H I   A D W M A A K Q   L Q P L V N   H D S L E
                s           s s     s s       h7h7h7h7
P10480  g k M F W D Q V H F T T V V H A A L   S E P A A T F   I E S Q Y E F L A H -
```

FIGURE 31
    (SEQ ID No. 19)

```
  1 migsyvavgd sftegvgdpg pdgafvgwad riavlladrr pegdftytnl avrgrlldqi
 61 vaeqvprvvg lapdlvsfaa ggndiirpgt dpdevaerfe lavaaltaaa gtvlvttgfd
121 trgvpvlkhl rgkiatyngh vraiadrygc pvldiwslrs vqdrrawdad rihispeght
181 rvalragqal glrvpadpdq pwpplpprgt ldvrrddvhw areylvpwig rrlrgessgd
241 hvtakgtlsp daiktriaav a
```

Figure 32

(SEQ ID No. 25)

```
  1 MFKFKKNFLV GLSAALMSIS LFSATASAAS ADSRPAFSRI VMFGDSLSDT
 51 GKMYSKMRGY LPSSPPYYEG RFSNGPVWLE QLTKQFPGLT IANEAEGGAT
101 AVAYNKISWN PKYQVINNLD YEVTQFLQKD SFKPDDLVIL WVGANDYLAY
151 GWNTEQDAKR VRDAISDAAN RMVLNGAKQI LLFNLPDLGQ NPSARSQKVV
201 EAVSHVSAYH NQLLLNLARQ LAPTGMVKLF EIDKQFAEML RDPQNFGLSD
251 VENPCYDGGY VWKPFATRSV STDRQLSAFS PQERLAIAGN PLLAQAVASP
301 MARRSASPLN CEGKMFWDQV HPTTVVHAAL SERAATFIAN QYEFLAH**
```

FIGURE 33

(SEQ ID NO. 26)

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

Figure 34

SEQ ID No. 27

ZP_00058717
    1 mlphpagerg evgaffallv gtpqdrrlrl echetrplrg rcgcgerrvp pltlpgdgvl
   61 cttsstrdae tvwrkhlqpr pdggfrphlg vgcllagqgs pgvlwcgreg crfevcrrdt
  121 pglsrtrngd ssppfragws lppkcgeisq sarktpavpr ysllrtdrpd gprgrfvgsg
  181 praatrrrlf lgipalvlvt altlvlavpt gretlwrmwc eatqdwclgv pvdsrgqpae
  241 dgeflllspv qaatwgnyya lgdsyssgdg ardyypgtav kggcwrsana ypelvaeayd
  301 faghlsflac sgqrgyamld aidevgsqld wnsphtslvt igiggndlgf stvlktcmvr
  361 vplldskact dqedairkrm akfettfeel isevrtrapd arilvvgypr ifpeeptgay
  421 ytltasnqrw lnetiqefnq qlaeavavhd eeiaasggvg svefvdvyha ldgheigsde
  481 pwvngvqlrd latgvtvdrs tfhpnaaghr avgervieqi etgpgrplya tfavvagatv
  541 dtlagevg

FIGURE 35

(SEQ ID No. 28)

1 mgsgpraatr rrlflgipal vlvtaltlvl avptgretlw rmwceatqdw clgvpvdsrg
   61 qpaedgefll lspvqaatwg nyyalgdsys sgdgardyyp gtavkggcwr sanaypelva
  121 eaydfaghls flacsgqrgy amldaidevg sqldwnspht slvtigiggn dlgfstvlkt
  181 cmvrvpllds kactdqedai rkrmakfett feelisevrt rapdarilvv gyprifpeep
  241 tgayytltas nqrwlnetiq efnqqlaeav avhdeeiaas ggvgsvefvd vyhaldghci
  301 gsdepwvngv qlrdlatgvt vdrstfhpna aghravgerv ieqietgpgr plyatfavva
  361 gatvdtlage vg

FIGURE 36

(SEQ ID No. 29)

1 mrttviaasa llllagcadg areetagapp gessggiree gaeastsitd vyialgdsya
   61 amggrdqplr gepfclrssg nypellhaev tdltcqgavt gdlleprtlg ertlpaqvda
  121 ltedttlvtl siggndlgfg evagcireri agenaddcvd llgetigeql dqlppqldrv
  181 heairdragd aqvvvtgylp lvsagdcpel gdvseadrrw aveltgqine tvreaaerhd
  241 alfvlpddad ehtscappqq rwadiqgqqt dayplhptsa gheamaaavr dalglepvqp

FIGURE 37

(SEQ ID No. 30)

ZP_00094165

1 mgqvklfarr capvllalag lapaatvare aplaegaryv algssfaagp gvgpnapgsp
     61 ercgrgtlny phllaealkl dlvdatcsga tthhvlgpwn evppqidsvn gdtrlvtlti
    121 ggndvsfvgn ifaaacekma spdprcgkwr eiteeewqad eermrsivrq iharaplarv
    181 vvvdyitvlp psgtcaamai spdrlaqsrs aakrlarita rvareegasl lkfshisrrh
    241 hpcsakpwsn glsapaddgi pvhpnrlgha eaaaalvklv klmk //

FIGURE 38

SEQ ID No. 31

NP_625998.

1 mrrfrlvgfl sslvlaagaa ltgaataqaa qpaaadgyva lgdsyssgvg agsyisssgd
     61 ckrstkahpy lwaaahspst fdftacsgar tgdvlsgqlg plssgtglvs isiggndagf
    121 adtmttcvlq sessclsria taeayvdstl pgkldgvysa isdkapnahv vvigyprfyk
    181 lgttciglse tkrtainkas dhlntvlaqr aaahgftfgd vrttftghel csgspwlhsv
    241 nwlnigesyh ptaagqsggy lpvlngaa
//

FIGURE 39

SEQ ID No. 32

NP_827753.
      1 mrrsritayv tslllavgca ltgaataqas paaaatgyva lgdsyssgvg agsylsssgd
     61 ckrsskaypy lwqaahspss fsfmacsgar tgdvlanqlg tlnsstglvs ltiggndagf
    121 sdvmttcvlq sdsaclsrin takayvdstl pgqldsvyta istkapsahv avlgyprfyk
    181 lggsclagls etkrsainda adylnsaiak raadhgftfg dvkstftghe icssstwlhs
    241 ldllnigqsy hptaagqsgg ylpvmnsva
//

FIGURE 40

SEQ ID No. 33

MRLTRSLSAASVTVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

(SEQ ID No. 34)

ADSRPAFSRIVMFGDSLSDTGKMYSKMRGYLPSSPPYYEGRFSNGPVWLEQLTNEFPG
    LTIANEAEGGPTAVAYNKISWNPKYQVINNLDYEVTQFLQKDSFKPDDLVILWVGANDYL
    AYGWNTEQDAKRVRDAISDAANRMVLNGAKEILLFNLPDLGQNPSARSQKVVEAASHV
    SAYHNQLLLNLARQLAPTGMVKLFEIDKQFAEMLRDPQNFGLSDQRNACYGGSYVWKP
    FASRSASTDSQLSAFNPQERLAIAGNPLLAQAVASPMAARSASTLNCE
    GKMFWDQVHPTTVVHAALSEPAATFIESQYEFLAH

FIGURE 45

(SEQ ID No. 35)

1 ADTRPAFSRI VMFGDSLSDT GKMYSKMRGY LPSSPPYYEG RFSNGPVWLE QLTKQFPGLT
     61 IANEAEGGAT AVAYNKISWN PKYQVINNLD YEVTQFLQKD SFKPDDLVIL WVGANDYLAY
    121 GWNTEQDAKR VRDAISDAAN RMVLNGAKQI LLFNLPDLGQ NPSARSQKVV EAVSHVSAYH
    181 NKLLLNLARQ LAPTGMVKLF EIDKQFAEML RDPQNFGLSD VENPCYDGGY VWKPFATRSV
    241 STDRQLSAFS PQERLAIAGN PLLAQAVASP MARRSASPLN CEGKMFWDQV HPTTVVHAAL
    301 SERAATFIET QYEFLAHG

FIGURE 46

(SEQ ID No. 36)

ACAGGCCGATGCACGGAACCGTACCTTTCCGCAGTGAAGCGCTCTCCCCCATCGTTCGC
CGGGACTTCATCCGCGATTTTGGCATGAACACTTCCTTCAACGCGCGTAGCTTGCTACAA
GTGCGGCAGCAGACCCGCTCGTTGGAGGCTCAGTGAGATTGACCCGATCCCTGTCGGCCG
CATCCGTCATCGTCTTCGCCCTGCTGCTCGCGCTGCTGGGCATCAGCCCGGCCCAGGCAG
CCGGCCCGGCCTATGTGGCCCTGGGGGATTCCTATTCCTCGGGCAACGGCGCCGGAAGTT
ACATCGATTCGAGCGGTGACTGTCACCGCAGCAACAACGCGTACCCCGCCCGCTGGGCGG
CGGCCAACGCACCGTCCTCCTTCACCTTCGCGGCCTGCTCGGGAGCGGTGACCACGGATG
TGATCAACAATCAGCTGGGCGCCCTCAACGCGTCCACCGGCCTGGTGAGCATCACCATCG
GCGGCAATGACGCGGGCTTCGCGGACGCGATGACCACCTGCGTCACCAGCTCGGACAGCA
CCTGCCTCAACCGGCTGGCCACCGCCACCAACTACATCAACACCACCCTGCTCGCCCGGC
TCGACGCGGTCTACAGCCAGATCAAGGCCCGTGCCCCCAACGCCCGCGTGGTCGTCCTCG
GCTACCCGCGCATGTACCTGGCCTCGAACCCCTGGTACTGCCTGGGCCTGAGCAACACCA
AGCGCGCGGCCATCAACACCACCGCCGACACCCTCAACTCGGTGATCTCCTCCCGGGCCA
CCGCCCACGGATTCCGATTCGGCGATGTCCGCCCGACCTTCAACAACCACGAACTGTTCT
TCGGCAACGACTGGCTGCACTCACTCACCCTGCCGGTGTGGGAGTCGTACCACCCCACCA
GCACGGGCCATCAGAGCGGCTATCTGCCGGTCCTCAACGCCAACAGCTCGACCTGATCAA
CGCACGGCCGTGCCCGCCCCGCGCGTCACGCTCGGCGCGGGCGCCGCAGCGCGTTGATCA
GCCCACAGTGCCGGTGACGGTCCCACCGTCACGGTCGAGGGTGTACGTCACGGTGGCGCC
GCTCCAGAAGTGGAACGTCAGCAGGACCGTGGAGCCGTCCCTGACCTCGTCGAAGAACTC
CGGGGTCAGCGTGATCACCCCTCCCCGTAGCCGGGGGCGAAGGCGGCGCCGAACTCCTT
GTAGGACGTCCAGTCGTGCGGCCCGGCGTTGCCACCGTCCGCGTAGACCGCTTCCATGGT
CGCCAGCCGGTCCCCGCGGAACTCGGTGGGGATGTCCGTGCCCAAGGTGGTCCCGGTGGT
GTCCGAGAGCACCGGGGGCTCGTACCGGATGATGTGCAGATCCAAAGAATT

FIGURE 47

(SEQ ID NO. 37):

MRLTRSLSAASVIVFALLLALLGISPAQAAGPAYVALGDSYSSGNGAGSYIDSSGDCHRSN
NAYPARWAAANAPSSFTFAACSGAVTTDVINNQLGALNASTGLVSITIGGNDAGFADAMTT
CVTSSDSTCLNRLATATNYINTTLLARLDAVYSQIKARAPNARVVVLGYPRMYLASNPWYC
LGLSNTKRAAINTTADTLNSVISSRATAHGFRFGDVRPTFNNHELFFGNDWLHSLTLPVWE
SYHPTSTGHQSGYLPVLNANSST

FIGURE 48

SEQ ID No. 38

```
  1 mlphpagerg evgaffallv gtpqdrrlrl echetrplrg rcgcgerrvp pltlpgdgvl
 61 cttsstrdae tvwrkhlqpr pdggfrphlg vgcllagqgs pgvlwcgreg crfevcrrdt
121 pglsrtrngd ssppfragws lppkcgeisq sarktpavpr ysllrtdrpd gprgrfvgsg
181 praatrrrlf lgipalvlvt altlvlavpt gretlwrmwc eatqdwclgv pvdsrgqpae
241 dgeflllspv qaatwgnyya lgdsyssgdg ardyypgtav kggcwrsana ypelvaeayd
301 faghlsflac sgqrgyamld aidevgsqld wnsphtslvt igiggndlgf stvlktcmvr
361 vplldskact dqedairkrm akfettfeel isevrtrapd arilvvgypr ifpeeptgay
421 ytltasnqrw lnetiqefnq qlaeavavhd eeiaasggvg svefvdvyha ldgheigsde
481 pwvngvqlrd latgvtvdrs tfhpnaaghr avgervieqi etgpgrplya tfavvagatv
541 dtlagevg
```

FIGURE 49

(SEQ ID No. 39)

```
   1 ggtggtgaac cagaacaccc ggtcgtcggc gtgggcgtcc aggtgcaggt gcaggttctt
  61 caactgctcc agcaggatgc cgccgtggcc gtgcacgatg gccttgggca ggcctgtggt
 121 ccccgacgag tacagcaccc atagcggatg gtcgaacggc agcggggtga actccagttc
 181 cgcgccttcg cccgcggctt cgaactccgc ccaggacagg gtgtcggcga cagggccgca
 241 gcccaggtac ggcaggacga cggtgtgctg caggctgggc atgccgtcgc gcagggcttt
 301 gagcacgtca cggcggtcga agtccttacc gccgtagcgg tagccgtcca cggccagcag
 361 cactttcggt tcgatctgcg cgaaccggtc gaggacgctg cgcaccccga agtcggggga
 421 acaggacgac caggtcgcac cgatcgcggc gcaggcgagg aatgcggccg tcgcctcggc
 481 gatgttcggc aggtaggcca cgacccggtc gccggggccc accccgaggc tgcggagggc
 541 cgcagcgatc gcggcggtgc gggtccgcag ttctccccag gtccactcgg tcaacggccg
 601 gagttcggac gcgtgccgga tcgccacggc tgatgggtca cggtcgcgga agatgtgctc
 661 ggcgtagttg agggtggcgc cggggaacca gacggcgccg ggcatggcgt cggaggcgag
 721 cactgtggtg tacggggtgg cggcgcgcac ccggtagtac tcccagatcg cggaccagaa
 781 tccttcgagg tcggttaccg accagcgcca cagtgcctcg tagtccggtg cgtccacacc
 841 gcggtgctcc cgcacccagc gggtgaacgc ggtgaggttg gcgcgttctt tgcgctcctc
 901 gtcgggactc cacaggatcg gcggctgcgg cttgagtgtc atgaaacgcg accccttcgt
 961 ggacggtgcg gatgcggtga gcgtcgggtg cctcccctaa cgctccccgg tgacggagtg
1021 ttgtgcacca catctagcac gcgggacgcg gaaaccgtat ggagaaaaca cctacaaccc
1081 cggccggacg gtgggtttcg gccacactta ggggtcgggt gcctgcttgc cgggcagggc
1141 agtcccgggg tgctgtggtg cgggcgggag ggctgtcgct tcgaggtgtg ccggcgggac
1201 actccgggcc tcagccgtac ccgcaacggg gacagttctc ctccttccg ggctggatgg
1261 tcccttcccc cgaaatgcgg cgagatctcc cagtcagccc ggaaaacacc cgctgtgccc
1321 aggtactctt tgcttcgaac agacaggccg gacggtccac gggggaggtt tgtgggcagc
1381 ggaccacgtg cggcgaccag acgacggttg ttcctcggta tccccgctct tgtacttgtg
1441 acagcgctca cgctggtctt ggctgtcccg acggggcgcg agacgctgtg gcgcatgtgg
1501 tgtgaggcca cccaggactg gtgcctgggg gtgccggtcg actcccgcgg acagcctgcg
1561 gaggacggcg agtttctgct gctttctccg gtccaggcag cgacctgggg gaactattac
1621 gcgctcgggg attcgtactc ttcggggac ggggcccgcg actactatcc cggcaccgcg
1681 gtgaagggcg gttgctggcg gtccgctaac gcctatccgg agctggtcgc cgaagcctac
1741 gacttcgccg gacacttgtc gttcctggcc tgcagcggcc agcgcggcta cgccatgctt
1801 gacgctatcg acgaggtcgg ctcgcagctg gactggaact cccctcacac gtcgctggtg
1861 acgatcggga tcggcggcaa cgatctgggg ttctccacgg ttttgaagac ctgcatggtg
1921 cgggtgccgc tgctggacag caaggcgtgc acggaccagg aggacgctat ccgcaagcgg
1981 atggcgaaat tcgagacgac gtttgaagag ctcatcagcg aagtgcgcac ccgcgcgccg
2041 gacgcccgga tccttgtcgt gggctacccc cggattttc cggaggaacc gaccggcgcc
2101 tactacacgc tgaccgcgag caaccagcgg tggctcaacg aaaccattca ggagttcaac
2161 cagcagctcg ccgaggctgt cgcggtccac gacgaggaga ttgccgcgtc gggcggggtg
2221 ggcagcgtgg agttcgtgga cgtctaccac gcgttggacg gccacgagat cggctcggac
2281 gagccgtggg tgaacggggt gcagttgcgg gacctcgcca ccggggtgac tgtggaccgc
2341 agtaccttcc accccaacgc cgctgggcac cgggcggtcg gtgagcgggt catcgagcag
2401 atcgaaaccg gcccgggccg tccgctctat gccactttcg cggtggtggc ggggcgacc
2461 gtggacactc tcgcgggcga ggtggggtga cccggcttac cgtccggccc gcaggtctgc
2521 gagcactgcg gcgatctggt ccactgccca gtgcagttcg tcttcggtga tgaccagcgg
2581 cggggagagc cggatcgttg agccgtgcgt gtctttgacg agcacacccc gctgcaggag
2641 ccgttcgcac agttctcttc cggtggccag agtcgggtcg acgtcgatcc cagcccacag
2701 gccgatgctg cgggccgcga ccacgccgtt gccgaccagt tggtcgaggc gggcgcgcag
2761 cacggggggcg agggcgcgga catggtccag gtaaggccg tcgcggacga ggctcaccac
2821 ggcagtgccg accgcgcagg cgagggcgtt gccgccgaag gtgctgccgt gctggccggg
2881 gcggatcacg tcgaagactt ccgcgtcgcc taccgccgcc gccacgggca ggatgccgcc
2941 gcccagcgct ttgccgaaca ggtagatatc ggcgtcgact ccgctgtggt cgcaggcccg
```

FIGURE 50

(SEQ ID No. 40)

```
  1 vgsgpraatr rrlflgipal vlvtaltlvl avptgretlw rmwceatqdw clgvpvdsrg
 61 qpaedgefll lspvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg
```

FIGURE 51

(SEQ ID No. 41)

```
  1 mrttviaasa lllagcadg areetagapp gessggiree gaeastsitd vyialgdsya
 61 amggrdqplr gepfclrssg nypellhaev tdltcqgavt gdlleprtlg ertlpaqvda
121 ltedttlvtl siggndlgfg evagcireri agenaddcvd llgetigeql dqlppqldrv
181 heairdragd aqvvvtgylp lvsagdcpel gdvseadrrw aveltgqine tvreaaerhd
241 alfvlpddad ehtscappqq rwadiqgqqt dayplhptsa gheamaaavr dalglepvqp
```

FIGURE 52

(SEQ ID No. 42)

```
   1 ttctggggtg ttatggggtt gttatcggct cgtcctgggt ggatcccgcc aggtggggta
  61 ttcacggggg acttttgtgt ccaacagccg agaatgagtg ccctgagcgg tgggaatgag
 121 gtgggcgggg ctgtgtcgcc atgaggggc ggcgggctct gtggtgcccc gcgaccccg
 181 gccccggtga gcggtgaatg aaatccggct gtaatcagca tcccgtgccc accccgtcgg
 241 ggaggtcagc gcccggagtg tctacgcagt cggatcctct cggactcggc catgctgtcg
 301 gcagcatcgc gctcccgggt cttggcgtcc ctcggctgtt ctgcctgctg tccctggaag
 361 gcgaaatgat caccggggag tgatacaccg gtggtctcat cccggatgcc cacttcggcg
 421 ccatccggca attcgggcag ctccgggtgg aagtaggtgg catccgatgc gtcggtgacg
 481 ccatagtggg cgaagatctc atcctgctcg agggtgctca ggccactctc cggatcgata
 541 tcggggcgt ccttgatggc gtccttgctg aaaccgaggt gcagcttgtg ggcttccaat
 601 ttcgcaccac ggagcgggac gaggctggaa tgacggccga agagcccgtg gtggacctca
 661 acgaaggtgg gtagtcccgt gtcatcattg aggaacacgc cctccaccgc acccagcttg
 721 tggccggagt tgtcgtaggc gctggcatcc agaagggaaa cgatctcata tttgtcggtg
 781 tgctcagaca tgatcttcct ttgctgtcgg tgtctggtac taccacggta gggctgaatg
 841 caactgttat ttttctgtta ttttaggaat tggtccatat cccacaggct ggctgtggtc
 901 aaatcgtcat caagtaatcc ctgtcacaca aaatgggtgg tgggagccct ggtcgcggtt
 961 ccgtgggagg cgccgtgccc cgcaggatcg tcggcatcgg cggatctggc cggtaccccg
1021 cggtgaataa aatcattctg taaccttcat cacggttggt tttaggtatc cgcccctttc
1081 gtcctgaccc cgtccccggc gcgcgggagc ccgcggttg cggtagacag gggagacgtg
1141 gacaccatga ggacaacggt catcgcagca agcgcattac tccttctcgc cggatgcgcg
1201 gatggggccc gggaggagac cgccggtgca ccgccgggtg agtcctccgg gggcatccgg
1261 gaggagggg cggaggcgtc gacaagcatc accgacgtct acatcgccct cggggattcc
1321 tatgcggcga tgggcgggcg ggatcagccg ttacggggtg agccgttctg cctgcgctcg
1381 tccggtaatt acccggaact cctccacgca gaggtcaccg atctcacctg ccaggggcg
1441 gtgaccgggg atctgctcga acccaggacg ctggggagc gcacgctgcc ggcgcaggtg
1501 gatgcgctga cggaggacac caccctggtc accctctcca tcggggcaa tgacctcgga
1561 ttcggggagg tggcgggatg catccgggaa cggatcgccg gggagaacgc tgatgattgc
1621 gtggacctgc tggggaaaac catcggggag cagctcgatc agcttccccc gcagctggac
1681 cgcgtgcacg aggctatccg ggaccgcgcc ggggacgcgc aggttgtggt caccggttac
1741 ctgccgctcg tgtctgccgg ggactgcccc gaactggggg atgtctccga gcggatcgt
1801 cgttgggcgg ttgagctgac cggcagatc aacgagaccg tgcgcgaggc ggccgaacga
1861 cacgatgccc tctttgtcct gcccgacgat gccgatgagc acaccagttg tgcaccccca
1921 cagcagcgct gggcggatat ccagggccaa cagaccgatg cctatccgct gcacccgacc
1981 tccgccggcc atgaggcgat ggccgccgcc gtccgggacg cgctgggcct ggaaccggtc
2041 cagccgtagc gccgggcgcg cgcttgtcga cgaccaaccc atgccaggct gcagtcacat
2101 ccgcacatag cgcgcgcggg cgatggagta cgcaccatag aggatgagcc cgatgccgac
2161 gatgatgagc agcacactgc cgaaggggttg ttccccgagg gtgcgcagag ccgagtccag
2221 acctgcggcc tgctccggat catgggccca accggcgatg acgatcaaca cccccaggat
2281 cccgaaggcg ataccacggg cgacataacc ggctgttccg gtgatgatga tcgcggtccc
2341 gacctgcct gaccccgcac ccgcctccag atcctcccgg aaatcccggg tggcccctt
2401 ccagaggttg tagacacccg ccccagtac caccagcccg gcgaccacaa ccagcaccac
2461 accccagggt tgggatagga cggtggcggt gacatcggtg gcggtctccc catcggaggt
2521 gctgccgccc cgggcgaagg tggaggtggt caccgccagg agaagtaga ccatggccat
2581 gaccgccccc ttggccctt ccttgaggtc ctcgcccgcc agcagctggc tcaattgcca
2641 gagtcccagg gccgccaggg cgatgacggc aacccacagg aggaactgcc cacccggagc
2701 ctccgcgatg gtggccaggg cacctgaatt cgaggcctca tcacccgaac cgccggatcc
2761 agtggcgatg cgcaccgcga tccacccgat gaggatgtgc agtatgccca ggacaatgaa
2821 accacctctg gccagggtgg tcagcgcggg gtggtcctcg gcctggtcgg cagcccgttc
2881 gatcgtccgt ttcgcggatc tggtgtcgcc cttatccata gctcccattg aaccgccttg
2941 aggggtgggc ggccactgtc agggcggatt gtgatctgaa ctgtgatgtt ccatcaaccc
```

FIGURE 53

(SEQ ID No. 43)

```
  1 mrrfrlvgfl sslvlaagaa ltgaataqaa qpaaadgyva lgdsyssgvg agsyisssgd
 61 ckrstkahpy lwaaahspst fdftacsgar tgdvlsgqlg plssgtglvs isiggndagf
121 adtmttcvlq sessclsria taeayvdstl pgkldgvysa isdkapnahv vvigyprfyk
181 lgttciglse tkrtainkas dhlntvlaqr aaahgftfgd vrttftghel csgspwlhsv
241 nwlnigesyh ptaagqsggy lpvlngaa
```

Figure 54

(SEQ ID No. 44)

```
   1 cccggcggcc cgtgcaggag cagcagccgg cccgcgatgt cctcgggcgt cgtcttcatc
    61 aggccgtcca tcgcgtcggc gaccggcgcc gtgtagttgg cccggacctc gtcccaggtg
   121 cccgcggcga tctggcgggt ggtgcggtgc gggccgcgcc gaggggagac gtaccagaag
   181 cccatcgtca cgttctccgg ctgcggttcg ggctcgtccg ccgctccgtc cgtcgcctcg
   241 ccgagcacct tctcggcgag gtcggcgctg gtgccgtca ccgtgacgtc ggcgccccgg
   301 ctccagcgcg agatcagcag cgtccagccg tcgccctccg ccagcgtcgc gctgcggtcg
   361 tcgtcgcggg cgatccgcag cacgcgcgcg ccgggcggca gcagcgtggc gccggaccgt
   421 acgcggtcga tgttcgccgc gtgcgagtac ggctgctcac ccgtggcgaa acggccgagg
   481 aacagcgcgt cgacgacgtc ggacggggag tcgctgtcgt ccacgttgag ccggatcggc
   541 agggcttcgt gcgggttcac ggacatgtcg ccatgatcgg gcacccggcc gccgcgtgca
   601 cccgctttcc cgggcacgca cgacaggggc tttctcgccg tcttccgtcc gaacttgaac
   661 gagtgtcagc catttcttgg catggacact tccagtcaac gcgcgtagct gctaccacgg
   721 ttgtggcagc aatcctgcta agggaggttc catgagacgt ttccgacttg tcggcttcct
   781 gagttcgctc gtcctcgccg ccggcgccgc cctcaccggg gcagcgaccg cccaggcggc
   841 ccaacccgcc gccgccgacg gctatgtggc cctcggcgac tcctactcct ccggggtcgg
   901 agcgggcagc tacatcagct cgagcggcga ctgcaagcgc agcacgaagg cccatcccta
   961 cctgtgggcg gccgcccact cgccctccac gttcgacttc accgcctgtt ccggcgcccg
  1021 tacgggtgat gttctctccg gacagctcgg cccgctcagc tccggcaccg gcctcgtctc
  1081 gatcagcatc ggcggcaacg acgccggttt cgccgacacc atgacgacct gtgtgctcca
  1141 gtccgagagc tcctgcctgt cgcggatcgc caccgccgag cgtacgtcg actcgacgct
  1201 gcccggcaag ctcgacggcg tctactcggc aatcagcgac aaggcgccga acgcccacgt
  1261 cgtcgtcatc ggctacccgc gcttctacaa gctcggcacc acctgcatcg gcctgtccga
  1321 gaccaagcgg acggcgatca acaaggcctc cgaccacctc aacaccgtcc tgcccagcg
  1381 cgccgccgcc cacggcttca ccttcggcga cgtacgcacc accttcaccg gccacgagct
  1441 gtgctccggc agccctggc tgcacagcgt caactggctg aacatcggcg agtcgtacca
  1501 ccccaccgcg gccggccagt ccggtggcta cctgccggtc ctcaacggcg ccgcctgacc
  1561 tcaggcggaa ggagaagaag aaggagcgga gggagacgag gagtgggagg cccgcccga
  1621 cggggtcccc gtccccgtct ccgtctccgt cccggtcccg caagtcaccg agaacgccac
  1681 cgcgtcggac gtggcccgca ccggactccg cacctccacg cgcacggcac tctcgaacgc
  1741 gccggtgtcg tcgtgcgtcg tcaccaccac gccgtcctgg cgcgagcgct cgccgcccga
  1801 cgggaaggac agcgtccgcc accccggatc ggagaccgac ccgtccgcgg tcacccaccg
  1861 gtagccgacc tccgcgggca gccgcccgac cgtgaacgtc gccgtgaacg cgggtgcccg
  1921 gtcgtgcggc ggcggacagg ccccgagta gtgggtgcgc gagcccacca cggtcacctc
  1981 caccgactgc gctgcggggc
```

FIGURE 55

(SEQ ID No. 45)

```
  1 mrrsritayv tslllavgca ltgaataqas paaaatgyva lgdsyssgvg agsylsssgd
 61 ckrsskaypy lwqaahspss fsfmacsgar tgdvlanqlg tlnsstglvs ltiggndagf
121 sdvmttcvlq sdsaclsrin takayvdstl pgqldsvyta istkapsahv avlgyprfyk
181 lggsclagls etkrsainda adylnsaiak raadhgftfg dvkstftghe icssstwlhs
241 ldllnigqsy hptaagqsgg ylpvmnsva
```

FIGURE 56

SEQ ID No. 46

```
   1 ccaccgccgg gtcggcggcg agtctcctgg cctcggtcgc ggagaggttg gccgtgtagc
  61 cgttcagcgc ggcgccgaac gtcttcttca ccgtgccgcc gtactcgttg atcaggccct
 121 tgcccttgct cgacgcggcc ttgaagccgg tgcccttctt gagcgtgacg atgtagctgc
 181 ccttgatcgc ggtgggggag ccggcggcga gcaccgtgcc ctcggccggg gtggcctggg
 241 cgggcagtgc ggtgaatccg cccacgaggg cgccggtcgc cacggcggtt atcgcggcga
 301 tccggatctt cttgctacgc agctgtgcca tacgagggag tcctcctctg ggcagcggcg
 361 cgcctgggtg gggcgcacgg ctgtgggggg tgcgcgcgtc atcacgcaca cggccctgga
 421 gcgtcgtgtt ccgccctggg ttgagtaaag cctcggccat ctacgggggt ggctcaaggg
 481 agttgagacc ctgtcatgag tctgacatga gcacgcaatc aacggggccg tgagcacccc
 541 ggggcgaccc cggaaagtgc cgagaagtct tggcatggac acttcctgtc aacacgcgta
 601 gctggtacga cggttacggc agagatcctg ctaaagggag gttccatgag acgttcccga
 661 attacggcat acgtgacctc actcctcctc gccgtcggct gcgccctcac cggggcagcg
 721 acggcgcagg cgtccccagc cgccgcggcc acgggctatg tggccctcgg cgactcgtac
 781 tcgtccggtg tcggcgccgg cagctacctc agctccagcg gcgactgcaa gcgcagttcg
 841 aaggcctatc cgtacctctg gcaggccgcg cattcaccct cgtcgttcag tttcatggct
 901 tgctcgggcg ctcgtacggg tgatgtcctg gccaatcagc tcggcaccct gaactcgtcc
 961 accggcctgg tctccctcac catcggaggc aacgacgcgg gcttctccga cgtcatgacg
1021 acctgtgtgc tccagtccga cagcgcctgc ctctcccgca tcaacacggc gaaggcgtac
1081 gtcgactcca ccctgcccgg ccaactcgac agcgtgtaca cggcgatcag cacgaaggcc
1141 ccgtcggccc atgtggccgt gctgggctac ccccgcttct acaaactggg cggctcctgc
1201 ctcgcgggcc tctcggagac caagcggtcc gccatcaacg acgcggccga ctatctgaac
1261 agcgccatcg ccaagcgcgc cgccgaccac ggcttcacct tcggcgacgt caagagcacc
1321 ttcaccggcc atgagatctg ctccagcagc acctggctgc acagtctcga cctgctgaac
1381 atcggccagt cctaccaccc gaccgcggcc ggccagtccg gcggctatct gccggtcatg
1441 aacagcgtgg cctgagctcc cacggcctga attttaagg cctgaatttt taaggcgaag
1501 gtgaaccgga agcggaggcc ccgtccgtcg gggtctccgt cgcacaggtc accgagaacg
1561 gcacggagtt ggacgtcgtg cgcaccgggt cgcgcacctc gacggcgatc tcgttcgaga
1621 tcgttccgct cgtgtcgtac gtggtgacga acacctgctt ctgctgggtc tttccgccgc
1681 tcgccgggaa ggacagcgtt ttccagcccg gatccgggac ctcgcccttc ttggtcaccc
1741 agcggtactc cacctcgacc ggcacccggc ccaccgtgaa ggtcgccgtg aacgtgggcg
1801 cctgggcggt gggcggcggg caggcaccgg agtagtcggt gtgcacgccg gtgaccgtca
1861 ccttcacgga ctgggccggc ggggtcgtcg taccgccgcc gccaccgccg cctcccggag
1921 tggagcccga gctgtggtcg ccccgccgt cggcgttgtc gtcctcgggg gttttcgaac
```

FIGURE 57

SEQ ID No. 47

1 mgsgpraatr rrifigipal vivtaltlvl avptgretlw rmwceatqdw clgvpvdsrg
61 qpaedgefll ispvqaatwg nyyalgdsys sgdgardyyp gtavkggcwr sanaypelva
121 eaydfaghls flacsgqrgy amldaidevg sqldwnspht slvtigiggn dlgfstvlkt
181 cmvrvpllds kactdqedai rkrmakfett feelisevrt rapdarilvv gyprifpeep
241 tgayytltas nqrwlnetiq efnqqlaeav avhdeeiaas ggvgsvefvd vyhaldghei
301 gsdepwvngv qlrdlatgvt vdrstfhpna aghravgerv ieqietgpgr plyatfavva
361 gatvdtlage vg

FIGURE 58

SEQ ID No. 48

1       ctgcagacac ccgccccgcc ttctcccgga tcgtcatgtt cggcgactcc ctcagcgaca
61      ccggcaagat gtactccaag atgcgcggct acctgccgtc ctccccgccg tactacgagg
121     gccgcttctc gaacggcccg gtctggctgg agcagctgac gaagcagttc cccggcctga
181     cgatcgccaa cgaggccgag ggggcgcga ccgcagtcgc ctacaacaag atctcctgga
241     acccgaagta ccaggtcatt aacaacctcg actacgaggt cacccagttc ttgcagaagg
301     actcgttcaa gcccgacgac ctggtcatcc tgtgggtggg cgccaacgac tacctggcct
361     acggttggaa cacggagcag gacgccaagc gggtgcgcga cgccatctcg gacgcggcaa
421     accgcatggt cctgaacggc gcgaagcaga tcctgctgtt caacctgccc gacctgggcc
481     agaacccgtc cgcccgctcc cagaaggtcg tcgaggccgt ctcgcacgtg tccgcctacc
541     acaacaagct gctcctcaac ctcgcccggc agctcgcccc gacgggcatg gtcaagctgt
601     tcgagatcga caagcagttc gcggagatgc tgcgcgaccc ccagaacttc ggcctgagcg
661     acgtggagaa cccgtgctac gacggcggct acgtgtggaa gccgttcgcc acccggtccg
721     tctcgaccga ccggcagctg tcggccttct cgccccagga gcgcctggcg atcgctggca
781     acccgctcct ggcacaggcg gtagcttcgc cgatggcccg ccgctcggcc tcgcccctca
841     actgcgaggg caagatgttc tgggaccagg tccaccccac caccgtggtc cacgccgccc
901     tctcggagcg cgccgccacc ttcatcgaga cccagtacga gttcctcgcc cactagtcta
961     gaggatcc Figure 61
1. L131
2. S.avermitilis
3. T.fusca
4. Consensus

```
              1                                                    50
1  (1)   --------MRLTRSLSAASVIVFALLLALLGISPAQAAG----------
2  (1)   --------MRRSRITAYVTSLLLAVGCALTGAATAQASPA----------
3  (1)   VGSGPRAATRRRLFLGIPALVLVTALTLVLAVPTGRETLWRMWCEATQDW
4  (1)           MRRSRFLA  ALILLTLA  AL GAA  ARAAP 51                                                   100
1  (32)  ----------------------P-AYVALGDSYSSGNGAGSYID
2  (33)  ----------------------AAATGYVALGDSYSSGVGAGSYLS
3  (51)  CLGVPVDSRGQPAEDGEFLLLSPVQAATWGNYYALGDSYSSGDGARDYYP
4  (51)                        A A  YVALGDSYSSG GAGSY 101                                                  150
1  (53)  SSGD---CHRSNNAYPARWAAANAP---SSFTFAACSGAVTTDVIN----
2  (57)  SSGD---CKRSSKAYPYLWQAAHSP---SSFSFMACSGARTGDVLA----
3  (101) GTAVKGGCWRSANAYPELVAEAYDFA--GHLSFLACSGQRGYAMLDAIDE
4  (101) SSGD   C RSTKAYPALWAAAHA    SSFSF ACSGARTYDVLA 151                                                  200
1  (93)  --NQLGALNAST--GLVSITIGGNDAGFADAMTTCVTS------SDSTCL
2  (97)  --NQLGTLNSST--GLVSLTIGGNDAGFSDVMTTCVLQ------SDSACL
3  (149) VGSQLDWNSPHT--SLVTIGIGGNDLGFSTVLKTCMVR------VPLLDS
4  (151)    QL  LNS T   LVSITIGGNDAGFAD MTTCVL       SDSACL 201                                                  250
1  (133) NRLATATNYINTTLLA-------RLDAVYSQIKARAPNARVVVLGYPRMY
2  (137) SRINTAKAYVDSTLPG-------QLDSVYTAISTKAPSAHVAVLGYPRFY
3  (191) KACTDQEDAIRKRMAKF----ETTFEELISEVRTRAPDARILVVGYPRIF
4  (201)  RIA AK YI  TLPA       RLDSVYSAI  TRAP ARVVVLGYPRIY 251                                                  300
1  (176) LASNPWYCLGLSNTKRAAINTTADTLNSVISSRATAH----------GF
2  (180) KLGG-SCLAGLSETKRSAINDAADYLNSAIAKRAADH----------GF
3  (237) PEEPTGAYYTLTASNQRWLNETIQEFNQQLAEAVAVHDEEIAASGGVGSV
4  (251)       SG   LGLS TKRAAINDAAD LNSVIAKRAADH         GF 301                                                  350
1  (215) RFGDVRPTFNNHELFFGNDWLHSLTLP---------------VWESYH
2  (218) TFGDVKSTFTGHEICSSSTWLHSLDLLN--------------IGQSYH
3  (287) EFVDVYHALDGHEIGSDEPWVNGVQLRDLATG----------VTVDRSTFH
4  (301) TFGDV  TF GHELCSA PWLHSLTLP                V  SYH 351                                                  395
1  (248) PTSTGHQSGYLPVLNANSST-----------------------
2  (252) PTAAGQSGGYLPVMNSVA-------------------------
3  (328) PNAAGHRAVGERVIEQIETGPGRPLYATFAVVAGATVDTLAGEVG
4  (351) PTA GHAAGYLPVLNSI T
```

SEQUENCE LISTING

```
<160> NUMBER OF SEQ ID NOS: 53

<210> SEQ ID NO 1
<211> LENGTH: 335
<212> TYPE: PRT
<213> ORGANISM: Aeromonas hydrophila

<400> SEQUENCE: 1

Met Lys Lys Trp Phe Val Cys Leu Leu Gly Leu Val Ala Leu Thr Val
1               5                   10                  15

Gln Ala Ala Asp Ser Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
```

-continued

```
                100                 105                 110
Gln Phe Leu Gln Lys Asp Ser Phe Lys Pro Asp Leu Val Ile Leu
            115                 120                 125
Trp Val Gly Ala Asn Asp Tyr Leu Ala Tyr Gly Trp Asn Thr Glu Gln
130                 135                 140
Asp Ala Lys Arg Val Arg Asp Ala Ile Ser Asp Ala Ala Asn Arg Met
145                 150                 155                 160
Val Leu Asn Gly Ala Lys Gln Ile Leu Leu Phe Asn Leu Pro Asp Leu
                165                 170                 175
Gly Gln Asn Pro Ser Ala Arg Ser Gln Lys Val Val Glu Ala Val Ser
            180                 185                 190
His Val Ser Ala Tyr His Asn Gln Leu Leu Leu Asn Leu Ala Arg Gln
        195                 200                 205
Leu Ala Pro Thr Gly Met Val Lys Leu Phe Glu Ile Asp Lys Gln Phe
    210                 215                 220
Ala Glu Met Leu Arg Asp Pro Gln Asn Phe Gly Leu Ser Asp Val Glu
225                 230                 235                 240
Asn Pro Cys Tyr Asp Gly Gly Tyr Val Trp Lys Pro Phe Ala Thr Arg
                245                 250                 255
Ser Val Ser Thr Asp Arg Gln Leu Ser Ala Phe Ser Pro Gln Glu Arg
            260                 265                 270
Leu Ala Ile Ala Gly Asn Pro Leu Leu Ala Gln Ala Val Ala Ser Pro
        275                 280                 285
Met Ala Arg Arg Ser Ala Ser Pro Leu Asn Cys Glu Gly Lys Met Phe
    290                 295                 300
Trp Asp Gln Val His Pro Thr Thr Val Val His Ala Ala Leu Ser Glu
305                 310                 315                 320
Arg Ala Ala Thr Phe Ile Ala Asn Gln Tyr Glu Phe Leu Ala His
                325                 330                 335

<210> SEQ ID NO 2
<211> LENGTH: 361
<212> TYPE: PRT
<213> ORGANISM: Artificial Sequence
<220> FEATURE:
<223> OTHER INFORMATION: Pfam00657 consensus sequence from database
      version 6.

<400> SEQUENCE: 2

Ile Val Ala Phe Gly Asp Ser Leu Thr Asp Gly Glu Ala Tyr Tyr Gly
1               5                   10                  15
Asp Ser Asp Gly Gly Gly Trp Gly Ala Gly Leu Ala Asp Arg Leu Thr
                20                  25                  30
Ala Leu Leu Arg Leu Arg Ala Arg Pro Arg Gly Val Ala Val Phe Asn
            35                  40                  45
Arg Gly Ile Ser Gly Arg Thr Ser Asp Gly Arg Leu Ile Val Asp Ala
        50                  55                  60
Leu Val Ala Leu Leu Phe Leu Ala Gln Ser Leu Gly Leu Pro Asn Leu
65                  70                  75                  80
Pro Pro Tyr Leu Ser Gly Asp Phe Leu Arg Gly Ala Asn Phe Ala Ser
                85                  90                  95
Ala Gly Ala Thr Ile Leu Pro Thr Ser Gly Pro Phe Leu Ile Gln Val
            100                 105                 110
Gln Phe Lys Asp Phe Lys Ser Gln Val Leu Glu Leu Arg Gln Ala Leu
        115                 120                 125
```

```
Gly Leu Leu Gln Glu Leu Leu Arg Leu Leu Pro Val Leu Asp Ala Lys
            130                 135                 140
Ser Pro Asp Leu Val Thr Ile Met Ile Gly Thr Asn Asp Leu Ile Thr
145                 150                 155                 160
Ser Ala Phe Phe Gly Pro Lys Ser Thr Glu Ser Asp Arg Asn Val Ser
                    165                 170                 175
Val Pro Glu Phe Lys Asp Asn Leu Arg Gln Leu Ile Lys Arg Leu Arg
                180                 185                 190
Ser Asn Asn Gly Ala Arg Ile Ile Val Leu Ile Thr Leu Val Ile Leu
            195                 200                 205
Asn Leu Gly Pro Leu Gly Cys Leu Pro Leu Lys Leu Ala Leu Ala Leu
210                 215                 220
Ala Ser Ser Lys Asn Val Asp Ala Ser Gly Cys Leu Glu Arg Leu Asn
225                 230                 235                 240
Glu Ala Val Ala Asp Phe Asn Glu Ala Leu Arg Glu Leu Ala Ile Ser
                    245                 250                 255
Lys Leu Glu Asp Gln Leu Arg Lys Asp Gly Leu Pro Asp Val Lys Gly
                260                 265                 270
Ala Asp Val Pro Tyr Val Asp Leu Tyr Ser Ile Phe Gln Asp Leu Asp
            275                 280                 285
Gly Ile Gln Asn Pro Ser Ala Tyr Val Tyr Gly Phe Glu Thr Thr Lys
290                 295                 300
Ala Cys Cys Gly Tyr Gly Arg Tyr Asn Tyr Asn Arg Val Cys Gly
305                 310                 315                 320
Asn Ala Gly Leu Cys Asn Val Thr Ala Lys Ala Cys Asn Pro Ser Ser
                    325                 330                 335
Tyr Leu Leu Ser Phe Leu Phe Trp Asp Gly Phe His Pro Ser Glu Lys
                340                 345                 350
Gly Tyr Lys Ala Val Ala Glu Ala Leu
            355                 360

<210> SEQ ID NO 3
<211> LENGTH: 335
<212> TYPE: PRT
<213> ORGANISM: Aeromonas hydrophila

<400> SEQUENCE: 3

Met Lys Lys Trp Phe Val Cys Leu Leu Gly Leu Val Ala Leu Thr Val
1               5                   10                  15
Gln Ala Ala Asp Ser Arg Pro Ala Phe Ser Arg Ile Val Met Phe Gly
                20                  25                  30
Asp Ser Leu Ser Asp Thr Gly Lys Met Tyr Ser Lys Met Arg Gly Tyr
            35                  40                  45
Leu Pro Ser Ser Pro Pro Tyr Tyr Glu Gly Arg Phe Ser Asn Gly Pro
        50                  55                  60
Val Trp Leu Glu Gln Leu Thr Asn Glu Phe Pro Gly Leu Thr Ile Ala
65                  70                  75                  80
Asn Glu Ala Glu Gly Gly Pro Thr Ala Val Ala Tyr Asn Lys Ile Ser
                85                  90                  95
Trp Asn Pro Lys Tyr Gln Val Ile Asn Asn Leu Asp Tyr Glu Val Thr
                100                 105                 110
Gln Phe Leu Gln Lys Asp Ser Phe Lys Pro Asp Asp Leu Val Ile Leu
            115                 120                 125
Trp Val Gly Ala Asn Asp Tyr Leu Ala Tyr Gly Trp Asn Thr Glu Gln
        130                 135                 140
```

-continued

```
Asp Ala Lys Arg Val Arg Asp Ala Ile Ser Asp Ala Ala Asn Arg Met
145                 150                 155                 160

Val Leu Asn Gly Ala Lys Glu Ile Leu Leu Phe Asn Leu Pro Asp Leu
            165                 170                 175

Gly Gln Asn Pro Ser Ala Arg Ser Gln Lys Val Val Glu Ala Ala Ser
        180                 185                 190

His Val Ser Ala Tyr His Asn Gln Leu Leu Asn Leu Ala Arg Gln
    195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Gln Arg
225                 230                 235                 240

Asn Ala Cys Tyr Gly Gly Ser Tyr Val Trp Lys Pro Phe Ala Ser Arg
                245                 250                 255

Ser Ala Ser Thr Asp Ser Gln Leu Ser Ala Phe Asn Pro Gln Glu Arg
            260                 265                 270

Leu Ala Ile Ala Gly Asn Pro Leu Leu Ala Gln Ala Val Ala Ser Pro
        275                 280                 285

Met Ala Ala Arg Ser Ala Ser Thr Leu Asn Cys Glu Gly Lys Met Phe
290                 295                 300

Trp Asp Gln Val His Pro Thr Thr Val Val His Ala Ala Leu Ser Glu
305                 310                 315                 320

Pro Ala Ala Thr Phe Ile Glu Ser Gln Tyr Glu Phe Leu Ala His
                325                 330                 335

<210> SEQ ID NO 4
<211> LENGTH: 336
<212> TYPE: PRT
<213> ORGANISM: Aeromonas salmonicida

<400> SEQUENCE: 4

Met Lys Lys Trp Phe Val Cys Leu Leu Gly Leu Ile Ala Leu Thr Val
1               5                   10                  15

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Tyr Asn Asn Leu Asp Tyr Glu Val Thr
            100                 105                 110

Gln Phe Leu Gln Lys Asp Ser Phe Lys Pro Asp Leu Val Ile Leu
        115                 120                 125

Trp Val Gly Ala Asn Asp Tyr Leu Ala Tyr Gly Trp Asn Thr Glu Gln
130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
            165                 170                 175

Gly Gln Asn Pro Ser Ala Arg Ser Gln Lys Val Val Glu Ala Val Ser
```

```
            180                 185                 190
His Val Ser Ala Tyr His Asn Lys Leu Leu Asn Leu Ala Arg Gln
            195                 200                 205

Leu Ala Pro Thr Gly Met Val Lys Leu Phe Glu Ile Asp Lys Gln Phe
210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
                260                 265                 270

Leu Ala Ile Ala Gly Asn Pro Leu Leu Ala Gln Ala Val Ala Ser Pro
                275                 280                 285

Met Ala Arg Arg Ser Ala Ser Pro Leu Asn Cys Glu Gly Lys Met Phe
                290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 5
<211> LENGTH: 295
<212> TYPE: PRT
<213> ORGANISM: Streptomyces coelicolor

<400> SEQUENCE: 5

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
                20                  25                  30

Pro Ala Gln Ala Thr Pro Thr Leu Asp Tyr Val Ala Leu Gly Asp Ser
                35                  40                  45

Tyr Ser Ala Gly Ser Gly Val Leu Pro Val Asp Pro Ala Asn Leu Leu
        50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
                100                 105                 110

Gly Thr Gly Thr Asp Leu Val Thr Leu Thr Ile Gly Gly Asn Asp Asn
                115                 120                 125

Ser Thr Phe Ile Asn Ala Ile Thr Ala Cys Gly Thr Ala Gly Val Leu
        130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
                180                 185                 190

Tyr Pro Trp Ile Thr Pro Ala Thr Ala Asp Pro Ser Cys Phe Leu Lys
                195                 200                 205

Leu Pro Leu Ala Ala Gly Asp Val Pro Tyr Leu Arg Ala Ile Gln Ala
        210                 215                 220
```

```
His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295

<210> SEQ ID NO 6
<211> LENGTH: 295
<212> TYPE: PRT
<213> ORGANISM: Streptomyces coelicolor

<400> SEQUENCE: 6

Met Pro Lys Pro Ala Leu Arg Arg Val Met Thr Ala Thr Val Ala Ala
1               5                   10                  15

Val Gly Thr Leu Ala Leu Gly Leu Thr Asp Ala Thr Ala His Ala Ala
                20                  25                  30

Pro Ala Gln Ala Thr Pro Thr Leu Asp Tyr Val Ala Leu Gly Asp Ser
            35                  40                  45

Tyr Ser Ala Gly Ser Gly Val Leu Pro Val Asp Pro Ala Asn Leu Leu
        50                  55                  60

Cys Leu Arg Ser Thr Ala Asn Tyr Pro His Val Ile Ala Asp Thr Thr
65                  70                  75                  80

Gly Ala Arg Leu Thr Asp Val Thr Cys Gly Ala Ala Gln Thr Ala Asp
                85                  90                  95

Phe Thr Arg Ala Gln Tyr Pro Gly Val Ala Pro Gln Leu Asp Ala Leu
            100                 105                 110

Gly Thr Gly Thr Asp Leu Val Thr Leu Thr Ile Gly Gly Asn Asp Asn
        115                 120                 125

Ser Thr Phe Ile Asn Ala Ile Thr Ala Cys Gly Thr Ala Gly Val Leu
130                 135                 140

Ser Gly Gly Lys Gly Ser Pro Cys Lys Asp Arg His Gly Thr Ser Phe
145                 150                 155                 160

Asp Asp Glu Ile Glu Ala Asn Thr Tyr Pro Ala Leu Lys Glu Ala Leu
                165                 170                 175

Leu Gly Val Arg Ala Arg Ala Pro His Ala Arg Val Ala Ala Leu Gly
            180                 185                 190

Tyr Pro Trp Ile Thr Pro Ala Thr Ala Asp Pro Ser Cys Phe Leu Lys
        195                 200                 205

Leu Pro Leu Ala Ala Gly Asp Val Pro Tyr Leu Arg Ala Ile Gln Ala
210                 215                 220

His Leu Asn Asp Ala Val Arg Arg Ala Ala Glu Glu Thr Gly Ala Thr
225                 230                 235                 240

Tyr Val Asp Phe Ser Gly Val Ser Asp Gly His Asp Ala Cys Glu Ala
                245                 250                 255

Pro Gly Thr Arg Trp Ile Glu Pro Leu Leu Phe Gly His Ser Leu Val
            260                 265                 270

Pro Val His Pro Asn Ala Leu Gly Glu Arg Arg Met Ala Glu His Thr
        275                 280                 285

Met Asp Val Leu Gly Leu Asp
    290                 295
```

<210> SEQ ID NO 7
<211> LENGTH: 238
<212> TYPE: PRT
<213> ORGANISM: Saccharomyces cerevisiae

<400> SEQUENCE: 7

```
Met Asp Tyr Glu Lys Phe Leu Leu Phe Gly Asp Ser Ile Thr Glu Phe
1               5                   10                  15

Ala Phe Asn Thr Arg Pro Ile Glu Asp Gly Lys Asp Gln Tyr Ala Leu
            20                  25                  30

Gly Ala Ala Leu Val Asn Glu Tyr Thr Arg Lys Met Asp Ile Leu Gln
        35                  40                  45

Arg Gly Phe Lys Gly Tyr Thr Ser Arg Trp Ala Leu Lys Ile Leu Pro
    50                  55                  60

Glu Ile Leu Lys His Glu Ser Asn Ile Val Met Ala Thr Ile Phe Leu
65                  70                  75                  80

Gly Ala Asn Asp Ala Cys Ser Ala Gly Pro Gln Ser Val Pro Leu Pro
                85                  90                  95

Glu Phe Ile Asp Asn Ile Arg Gln Met Val Ser Leu Met Lys Ser Tyr
            100                 105                 110

His Ile Arg Pro Ile Ile Ile Gly Pro Gly Leu Val Asp Arg Glu Lys
        115                 120                 125

Trp Glu Lys Glu Lys Ser Glu Ile Ala Leu Gly Tyr Phe Arg Thr
    130                 135                 140

Asn Glu Asn Phe Ala Ile Tyr Ser Asp Ala Leu Ala Lys Leu Ala Asn
145                 150                 155                 160

Glu Glu Lys Val Pro Phe Val Ala Leu Asn Lys Ala Phe Gln Gln Glu
                165                 170                 175

Gly Gly Asp Ala Trp Gln Gln Leu Leu Thr Asp Gly Leu His Phe Ser
            180                 185                 190

Gly Lys Gly Tyr Lys Ile Phe His Asp Glu Leu Leu Lys Val Ile Glu
        195                 200                 205

Thr Phe Tyr Pro Gln Tyr His Pro Lys Asn Met Gln Tyr Lys Leu Lys
    210                 215                 220

Asp Trp Arg Asp Val Leu Asp Asp Gly Ser Asn Ile Met Ser
225                 230                 235
```

<210> SEQ ID NO 8
<211> LENGTH: 347
<212> TYPE: PRT
<213> ORGANISM: Ralstonia sp.

<400> SEQUENCE: 8

```
Met Asn Leu Arg Gln Trp Met Gly Ala Ala Thr Ala Ala Leu Ala Leu
1               5                   10                  15

Gly Leu Ala Ala Cys Gly Gly Gly Thr Asp Gln Ser Gly Asn Pro
            20                  25                  30

Asn Val Ala Lys Val Gln Arg Met Val Val Phe Gly Asp Ser Leu Ser
        35                  40                  45

Asp Ile Gly Thr Tyr Thr Pro Val Ala Gln Ala Val Gly Gly Gly Lys
    50                  55                  60

Phe Thr Thr Asn Pro Gly Pro Ile Trp Ala Glu Thr Val Ala Ala Gln
65                  70                  75                  80

Leu Gly Val Thr Leu Thr Pro Ala Val Met Gly Tyr Ala Thr Ser Val
                85                  90                  95
```

```
Gln Asn Cys Pro Lys Ala Gly Cys Phe Asp Tyr Ala Gln Gly Gly Ser
            100                 105                 110

Arg Val Thr Asp Pro Asn Gly Ile Gly His Asn Gly Ala Gly Ala
        115                 120                 125

Leu Thr Tyr Pro Val Gln Gln Leu Ala Asn Phe Tyr Ala Ala Ser
    130                 135                 140

Asn Asn Thr Phe Asn Gly Asn Asn Asp Val Val Phe Val Leu Ala Gly
145                 150                 155                 160

Ser Asn Asp Ile Phe Phe Trp Thr Thr Ala Ala Thr Ser Gly Ser
                165                 170                 175

Gly Val Thr Pro Ala Ile Ala Thr Ala Gln Val Gln Gln Ala Ala Thr
                180                 185                 190

Asp Leu Val Gly Tyr Val Lys Asp Met Ile Ala Lys Gly Ala Thr Gln
            195                 200                 205

Val Tyr Val Phe Asn Leu Pro Asp Ser Ser Leu Thr Pro Asp Gly Val
    210                 215                 220

Ala Ser Gly Thr Thr Gly Gln Ala Leu Leu His Ala Leu Val Gly Thr
225                 230                 235                 240

Phe Asn Thr Thr Leu Gln Ser Gly Leu Ala Gly Thr Ser Ala Arg Ile
                245                 250                 255

Ile Asp Phe Asn Ala Gln Leu Thr Ala Ala Ile Gln Asn Gly Ala Ser
                260                 265                 270

Phe Gly Phe Ala Asn Thr Ser Ala Arg Ala Cys Asp Ala Thr Lys Ile
            275                 280                 285

Asn Ala Leu Val Pro Ser Ala Gly Gly Ser Ser Leu Phe Cys Ser Ala
    290                 295                 300

Asn Thr Leu Val Ala Ser Gly Ala Asp Gln Ser Tyr Leu Phe Ala Asp
305                 310                 315                 320

Gly Val His Pro Thr Thr Ala Gly His Arg Leu Ile Ala Ser Asn Val
                325                 330                 335

Leu Ala Arg Leu Leu Ala Asp Asn Val Ala His
                340                 345

<210> SEQ ID NO 9
<211> LENGTH: 261
<212> TYPE: PRT
<213> ORGANISM: Streptomyces coelicolor

<400> SEQUENCE: 9

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
```

```
            115                 120                 125
His Leu Arg Gly Lys Ile Ala Thr Tyr Asn Gly His Val Arg Ala Ile
    130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Pro Leu Pro Pro Arg
        195                 200                 205

Gly Thr Leu Asp Val Arg Arg Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 10
<211> LENGTH: 260
<212> TYPE: PRT
<213> ORGANISM: Streptomyces coelicolor

<400> SEQUENCE: 10

Met Gln Thr Asn Pro Ala Tyr Thr Ser Leu Val Ala Val Gly Asp Ser
1               5                   10                  15

Phe Thr Glu Gly Met Ser Asp Leu Leu Pro Asp Gly Ser Tyr Arg Gly
            20                  25                  30

Trp Ala Asp Leu Leu Ala Thr Arg Met Ala Ala Arg Ser Pro Gly Phe
        35                  40                  45

Arg Tyr Ala Asn Leu Ala Val Arg Gly Lys Leu Ile Gly Gln Ile Val
    50                  55                  60

Asp Glu Gln Val Asp Val Ala Ala Ala Met Gly Ala Asp Val Ile Thr
65                  70                  75                  80

Leu Val Gly Gly Leu Asn Asp Thr Leu Arg Pro Lys Cys Asp Met Ala
                85                  90                  95

Arg Val Arg Asp Leu Leu Thr Gln Ala Val Glu Arg Leu Ala Pro His
            100                 105                 110

Cys Glu Gln Leu Val Leu Met Arg Ser Pro Gly Arg Gln Gly Pro Val
        115                 120                 125

Leu Glu Arg Phe Arg Pro Arg Met Glu Ala Leu Phe Ala Val Ile Asp
    130                 135                 140

Asp Leu Ala Gly Arg His Gly Ala Val Val Asp Leu Tyr Gly Ala
145                 150                 155                 160

Gln Ser Leu Ala Asp Pro Arg Met Trp Asp Val Asp Arg Leu His Leu
                165                 170                 175

Thr Ala Glu Gly His Arg Arg Val Ala Glu Ala Val Trp Gln Ser Leu
            180                 185                 190

Gly His Glu Pro Glu Asp Pro Glu Trp His Ala Pro Ile Pro Ala Thr
        195                 200                 205

Pro Pro Pro Gly Trp Val Thr Arg Thr Ala Asp Val Arg Phe Ala
    210                 215                 220
```

```
Arg Gln His Leu Leu Pro Trp Ile Gly Arg Leu Thr Gly Arg Ser
225                 230                 235                 240

Ser Gly Asp Gly Leu Pro Ala Lys Arg Pro Asp Leu Leu Pro Tyr Glu
            245                 250                 255

Asp Pro Ala Arg
            260

<210> SEQ ID NO 11
<211> LENGTH: 454
<212> TYPE: PRT
<213> ORGANISM: Streptomyces coelicolor

<400> SEQUENCE: 11

Met Thr Arg Gly Arg Asp Gly Gly Ala Gly Pro Pro Thr Lys His
1               5                   10                  15

Arg Ala Leu Leu Ala Ala Ile Val Thr Leu Ile Val Ala Ile Ser Ala
            20                  25                  30

Ala Ile Tyr Ala Gly Ala Ser Ala Asp Asp Gly Ser Arg Asp His Ala
            35                  40                  45

Leu Gln Ala Gly Gly Arg Leu Pro Arg Gly Asp Ala Ala Pro Ala Ser
    50                  55                  60

Thr Gly Ala Trp Val Gly Ala Trp Ala Thr Ala Pro Ala Ala Ala Glu
65                  70                  75                  80

Pro Gly Thr Glu Thr Thr Gly Leu Ala Gly Arg Ser Val Arg Asn Val
                85                  90                  95

Val His Thr Ser Val Gly Gly Thr Gly Ala Arg Ile Thr Leu Ser Asn
            100                 105                 110

Leu Tyr Gly Gln Ser Pro Leu Thr Val Thr His Ala Ser Ile Ala Leu
            115                 120                 125

Ala Ala Gly Pro Asp Thr Ala Ala Ile Ala Asp Thr Met Arg Arg
    130                 135                 140

Leu Thr Phe Gly Gly Ser Ala Arg Val Ile Ile Pro Ala Gly Gly Gln
145                 150                 155                 160

Val Met Ser Asp Thr Ala Arg Leu Ala Ile Pro Tyr Gly Ala Asn Val
                165                 170                 175

Leu Val Thr Thr Tyr Ser Pro Ile Pro Ser Gly Pro Val Thr Tyr His
            180                 185                 190

Pro Gln Ala Arg Gln Thr Ser Tyr Leu Ala Asp Gly Asp Arg Thr Ala
            195                 200                 205

Asp Val Thr Ala Val Ala Tyr Thr Thr Pro Thr Pro Tyr Trp Arg Tyr
    210                 215                 220

Leu Thr Ala Leu Asp Val Leu Ser His Glu Ala Asp Gly Thr Val Val
225                 230                 235                 240

Ala Phe Gly Asp Ser Ile Thr Asp Gly Ala Arg Ser Gln Ser Asp Ala
                245                 250                 255

Asn His Arg Trp Thr Asp Val Leu Ala Ala Arg Leu His Glu Ala Ala
            260                 265                 270

Gly Asp Gly Arg Asp Thr Pro Arg Tyr Ser Val Val Asn Glu Gly Ile
            275                 280                 285

Ser Gly Asn Arg Leu Leu Thr Ser Arg Pro Gly Arg Pro Ala Asp Asn
    290                 295                 300

Pro Ser Gly Leu Ser Arg Phe Gln Arg Asp Val Leu Glu Arg Thr Asn
305                 310                 315                 320

Val Lys Ala Val Val Val Leu Gly Val Asn Asp Val Leu Asn Ser
                325                 330                 335
```

Pro Glu Leu Ala Asp Arg Asp Ala Ile Leu Thr Gly Leu Arg Thr Leu
            340                 345                 350

Val Asp Arg Ala His Ala Arg Gly Leu Arg Val Val Gly Ala Thr Ile
            355                 360                 365

Thr Pro Phe Gly Gly Tyr Gly Gly Tyr Thr Glu Ala Arg Glu Thr Met
            370                 375                 380

Arg Gln Glu Val Asn Glu Glu Ile Arg Ser Gly Arg Val Phe Asp Thr
385                 390                 395                 400

Val Val Asp Phe Asp Lys Ala Leu Arg Asp Pro Tyr Asp Pro Arg Arg
                405                 410                 415

Met Arg Ser Asp Tyr Asp Ser Gly Asp His Leu His Pro Gly Asp Lys
            420                 425                 430

Gly Tyr Ala Arg Met Gly Ala Val Ile Asp Leu Ala Ala Leu Lys Gly
            435                 440                 445

Ala Ala Pro Val Lys Ala
            450

<210> SEQ ID NO 12
<211> LENGTH: 340
<212> TYPE: PRT
<213> ORGANISM: Streptomyces coelicolor

<400> SEQUENCE: 12

Met Thr Ser Met Ser Arg Ala Arg Val Ala Arg Ile Ala Ala Gly
1               5                   10                  15

Ala Ala Tyr Gly Gly Gly Gly Ile Gly Leu Ala Gly Ala Ala Val
            20                  25                  30

Gly Leu Val Val Ala Glu Val Gln Leu Ala Arg Arg Val Gly Val
            35                  40                  45

Gly Thr Pro Thr Arg Val Pro Asn Ala Gln Gly Leu Tyr Gly Gly Thr
            50                  55                  60

Leu Pro Thr Ala Gly Asp Pro Pro Leu Arg Leu Met Met Leu Gly Asp
65                  70                  75                  80

Ser Thr Ala Ala Gly Gln Gly Val His Arg Ala Gly Gln Thr Pro Gly
            85                  90                  95

Ala Leu Leu Ala Ser Gly Leu Ala Ala Val Ala Glu Arg Pro Val Arg
            100                 105                 110

Leu Gly Ser Val Ala Gln Pro Gly Ala Cys Ser Asp Asp Leu Asp Arg
            115                 120                 125

Gln Val Ala Leu Val Leu Ala Glu Pro Asp Arg Val Pro Asp Ile Cys
130                 135                 140

Val Ile Met Val Gly Ala Asn Asp Val Thr His Arg Met Pro Ala Thr
145                 150                 155                 160

Arg Ser Val Arg His Leu Ser Ser Ala Val Arg Arg Leu Arg Thr Ala
            165                 170                 175

Gly Ala Glu Val Val Val Gly Thr Cys Pro Asp Leu Gly Thr Ile Glu
            180                 185                 190

Arg Val Arg Gln Pro Leu Arg Trp Leu Ala Arg Ala Ser Arg Gln
            195                 200                 205

Leu Ala Ala Gln Thr Ile Gly Ala Val Glu Gln Gly Gly Arg Thr
            210                 215                 220

Val Ser Leu Gly Asp Leu Leu Gly Pro Glu Phe Ala Gln Asn Pro Arg
225                 230                 235                 240

Glu Leu Phe Gly Pro Asp Asn Tyr His Pro Ser Ala Glu Gly Tyr Ala

-continued

```
                         245                 250                 255
Thr Ala Ala Met Ala Val Leu Pro Ser Val Cys Ala Ala Leu Gly Leu
                260                 265                 270

Trp Pro Ala Asp Glu Glu His Pro Asp Ala Leu Arg Arg Glu Gly Phe
            275                 280                 285

Leu Pro Val Ala Arg Ala Ala Glu Ala Ala Ser Glu Ala Gly Thr
        290                 295                 300

Glu Val Ala Ala Ala Met Pro Thr Gly Pro Arg Gly Pro Trp Ala Leu
305                 310                 315                 320

Leu Lys Arg Arg Arg Arg Arg Val Ser Glu Ala Glu Pro Ser Ser
                325                 330                 335

Pro Ser Gly Val
            340

<210> SEQ ID NO 13
<211> LENGTH: 305
<212> TYPE: PRT
<213> ORGANISM: Streptomyces coelicolor

<400> SEQUENCE: 13

Met Gly Arg Gly Thr Asp Gln Arg Thr Arg Tyr Gly Arg Arg Ala
1               5                   10                  15

Arg Val Ala Leu Ala Ala Leu Thr Ala Ala Val Leu Gly Val Gly Val
                20                  25                  30

Ala Gly Cys Asp Ser Val Gly Gly Asp Ser Pro Ala Pro Ser Gly Ser
            35                  40                  45

Pro Ser Lys Arg Thr Arg Thr Ala Pro Ala Trp Asp Thr Ser Pro Ala
        50                  55                  60

Ser Val Ala Ala Val Gly Asp Ser Ile Thr Arg Gly Phe Asp Ala Cys
65                  70                  75                  80

Ala Val Leu Ser Asp Cys Pro Glu Val Ser Trp Ala Thr Gly Ser Ser
                85                  90                  95

Ala Lys Val Asp Ser Leu Ala Val Arg Leu Leu Gly Lys Ala Asp Ala
            100                 105                 110

Ala Glu His Ser Trp Asn Tyr Ala Val Thr Gly Ala Arg Met Ala Asp
        115                 120                 125

Leu Thr Ala Gln Val Thr Arg Ala Ala Gln Arg Glu Pro Glu Leu Val
130                 135                 140

Ala Val Met Ala Gly Ala Asn Asp Ala Cys Arg Ser Thr Thr Ser Ala
145                 150                 155                 160

Met Thr Pro Val Ala Asp Phe Arg Ala Gln Phe Glu Glu Ala Met Ala
                165                 170                 175

Thr Leu Arg Lys Lys Leu Pro Lys Ala Gln Val Tyr Val Ser Ser Ile
            180                 185                 190

Pro Asp Leu Lys Arg Leu Trp Ser Gln Gly Arg Thr Asn Pro Leu Gly
        195                 200                 205

Lys Gln Val Trp Lys Leu Gly Leu Cys Pro Ser Met Leu Gly Asp Ala
    210                 215                 220

Asp Ser Leu Asp Ser Ala Ala Thr Leu Arg Arg Asn Thr Val Arg Asp
225                 230                 235                 240

Arg Val Ala Asp Tyr Asn Glu Val Leu Arg Glu Val Cys Ala Lys Asp
                245                 250                 255

Arg Arg Cys Arg Ser Asp Asp Gly Ala Val His Glu Phe Arg Phe Gly
            260                 265                 270
```

```
Thr Asp Gln Leu Ser His Trp Asp Trp Phe His Pro Ser Val Asp Gly
            275                 280                 285

Gln Ala Arg Leu Ala Glu Ile Ala Tyr Arg Ala Val Thr Ala Lys Asn
    290                 295                 300

Pro
305

<210> SEQ ID NO 14
<211> LENGTH: 268
<212> TYPE: PRT
<213> ORGANISM: Streptomyces rimosus

<400> SEQUENCE: 14

Met Arg Leu Ser Arg Arg Ala Ala Thr Ala Ser Ala Leu Leu Leu Thr
1               5                   10                  15

Pro Ala Leu Ala Leu Phe Gly Ala Ser Ala Ala Val Ser Ala Pro Arg
            20                  25                  30

Ile Gln Ala Thr Asp Tyr Val Ala Leu Gly Asp Ser Tyr Ser Ser Gly
        35                  40                  45

Val Gly Ala Gly Ser Tyr Asp Ser Ser Gly Ser Cys Lys Arg Ser
    50                  55                  60

Thr Lys Ser Tyr Pro Ala Leu Trp Ala Ala Ser His Thr Gly Thr Arg
65                  70                  75                  80

Phe Asn Phe Thr Ala Cys Ser Gly Ala Arg Thr Gly Asp Val Leu Ala
                85                  90                  95

Lys Gln Leu Thr Pro Val Asn Ser Gly Thr Asp Leu Val Ser Ile Thr
            100                 105                 110

Ile Gly Gly Asn Asp Ala Gly Phe Ala Asp Thr Met Thr Thr Cys Asn
        115                 120                 125

Leu Gln Gly Glu Ser Ala Cys Leu Ala Arg Ile Ala Lys Ala Arg Ala
    130                 135                 140

Tyr Ile Gln Gln Thr Leu Pro Ala Gln Leu Asp Gln Val Tyr Asp Ala
145                 150                 155                 160

Ile Asp Ser Arg Ala Pro Ala Ala Gln Val Val Val Leu Gly Tyr Pro
                165                 170                 175

Arg Phe Tyr Lys Leu Gly Gly Ser Cys Ala Val Gly Leu Ser Glu Lys
            180                 185                 190

Ser Arg Ala Ala Ile Asn Ala Ala Asp Asp Ile Asn Ala Val Thr
    195                 200                 205

Ala Lys Arg Ala Ala Asp His Gly Phe Ala Phe Gly Asp Val Asn Thr
    210                 215                 220

Thr Phe Ala Gly His Glu Leu Cys Ser Gly Ala Pro Trp Leu His Ser
225                 230                 235                 240

Val Thr Leu Pro Val Glu Asn Ser Tyr His Pro Thr Ala Asn Gly Gln
                245                 250                 255

Ser Lys Gly Tyr Leu Pro Val Leu Asn Ser Ala Thr
            260                 265

<210> SEQ ID NO 15
<211> LENGTH: 336
<212> TYPE: PRT
<213> ORGANISM: Aeromonas salmonicida subsp.Salmonicida

<400> SEQUENCE: 15

Met Lys Lys Trp Phe Val Cys Leu Leu Gly Leu Ile Ala Leu Thr Val
1               5                   10                  15
```

Gln Ala Ala Asp Thr Arg Pro Ala Phe Ser Arg Ile Val Met Phe Gly
            20                  25                  30

Asp Ser Leu Ser Asp Thr Gly Lys Met Tyr Ser Lys Met Arg Gly Tyr
        35                  40                  45

Leu Pro Ser Ser Pro Tyr Tyr Glu Gly Arg Phe Ser Asn Gly Pro
    50                  55                  60

Val Trp Leu Glu Gln Leu Thr Lys Gln Phe Pro Gly Leu Thr Ile Ala
65                  70                  75                  80

Asn Glu Ala Glu Gly Gly Ala Thr Ala Val Ala Tyr Asn Lys Ile Ser
                85                  90                  95

Trp Asn Pro Lys Tyr Gln Val Ile Asn Asn Leu Asp Tyr Glu Val Thr
            100                 105                 110

Gln Phe Leu Gln Lys Asp Ser Phe Lys Pro Asp Asp Leu Val Ile Leu
        115                 120                 125

Trp Val Gly Ala Asn Asp Tyr Leu Ala Tyr Gly Trp Asn Thr Glu Gln
    130                 135                 140

Asp Ala Lys Arg Val Arg Asp Ala Ile Ser Asp Ala Ala Asn Arg Met
145                 150                 155                 160

Val Leu Asn Gly Ala Lys Gln Ile Leu Leu Phe Asn Leu Pro Asp Leu
                165                 170                 175

Gly Gln Asn Pro Ser Ala Arg Ser Gln Lys Val Val Glu Ala Val Ser
            180                 185                 190

His Val Ser Ala Tyr His Asn Lys Leu Leu Leu Asn Leu Ala Arg Gln
        195                 200                 205

Leu Ala Pro Thr Gly Met Val Lys Leu Phe Glu Ile Asp Lys Gln Phe
    210                 215                 220

Ala Glu Met Leu Arg Asp Pro Gln Asn Phe Gly Leu Ser Asp Val Glu
225                 230                 235                 240

Asn Pro Cys Tyr Asp Gly Gly Tyr Val Trp Lys Pro Phe Ala Thr Arg
                245                 250                 255

Ser Val Ser Thr Asp Arg Gln Leu Ser Ala Phe Ser Pro Gln Glu Arg
            260                 265                 270

Leu Ala Ile Ala Gly Asn Pro Leu Leu Ala Gln Ala Val Ala Ser Pro
        275                 280                 285

Met Ala Arg Arg Ser Ala Ser Pro Leu Asn Cys Glu Gly Lys Met Phe
    290                 295                 300

Trp Asp Gln Val His Pro Thr Thr Val Val His Ala Ala Leu Ser Glu
305                 310                 315                 320

Arg Ala Ala Thr Phe Ile Glu Thr Gln Tyr Glu Phe Leu Ala His Gly
                325                 330                 335

<210> SEQ ID NO 16
<211> LENGTH: 318
<212> TYPE: PRT
<213> ORGANISM: Aeromonas salmonicida

<400> SEQUENCE: 16

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
    50                  55                  60

Ala Glu Gly Gly Ala Thr Ala Val Ala Tyr Asn Lys Ile Ser Trp Asp
 65                  70                  75                  80

Pro Lys Tyr Gln Val Ile Asn Asn Leu Asp Tyr Glu Val Thr Gln Phe
                 85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
    290                 295                 300

Ala Thr Phe Ile Glu Thr Gln Tyr Glu Phe Leu Ala His Gly
305                 310                 315

<210> SEQ ID NO 17
<211> LENGTH: 465
<212> TYPE: PRT
<213> ORGANISM: Candida parapsilosis

<400> SEQUENCE: 17

Met Arg Tyr Phe Ala Ile Ala Phe Leu Leu Ile Asn Thr Ile Ser Ala
1               5                   10                  15

Phe Val Leu Ala Pro Lys Lys Pro Ser Gln Asp Asp Phe Tyr Thr Pro
            20                  25                  30

Pro Gln Gly Tyr Glu Ala Gln Pro Leu Gly Ser Ile Leu Lys Thr Arg
        35                  40                  45

Asn Val Pro Asn Pro Leu Thr Asn Val Phe Thr Pro Val Lys Val Gln
    50                  55                  60

Asn Ala Trp Gln Leu Leu Val Arg Ser Glu Thr Phe Gly Asn Pro
65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
            100                 105                 110

Ala Pro Ser Tyr Ala Ile Gln Tyr Gly Ser Asp Ile Ser Thr Leu Thr

```
            115                 120                 125
Thr Gln Gly Glu Met Tyr Tyr Ile Ser Ala Leu Leu Asp Gln Gly Tyr
    130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
            180                 185                 190

Trp Gly Tyr Ser Gly Ser Leu Ala Ser Gly Trp Ala Ala Ala Ile
        195                 200                 205

Gln Lys Glu Tyr Ala Pro Glu Leu Ser Lys Asn Leu Leu Gly Ala Ala
    210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
                245                 250                 255

Asn Glu Tyr Pro Asp Phe Lys Asn Tyr Leu Leu Lys Lys Val Ser Pro
            260                 265                 270

Leu Leu Ser Ile Thr Tyr Arg Leu Gly Asn Thr His Cys Leu Leu Asp
        275                 280                 285

Gly Gly Ile Ala Tyr Phe Gly Lys Ser Phe Ser Arg Ile Ile Arg
    290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
                325                 330                 335

Gln Ile Pro Leu Phe Ile Tyr His Gly Thr Leu Asp Ala Ile Val Pro
            340                 345                 350

Ile Val Asn Ser Arg Lys Thr Phe Gln Gln Trp Cys Asp Trp Gly Leu
        355                 360                 365

Lys Ser Gly Glu Tyr Asn Glu Asp Leu Thr Asn Gly His Ile Thr Glu
    370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
                405                 410                 415

Asn Leu Glu Tyr Pro Gly Thr Pro Gln Ser Ile Lys Asn Tyr Phe Glu
            420                 425                 430

Ala Ala Leu His Ala Ile Leu Gly Phe Asp Leu Gly Pro Asp Val Lys
        435                 440                 445

Arg Asp Lys Val Thr Leu Gly Gly Leu Leu Lys Leu Glu Arg Phe Ala
    450                 455                 460

Phe
465

<210> SEQ ID NO 18
<211> LENGTH: 471
<212> TYPE: PRT
<213> ORGANISM: Candida parapsilosis

<400> SEQUENCE: 18

Met Arg Tyr Phe Ala Ile Ala Phe Leu Leu Ile Asn Thr Ile Ser Ala
1               5                   10                  15
```

```
Phe Val Leu Ala Pro Lys Lys Pro Ser Gln Asp Asp Phe Tyr Thr Pro
                20                  25                  30

Pro Gln Gly Tyr Glu Ala Gln Pro Leu Gly Ser Ile Leu Lys Thr Arg
            35                  40                  45

Asn Val Pro Asn Pro Leu Thr Asn Val Phe Thr Pro Val Lys Val Gln
 50                  55                  60

Asn Ala Trp Gln Leu Leu Val Arg Ser Glu Asp Thr Phe Gly Asn Pro
 65                  70                  75                  80

Asn Ala Ile Val Thr Thr Ile Ile Gln Pro Phe Asn Ala Lys Lys Asp
                85                  90                  95

Lys Leu Val Ser Tyr Gln Thr Phe Glu Asp Ser Gly Lys Leu Asp Cys
                100                 105                 110

Ala Pro Ser Tyr Ala Ile Gln Tyr Gly Ser Asp Ile Ser Thr Leu Thr
            115                 120                 125

Thr Gln Gly Glu Met Tyr Tyr Ile Ser Ala Leu Leu Asp Gln Gly Tyr
 130                 135                 140

Tyr Val Val Thr Pro Asp Tyr Glu Gly Pro Lys Ser Thr Phe Thr Val
145                 150                 155                 160

Gly Leu Gln Ser Gly Arg Ala Thr Leu Asn Ser Leu Arg Ala Thr Leu
                165                 170                 175

Lys Ser Gly Asn Leu Thr Gly Val Ser Ser Asp Ala Glu Thr Leu Leu
                180                 185                 190

Trp Gly Tyr Ser Gly Gly Ser Leu Ala Ser Gly Trp Ala Ala Ala Ile
            195                 200                 205

Gln Lys Glu Tyr Ala Pro Glu Leu Ser Lys Asn Leu Leu Gly Ala Ala
 210                 215                 220

Leu Gly Gly Phe Val Thr Asn Ile Thr Ala Thr Ala Glu Ala Val Asp
225                 230                 235                 240

Ser Gly Pro Phe Ala Gly Ile Ile Ser Asn Ala Leu Ala Gly Ile Gly
            245                 250                 255

Asn Glu Tyr Pro Asp Phe Lys Asn Tyr Leu Leu Lys Lys Val Ser Pro
                260                 265                 270

Leu Leu Ser Ile Thr Tyr Arg Leu Gly Asn Thr His Cys Leu Leu Asp
                275                 280                 285

Gly Gly Ile Ala Tyr Phe Gly Lys Ser Phe Phe Ser Arg Ile Ile Arg
 290                 295                 300

Tyr Phe Pro Asp Gly Trp Asp Leu Val Asn Gln Glu Pro Ile Lys Thr
305                 310                 315                 320

Ile Leu Gln Asp Asn Gly Leu Val Tyr Gln Pro Lys Asp Leu Thr Pro
            325                 330                 335

Gln Ile Pro Leu Phe Ile Tyr His Gly Thr Leu Asp Ala Ile Val Pro
                340                 345                 350

Ile Val Asn Ser Arg Lys Thr Phe Gln Gln Trp Cys Asp Trp Gly Leu
                355                 360                 365

Lys Ser Gly Glu Tyr Asn Glu Asp Leu Thr Asn Gly His Ile Thr Glu
 370                 375                 380

Ser Ile Val Gly Ala Pro Ala Ala Leu Thr Trp Ile Ile Asn Arg Phe
385                 390                 395                 400

Asn Gly Gln Pro Pro Val Asp Gly Cys Gln His Asn Val Arg Ala Ser
            405                 410                 415

Asn Leu Glu Tyr Pro Gly Thr Pro Gln Ser Ile Lys Asn Tyr Phe Glu
                420                 425                 430

Ala Ala Leu His Ala Ile Leu Gly Phe Asp Leu Gly Pro Asp Val Lys
```

```
            435                 440                 445
Arg Asp Lys Val Thr Leu Gly Gly Leu Leu Lys Leu Glu Arg Phe Ala
    450                 455                 460

Phe His His His His His
465                 470

<210> SEQ ID NO 19
<211> LENGTH: 261
<212> TYPE: PRT
<213> ORGANISM: Streptomyces coelicolor

<400> SEQUENCE: 19

Met Ile Gly Ser Tyr Val Ala Val Gly Asp Ser Phe Thr Glu Gly Val
1               5                   10                  15

Gly Asp Pro Gly Pro Asp Gly Ala Phe Val Gly Trp Ala Asp Arg Leu
            20                  25                  30

Ala Val Leu Leu Ala Asp Arg Arg Pro Glu Gly Asp Phe Thr Tyr Thr
        35                  40                  45

Asn Leu Ala Val Arg Gly Arg Leu Leu Asp Gln Ile Val Ala Glu Gln
    50                  55                  60

Val Pro Arg Val Val Gly Leu Ala Pro Asp Leu Val Ser Phe Ala Ala
65                  70                  75                  80

Gly Gly Asn Asp Ile Ile Arg Pro Gly Thr Asp Pro Asp Glu Val Ala
                85                  90                  95

Glu Arg Phe Glu Leu Ala Val Ala Ala Leu Thr Ala Ala Ala Gly Thr
            100                 105                 110

Val Leu Val Thr Thr Gly Phe Asp Thr Arg Gly Val Pro Val Leu Lys
        115                 120                 125

His Leu Arg Gly Lys Ile Ala Thr Tyr Asn Gly His Val Arg Ala Ile
130                 135                 140

Ala Asp Arg Tyr Gly Cys Pro Val Leu Asp Leu Trp Ser Leu Arg Ser
145                 150                 155                 160

Val Gln Asp Arg Arg Ala Trp Asp Ala Asp Arg Leu His Leu Ser Pro
                165                 170                 175

Glu Gly His Thr Arg Val Ala Leu Arg Ala Gly Gln Ala Leu Gly Leu
            180                 185                 190

Arg Val Pro Ala Asp Pro Asp Gln Pro Trp Pro Leu Pro Pro Arg
        195                 200                 205

Gly Thr Leu Asp Val Arg Asp Asp Val His Trp Ala Arg Glu Tyr
    210                 215                 220

Leu Val Pro Trp Ile Gly Arg Arg Leu Arg Gly Glu Ser Ser Gly Asp
225                 230                 235                 240

His Val Thr Ala Lys Gly Thr Leu Ser Pro Asp Ala Ile Lys Thr Arg
                245                 250                 255

Ile Ala Ala Val Ala
            260

<210> SEQ ID NO 20

<400> SEQUENCE: 20

000

<210> SEQ ID NO 21

<400> SEQUENCE: 21
```

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25
<211> LENGTH: 347
<212> TYPE: PRT
<213> ORGANISM: Aeromonas hydrophila

<400> SEQUENCE: 25

```
Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Ala Asp
            20                  25                  30

Ser Arg Pro Ala Phe Ser Arg Ile Val Met Phe Gly Asp Ser Leu Ser
        35                  40                  45

Asp Thr Gly Lys Met Tyr Ser Lys Met Arg Gly Tyr Leu Pro Ser Ser
    50                  55                  60

Pro Tyr Tyr Glu Gly Arg Phe Ser Asn Gly Pro Val Trp Leu Glu
65                  70                  75                  80

Gln Leu Thr Lys Gln Phe Pro Gly Leu Thr Ile Ala Asn Glu Ala Glu
                85                  90                  95

Gly Gly Ala Thr Ala Val Ala Tyr Asn Lys Ile Ser Trp Asn Pro Lys
            100                 105                 110

Tyr Gln Val Ile Asn Asn Leu Asp Tyr Glu Val Thr Gln Phe Leu Gln
        115                 120                 125

Lys Asp Ser Phe Lys Pro Asp Asp Leu Val Ile Leu Trp Val Gly Ala
    130                 135                 140

Asn Asp Tyr Leu Ala Tyr Gly Trp Asn Thr Glu Gln Asp Ala Lys Arg
145                 150                 155                 160

Val Arg Asp Ala Ile Ser Asp Ala Ala Asn Arg Met Val Leu Asn Gly
                165                 170                 175

Ala Lys Gln Ile Leu Leu Phe Asn Leu Pro Asp Leu Gly Gln Asn Pro
            180                 185                 190

Ser Ala Arg Ser Gln Lys Val Val Glu Ala Val Ser His Val Ser Ala
        195                 200                 205

Tyr His Asn Gln Leu Leu Leu Asn Leu Ala Arg Gln Leu Ala Pro Thr
    210                 215                 220

Gly Met Val Lys Leu Phe Glu Ile Asp Lys Gln Phe Ala Glu Met Leu
225                 230                 235                 240

Arg Asp Pro Gln Asn Phe Gly Leu Ser Asp Val Glu Asn Pro Cys Tyr
                245                 250                 255
```

```
Asp Gly Gly Tyr Val Trp Lys Pro Phe Ala Thr Arg Ser Val Ser Thr
            260                 265                 270

Asp Arg Gln Leu Ser Ala Phe Ser Pro Gln Glu Arg Leu Ala Ile Ala
        275                 280                 285

Gly Asn Pro Leu Leu Ala Gln Ala Val Ala Ser Pro Met Ala Arg Arg
    290                 295                 300

Ser Ala Ser Pro Leu Asn Cys Glu Gly Lys Met Phe Trp Asp Gln Val
305                 310                 315                 320

His Pro Thr Thr Val Val His Ala Leu Ser Glu Arg Ala Ala Thr
            325                 330                 335

Phe Ile Ala Asn Gln Tyr Glu Phe Leu Ala His
            340                 345
```

<210> SEQ ID NO 26
<211> LENGTH: 267
<212> TYPE: PRT
<213> ORGANISM: Streptomyces sp.

<400> SEQUENCE: 26

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
            85                  90                  95

Ala Leu Asn Ala Ser Thr Gly Leu Val Ser Ile Thr Ile Gly Gly Asn
        100                 105                 110

Asp Ala Gly Phe Ala Asp Ala Met Thr Thr Cys Val Thr Ser Ser Asp
    115                 120                 125

Ser Thr Cys Leu Asn Arg Leu Ala Thr Ala Thr Asn Tyr Ile Asn Thr
130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
            165                 170                 175

Ala Ser Asn Pro Trp Tyr Cys Leu Gly Leu Ser Asn Thr Lys Arg Ala
        180                 185                 190

Ala Ile Asn Thr Thr Ala Asp Thr Leu Asn Ser Val Ile Ser Ser Arg
    195                 200                 205

Ala Thr Ala His Gly Phe Arg Phe Gly Asp Val Arg Pro Thr Phe Asn
210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
            245                 250                 255

Tyr Leu Pro Val Leu Asn Ala Asn Ser Ser Thr
        260                 265
```

<210> SEQ ID NO 27

```
<211> LENGTH: 548
<212> TYPE: PRT
<213> ORGANISM: Thermobifida sp

<400> SEQUENCE: 27

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
            20                  25                  30

His Glu Thr Arg Pro Leu Arg Gly Arg Cys Gly Cys Gly Glu Arg Arg
        35                  40                  45

Val Pro Pro Leu Thr Leu Pro Gly Asp Gly Val Leu Cys Thr Thr Ser
    50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
    130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Arg Gly Arg Phe
                165                 170                 175

Val Gly Ser Gly Pro Arg Ala Ala Thr Arg Arg Arg Leu Phe Leu Gly
            180                 185                 190

Ile Pro Ala Leu Val Leu Val Thr Ala Leu Thr Leu Val Leu Ala Val
        195                 200                 205

Pro Thr Gly Arg Glu Thr Leu Trp Arg Met Trp Cys Glu Ala Thr Gln
    210                 215                 220

Asp Trp Cys Leu Gly Val Pro Val Asp Ser Arg Gly Gln Pro Ala Glu
225                 230                 235                 240

Asp Gly Glu Phe Leu Leu Leu Ser Pro Val Gln Ala Ala Thr Trp Gly
                245                 250                 255

Asn Tyr Tyr Ala Leu Gly Asp Ser Tyr Ser Ser Gly Asp Gly Ala Arg
            260                 265                 270

Asp Tyr Tyr Pro Gly Thr Ala Val Lys Gly Gly Cys Trp Arg Ser Ala
        275                 280                 285

Asn Ala Tyr Pro Glu Leu Val Ala Glu Ala Tyr Asp Phe Ala Gly His
    290                 295                 300

Leu Ser Phe Leu Ala Cys Ser Gly Gln Arg Gly Tyr Ala Met Leu Asp
305                 310                 315                 320

Ala Ile Asp Glu Val Gly Ser Gln Leu Asp Trp Asn Ser Pro His Thr
                325                 330                 335

Ser Leu Val Thr Ile Gly Ile Gly Gly Asn Asp Leu Gly Phe Ser Thr
            340                 345                 350

Val Leu Lys Thr Cys Met Val Arg Val Pro Leu Leu Asp Ser Lys Ala
        355                 360                 365

Cys Thr Asp Gln Glu Asp Ala Ile Arg Lys Arg Met Ala Lys Phe Glu
    370                 375                 380

Thr Thr Phe Glu Glu Leu Ile Ser Glu Val Arg Thr Arg Ala Pro Asp
```

```
             385                 390                 395                 400
Ala Arg Ile Leu Val Val Gly Tyr Pro Arg Ile Phe Pro Glu Glu Pro
                    405                 410                 415

Thr Gly Ala Tyr Tyr Thr Leu Thr Ala Ser Asn Gln Arg Trp Leu Asn
                    420                 425                 430

Glu Thr Ile Gln Glu Phe Asn Gln Gln Leu Ala Glu Val Ala Val
                    435                 440                 445

His Asp Glu Glu Ile Ala Ala Ser Gly Val Gly Ser Val Glu Phe
                    450                 455                 460

Val Asp Val Tyr His Ala Leu Asp Gly His Glu Ile Gly Ser Asp Glu
465                 470                 475                 480

Pro Trp Val Asn Gly Val Gln Leu Arg Asp Leu Ala Thr Gly Val Thr
                    485                 490                 495

Val Asp Arg Ser Thr Phe His Pro Asn Ala Ala Gly His Arg Ala Val
                    500                 505                 510

Gly Glu Arg Val Ile Glu Gln Ile Glu Thr Gly Pro Gly Arg Pro Leu
                    515                 520                 525

Tyr Ala Thr Phe Ala Val Val Ala Gly Ala Thr Val Asp Thr Leu Ala
                    530                 535                 540

Gly Glu Val Gly
545

<210> SEQ ID NO 28
<211> LENGTH: 372
<212> TYPE: PRT
<213> ORGANISM: Thermobifida sp.

<400> SEQUENCE: 28

Met Gly Ser Gly Pro Arg Ala Ala Thr Arg Arg Leu Phe Leu Gly
1                5                  10                  15

Ile Pro Ala Leu Val Leu Val Thr Ala Leu Thr Leu Val Leu Ala Val
                    20                  25                  30

Pro Thr Gly Arg Glu Thr Leu Trp Arg Met Trp Cys Glu Ala Thr Gln
                    35                  40                  45

Asp Trp Cys Leu Gly Val Pro Val Asp Ser Arg Gly Gln Pro Ala Glu
                    50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                    85                  90                  95

Asp Tyr Tyr Pro Gly Thr Ala Val Lys Gly Gly Cys Trp Arg Ser Ala
                    100                 105                 110

Asn Ala Tyr Pro Glu Leu Val Ala Glu Ala Tyr Asp Phe Ala Gly His
                    115                 120                 125

Leu Ser Phe Leu Ala Cys Ser Gly Gln Arg Gly Tyr Ala Met Leu Asp
                    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                    165                 170                 175

Val Leu Lys Thr Cys Met Val Arg Val Pro Leu Leu Asp Ser Lys Ala
                    180                 185                 190

Cys Thr Asp Gln Glu Asp Ala Ile Arg Lys Arg Met Ala Lys Phe Glu
                    195                 200                 205
```

```
Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
                275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
                340                 345                 350

Tyr Ala Thr Phe Ala Val Val Ala Gly Ala Thr Val Asp Thr Leu Ala
                355                 360                 365

Gly Glu Val Gly
        370

<210> SEQ ID NO 29
<211> LENGTH: 300
<212> TYPE: PRT
<213> ORGANISM: Corynebacterium efficiens

<400> SEQUENCE: 29

Met Arg Thr Thr Val Ile Ala Ala Ser Ala Leu Leu Leu Leu Ala Gly
1               5                   10                  15

Cys Ala Asp Gly Ala Arg Glu Glu Thr Ala Gly Ala Pro Pro Gly Glu
            20                  25                  30

Ser Ser Gly Gly Ile Arg Glu Glu Gly Ala Glu Ala Ser Thr Ser Ile
        35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205
```

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Gln Thr Asp Ala
                260                 265                 270

Tyr Pro Leu His Pro Thr Ser Ala Gly His Glu Ala Met Ala Ala Ala
                275                 280                 285

Val Arg Asp Ala Leu Gly Leu Glu Pro Val Gln Pro
                290                 295                 300

<210> SEQ ID NO 30
<211> LENGTH: 284
<212> TYPE: PRT
<213> ORGANISM: Novosphingobium aromaticivorans

<400> SEQUENCE: 30

Met Gly Gln Val Lys Leu Phe Ala Arg Arg Cys Ala Pro Val Leu Leu
1               5                   10                  15

Ala Leu Ala Gly Leu Ala Pro Ala Ala Thr Val Ala Arg Glu Ala Pro
                20                  25                  30

Leu Ala Glu Gly Ala Arg Tyr Val Ala Leu Gly Ser Ser Phe Ala Ala
                35                  40                  45

Gly Pro Gly Val Gly Pro Asn Ala Pro Gly Ser Pro Glu Arg Cys Gly
        50                  55                  60

Arg Gly Thr Leu Asn Tyr Pro His Leu Leu Ala Glu Ala Leu Lys Leu
65                  70                  75                  80

Asp Leu Val Asp Ala Thr Cys Ser Gly Ala Thr Thr His His Val Leu
                85                  90                  95

Gly Pro Trp Asn Glu Val Pro Pro Gln Ile Asp Ser Val Asn Gly Asp
                100                 105                 110

Thr Arg Leu Val Thr Leu Thr Ile Gly Gly Asn Asp Val Ser Phe Val
                115                 120                 125

Gly Asn Ile Phe Ala Ala Ala Cys Glu Lys Met Ala Ser Pro Asp Pro
        130                 135                 140

Arg Cys Gly Lys Trp Arg Glu Ile Thr Glu Glu Trp Gln Ala Asp
145                 150                 155                 160

Glu Glu Arg Met Arg Ser Ile Val Arg Gln Ile His Ala Arg Ala Pro
                165                 170                 175

Leu Ala Arg Val Val Val Asp Tyr Ile Thr Val Leu Pro Pro Ser
                180                 185                 190

Gly Thr Cys Ala Ala Met Ala Ile Ser Pro Asp Arg Leu Ala Gln Ser
                195                 200                 205

Arg Ser Ala Ala Lys Arg Leu Arg Ile Thr Ala Arg Val Ala Arg
        210                 215                 220

Glu Glu Gly Ala Ser Leu Leu Lys Phe Ser His Ile Ser Arg Arg His
225                 230                 235                 240

His Pro Cys Ser Ala Lys Pro Trp Ser Asn Gly Leu Ser Ala Pro Ala
                245                 250                 255

Asp Asp Gly Ile Pro Val His Pro Asn Arg Leu Gly His Ala Glu Ala
                260                 265                 270

Ala Ala Ala Leu Val Lys Leu Val Lys Leu Met Lys

<210> SEQ ID NO 31
<211> LENGTH: 268
<212> TYPE: PRT
<213> ORGANISM: Streptomyces coelicolor

<400> SEQUENCE: 31

Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205

Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
                245                 250                 255

Ser Gly Gly Tyr Leu Pro Val Leu Asn Gly Ala Ala
            260                 265

<210> SEQ ID NO 32
<211> LENGTH: 269
<212> TYPE: PRT
<213> ORGANISM: Streptomyces avermitilis

<400> SEQUENCE: 32

Met Arg Arg Ser Arg Ile Thr Ala Tyr Val Thr Ser Leu Leu Leu Ala
1               5                   10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser

```
Ser Lys Ala Tyr Pro Tyr Leu Trp Gln Ala Ala His Ser Pro Ser Ser
 65                  70                  75                  80

Phe Ser Phe Met Ala Cys Ser Gly Ala Arg Thr Gly Asp Val Leu Ala
                 85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265

<210> SEQ ID NO 33
<211> LENGTH: 267
<212> TYPE: PRT
<213> ORGANISM: Streptomyces sp.

<400> SEQUENCE: 33

Met Arg Leu Thr Arg Ser Leu Ser Ala Ala Ser Val Ile Val Phe Ala
 1               5                  10                  15

Leu Leu Leu Ala Leu Leu Gly Ile Ser Pro Ala Gln Ala Ala Gly Pro
                20                  25                  30

Ala Tyr Val Ala Leu Gly Asp Ser Tyr Ser Ser Gly Asn Gly Ala Gly
             35                  40                  45

Ser Tyr Ile Asp Ser Ser Gly Asp Cys His Arg Ser Asn Asn Ala Tyr
     50                  55                  60

Pro Ala Arg Trp Ala Ala Ala Asn Ala Pro Ser Ser Phe Thr Phe Ala
 65                  70                  75                  80

Ala Cys Ser Gly Ala Val Thr Thr Asp Val Ile Asn Asn Gln Leu Gly
                 85                  90                  95

Ala Leu Asn Ala Ser Thr Gly Leu Val Ser Ile Thr Ile Gly Gly Asn
            100                 105                 110

Asp Ala Gly Phe Ala Asp Ala Met Thr Thr Cys Val Thr Ser Ser Asp
        115                 120                 125

Ser Thr Cys Leu Asn Arg Leu Ala Thr Ala Thr Asn Tyr Ile Asn Thr
    130                 135                 140

Thr Leu Leu Ala Arg Leu Asp Ala Val Tyr Ser Gln Ile Lys Ala Arg
145                 150                 155                 160
```

```
Ala Pro Asn Ala Arg Val Val Leu Gly Tyr Pro Arg Met Tyr Leu
            165                 170                 175

Ala Ser Asn Pro Trp Tyr Cys Leu Gly Leu Ser Asn Thr Lys Arg Ala
        180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
        210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
                260                 265

<210> SEQ ID NO 34
<211> LENGTH: 317
<212> TYPE: PRT
<213> ORGANISM: Aeromonas hydrophila

<400> SEQUENCE: 34

Ala Asp Ser Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Asn Glu Phe Pro Gly Leu Thr Ile Ala Asn Glu
50                  55                  60

Ala Glu Gly Gly Pro Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
        130                 135                 140

Asn Gly Ala Lys Glu Ile Leu Leu Phe Asn Leu Pro Asp Leu Gly Gln
145                 150                 155                 160

Asn Pro Ser Ala Arg Ser Gln Lys Val Val Glu Ala Ala Ser His Val
                165                 170                 175

Ser Ala Tyr His Asn Gln Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Gln Arg Asn Ala
210                 215                 220

Cys Tyr Gly Gly Ser Tyr Val Trp Lys Pro Phe Ala Ser Arg Ser Ala
225                 230                 235                 240

Ser Thr Asp Ser Gln Leu Ser Ala Phe Asn Pro Gln Glu Arg Leu Ala
                245                 250                 255

Ile Ala Gly Asn Pro Leu Leu Ala Gln Ala Val Ala Ser Pro Met Ala
            260                 265                 270
```

```
Ala Arg Ser Ala Ser Thr Leu Asn Cys Glu Gly Lys Met Phe Trp Asp
        275                 280                 285

Gln Val His Pro Thr Thr Val Val His Ala Ala Leu Ser Glu Pro Ala
290                 295                 300

Ala Thr Phe Ile Glu Ser Gln Tyr Glu Phe Leu Ala His
305                 310                 315

<210> SEQ ID NO 35
<211> LENGTH: 318
<212> TYPE: PRT
<213> ORGANISM: Aeromonas salmonicida

<400> SEQUENCE: 35

Ala Asp Thr Arg Pro Ala Phe Ser Arg Ile Val Met Phe Gly Asp Ser
1               5                   10                  15

Leu Ser Asp Thr Gly Lys Met Tyr Ser Lys Met Arg Gly Tyr Leu Pro
            20                  25                  30

Ser Ser Pro Pro Tyr Tyr Glu Gly Arg Phe Ser Asn Gly Pro Val Trp
        35                  40                  45

Leu Glu Gln Leu Thr Lys Gln Phe Pro Gly Leu Thr Ile Ala Asn Glu
50                  55                  60

Ala Glu Gly Gly Ala Thr Ala Val Ala Tyr Asn Lys Ile Ser Trp Asn
65                  70                  75                  80

Pro Lys Tyr Gln Val Ile Asn Asn Leu Asp Tyr Glu Val Thr Gln Phe
                85                  90                  95

Leu Gln Lys Asp Ser Phe Lys Pro Asp Asp Leu Val Ile Leu Trp Val
            100                 105                 110

Gly Ala Asn Asp Tyr Leu Ala Tyr Gly Trp Asn Thr Glu Gln Asp Ala
        115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Leu Asn Leu Ala Arg Gln Leu Ala
            180                 185                 190

Pro Thr Gly Met Val Lys Leu Phe Glu Ile Asp Lys Gln Phe Ala Glu
        195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
        275                 280                 285

Gln Val His Pro Thr Thr Val Val His Ala Ala Leu Ser Glu Arg Ala
290                 295                 300

Ala Thr Phe Ile Glu Thr Gln Tyr Glu Phe Leu Ala His Gly
305                 310                 315
```

<210> SEQ ID NO 36
<211> LENGTH: 1371
<212> TYPE: DNA
<213> ORGANISM: Streptomyces thermosacchari

<400> SEQUENCE: 36

```
acaggccgat gcacggaacc gtacctttcc gcagtgaagc gctctccccc catcgttcgc    60
cgggacttca tccgcgattt tggcatgaac acttccttca acgcgcgtag cttgctacaa   120
gtgcggcagc agacccgctc gttggaggct cagtgagatt gacccgatcc ctgtcggccg   180
catccgtcat cgtcttcgcc ctgctgctcg cgctgctggg catcagcccg cccaggcag    240
ccggcccggc ctatgtggcc ctgggggatt cctattcctc gggcaacggc gccggaagtt   300
acatcgattc gagcggtgac tgtcaccgca gcaacaacgc gtaccccgcc cgctgggcgg   360
cggccaacgc accgtcctcc ttcaccttcg cggcctgctc gggagcggtg accacggatg   420
tgatcaacaa tcagctgggc gccctcaacg cgtccaccgg cctggtgagc atcaccatcg   480
gcggcaatga cgcgggcttc gcggacgcga tgacccctg cgtcaccagc tcggacagca   540
cctgcctcaa ccggctggcc accgccacca actacatcaa caccaccctg ctcgcccggc   600
tcgacgcggt ctacagccag atcaaggccc gtgcccccaa cgcccgcgtg gtcgtcctcg   660
gctacccgcg catgtacctg gcctcgaacc cctggtactg cctgggcctg agcaacacca   720
agcgcgcggc catcaacacc accgccgaca ccctcaactc ggtgatctcc tcccgggcca   780
ccgcccacgg attccgattc ggcgatgtcc gcccgacctt caacaaccac gaactgttct   840
tcggcaacga ctggctgcac tcactcaccc tgccggtgtg ggagtcgtac cacccccacca   900
gcacgggcca tcagagcggc tatctgccgg tcctcaacgc caacagctcg acctgatcaa   960
cgcacggccg tgcccgcccc gcgcgtcacg ctcggcgcgg gcgccgcagc gcgttgatca  1020
gcccacagtg ccggtgacgg tcccaccgtc acggtcgagg gtgtacgtca cggtggcgcc  1080
gctccagaag tggaacgtca gcaggaccgt ggagccgtcc ctgacctcgt cgaagaactc  1140
cggggtcagc gtgatcaccc ctcccccgta gccggggggcg aaggcggcgc cgaactcctt  1200
gtaggacgtc cagtcgtgcg gcccggcgtt gccaccgtcc gcgtagaccg cttccatggt  1260
cgccagccgg tccccgcgga actcggtggg gatgtccgtg cccaaggtgg tcccggtggt  1320
gtccgagagc accgggggct cgtaccggat gatgtgcaga tccaaagaat t            1371
```

<210> SEQ ID NO 37
<211> LENGTH: 267
<212> TYPE: PRT
<213> ORGANISM: Streptomyces thermosacchari

<400> SEQUENCE: 37

```
Met Arg Leu Thr Arg Ser Leu Ser Ala Ala Ser Val Ile Val Phe Ala
1               5                   10                  15

Leu Leu Leu Ala Leu Leu Gly Ile Ser Pro Ala Gln Ala Ala Gly Pro
            20                  25                  30

Ala Tyr Val Ala Leu Gly Asp Ser Tyr Ser Ser Gly Asn Gly Ala Gly
        35                  40                  45

Ser Tyr Ile Asp Ser Ser Gly Asp Cys His Arg Ser Asn Asn Ala Tyr
    50                  55                  60

Pro Ala Arg Trp Ala Ala Ala Asn Ala Pro Ser Ser Phe Thr Phe Ala
65                  70                  75                  80

Ala Cys Ser Gly Ala Val Thr Thr Asp Val Ile Asn Asn Gln Leu Gly
                85                  90                  95
```

```
Ala Leu Asn Ala Ser Thr Gly Leu Val Ser Ile Thr Ile Gly Gly Asn
                100                 105                 110

Asp Ala Gly Phe Ala Asp Ala Met Thr Thr Cys Val Thr Ser Ser Asp
            115                 120                 125

Ser Thr Cys Leu Asn Arg Leu Ala Thr Ala Thr Asn Tyr Ile Asn Thr
        130                 135                 140

Thr Leu Leu Ala Arg Leu Asp Ala Val Tyr Ser Gln Ile Lys Ala Arg
145                 150                 155                 160

Ala Pro Asn Ala Arg Val Val Val Leu Gly Tyr Pro Arg Met Tyr Leu
                165                 170                 175

Ala Ser Asn Pro Trp Tyr Cys Leu Gly Leu Ser Asn Thr Lys Arg Ala
            180                 185                 190

Ala Ile Asn Thr Thr Ala Asp Thr Leu Asn Ser Val Ile Ser Ser Arg
        195                 200                 205

Ala Thr Ala His Gly Phe Arg Phe Gly Asp Val Arg Pro Thr Phe Asn
210                 215                 220

Asn His Glu Leu Phe Phe Gly Asn Asp Trp Leu His Ser Leu Thr Leu
225                 230                 235                 240

Pro Val Trp Glu Ser Tyr His Pro Thr Ser Thr Gly His Gln Ser Gly
                245                 250                 255

Tyr Leu Pro Val Leu Asn Ala Asn Ser Ser Thr
            260                 265

<210> SEQ ID NO 38
<211> LENGTH: 548
<212> TYPE: PRT
<213> ORGANISM: Thermobifida fusca

<400> SEQUENCE: 38

Met Leu Pro His Pro Ala Gly Glu Arg Gly Glu Val Gly Ala Phe Phe
1               5                   10                  15

Ala Leu Leu Val Gly Thr Pro Gln Asp Arg Arg Leu Arg Leu Glu Cys
                20                  25                  30

His Glu Thr Arg Pro Leu Arg Gly Arg Cys Gly Cys Gly Glu Arg Arg
            35                  40                  45

Val Pro Pro Leu Thr Leu Pro Gly Asp Gly Val Leu Cys Thr Thr Ser
        50                  55                  60

Ser Thr Arg Asp Ala Glu Thr Val Trp Arg Lys His Leu Gln Pro Arg
65                  70                  75                  80

Pro Asp Gly Gly Phe Arg Pro His Leu Gly Val Gly Cys Leu Leu Ala
                85                  90                  95

Gly Gln Gly Ser Pro Gly Val Leu Trp Cys Gly Arg Glu Gly Cys Arg
            100                 105                 110

Phe Glu Val Cys Arg Arg Asp Thr Pro Gly Leu Ser Arg Thr Arg Asn
        115                 120                 125

Gly Asp Ser Ser Pro Pro Phe Arg Ala Gly Trp Ser Leu Pro Pro Lys
130                 135                 140

Cys Gly Glu Ile Ser Gln Ser Ala Arg Lys Thr Pro Ala Val Pro Arg
145                 150                 155                 160

Tyr Ser Leu Leu Arg Thr Asp Arg Pro Asp Gly Pro Gly Arg Phe
                165                 170                 175

Val Gly Ser Gly Pro Arg Ala Ala Thr Arg Arg Leu Phe Leu Gly
            180                 185                 190

Ile Pro Ala Leu Val Leu Val Thr Ala Leu Thr Leu Val Leu Ala Val
        195                 200                 205
```

```
Pro Thr Gly Arg Glu Thr Leu Trp Arg Met Trp Cys Glu Ala Thr Gln
    210                 215                 220
Asp Trp Cys Leu Gly Val Pro Val Asp Ser Arg Gly Gln Pro Ala Glu
225                 230                 235                 240
Asp Gly Glu Phe Leu Leu Leu Ser Pro Val Gln Ala Ala Thr Trp Gly
                245                 250                 255
Asn Tyr Tyr Ala Leu Gly Asp Ser Tyr Ser Ser Gly Asp Gly Ala Arg
            260                 265                 270
Asp Tyr Tyr Pro Gly Thr Ala Val Lys Gly Gly Cys Trp Arg Ser Ala
        275                 280                 285
Asn Ala Tyr Pro Glu Leu Val Ala Glu Ala Tyr Asp Phe Ala Gly His
    290                 295                 300
Leu Ser Phe Leu Ala Cys Ser Gly Gln Arg Gly Tyr Ala Met Leu Asp
305                 310                 315                 320
Ala Ile Asp Glu Val Gly Ser Gln Leu Asp Trp Asn Ser Pro His Thr
                325                 330                 335
Ser Leu Val Thr Ile Gly Ile Gly Gly Asn Asp Leu Gly Phe Ser Thr
            340                 345                 350
Val Leu Lys Thr Cys Met Val Arg Val Pro Leu Leu Asp Ser Lys Ala
        355                 360                 365
Cys Thr Asp Gln Glu Asp Ala Ile Arg Lys Arg Met Ala Lys Phe Glu
    370                 375                 380
Thr Thr Phe Glu Glu Leu Ile Ser Glu Val Arg Thr Arg Ala Pro Asp
385                 390                 395                 400
Ala Arg Ile Leu Val Val Gly Tyr Pro Arg Ile Phe Pro Glu Glu Pro
                405                 410                 415
Thr Gly Ala Tyr Tyr Thr Leu Thr Ala Ser Asn Gln Arg Trp Leu Asn
            420                 425                 430
Glu Thr Ile Gln Glu Phe Asn Gln Gln Leu Ala Glu Ala Val Ala Val
        435                 440                 445
His Asp Glu Glu Ile Ala Ala Ser Gly Gly Val Gly Ser Val Glu Phe
    450                 455                 460
Val Asp Val Tyr His Ala Leu Asp Gly His Glu Ile Gly Ser Asp Glu
465                 470                 475                 480
Pro Trp Val Asn Gly Val Gln Leu Arg Asp Leu Ala Thr Gly Val Thr
                485                 490                 495
Val Asp Arg Ser Thr Phe His Pro Asn Ala Ala Gly His Arg Ala Val
            500                 505                 510
Gly Glu Arg Val Ile Glu Gln Ile Glu Thr Gly Pro Gly Arg Pro Leu
        515                 520                 525
Tyr Ala Thr Phe Ala Val Val Ala Gly Ala Thr Val Asp Thr Leu Ala
    530                 535                 540
Gly Glu Val Gly
545

<210> SEQ ID NO 39
<211> LENGTH: 3000
<212> TYPE: DNA
<213> ORGANISM: Thermobifida fusca

<400> SEQUENCE: 39
ggtggtgaac cagaacaccc ggtcgtcggc gtgggcgtcc aggtgcaggt gcaggttctt      60
caactgctcc agcaggatgc cgccgtggcc gtgcacgatg ccttgggca ggcctgtggt      120
```

| | |
|---|---|
| ccccgacgag tacagcaccc atagcggatg gtcgaacggc agcggggtga actccagttc | 180 |
| cgcgccttcg cccgcggctt cgaactccgc ccaggacagg gtgtcggcga cagggccgca | 240 |
| gcccaggtac ggcaggacga cggtgtgctg caggctgggc atgccgtcgc gcagggcttt | 300 |
| gagcacgtca cggcggtcga agtccttacc gccgtagcgg tagccgtcca cggccagcag | 360 |
| cactttcggt tcgatctgcg cgaaccggtc gaggacgctg cgcaccccga agtcggggga | 420 |
| acaggacgac caggtcgcac cgatcgcggc gcaggcgagg aatgcggccg tcgcctcggc | 480 |
| gatgttcggc aggtaggcca cgacccggtc gccggggccc accccgaggc tgcggagggc | 540 |
| cgcagcgatc gcggcggtgc gggtccgcag ttctccccag gtccactcgg tcaacgccg | 600 |
| gagttcggac gcgtgccgga tcgccacggc tgatgggtca cggtcgcgga agatgtgctc | 660 |
| ggcgtagttg agggtggcgc cggggaacca cacggcgccg gcatggcgt cggaggcgag | 720 |
| cactgtggtg tacggggtgg cggcgcgcac ccggtagtac tcccagatcg cggaccagaa | 780 |
| tccttcgagg tcggttaccg accagcgcca cagtgcctcg tagtccggtg cgtccacacc | 840 |
| gcggtgctcc cgcacccagc gggtgaacgc ggtgaggttg cgcgcttctt tgcgctcctc | 900 |
| gtcgggactc cacaggatcg gcggctgcgg cttgagtgtc atgaaacgcg accccttcgt | 960 |
| ggacggtgcg gatgcggtga gcgtcggtg cctcccctaa cgctccccgg tgacggagtg | 1020 |
| ttgtgcacca catctagcac gcgggacgcg gaaaccgtat ggagaaaaca cctacaaccc | 1080 |
| cggccggacg gtgggtttcg gccacactta ggggtcgggt gcctgcttgc cgggcagggc | 1140 |
| agtcccgggg tgctgtggtg cgggcgggag ggctgtcgct tcgaggtgtg ccggcgggac | 1200 |
| actccgggcc tcagccgtac ccgcaacggg gacagttctc ctcccttccg ggctggatgg | 1260 |
| tcccttcccc cgaaatgcgg cgagatctcc cagtcagccc ggaaaacacc cgctgtgccc | 1320 |
| aggtactctt tgcttcgaac agacaggcg gacggtccac gggggaggtt tgtgggcagc | 1380 |
| ggaccacgtg cggcgaccag acgacggttg ttcctcggta tccccgctct tgtacttgtg | 1440 |
| acagcgctca cgctggtctt ggctgtcccg acggggcgcg agacgctgtg gcgcatgtgg | 1500 |
| tgtgaggcca cccaggactg gtgcctgggg gtgccggtcg actcccgcgg acagcctgcg | 1560 |
| gaggacggcg agtttctgct gctttctccg gtccaggcag cgacctgggg gaactattac | 1620 |
| gcgctcgggg attcgtactc ttcggggac ggggcccgcg actactatcc cggcaccgcg | 1680 |
| gtgaagggcg gttgctggcg gtccgctaac gccatccgg agctggtcgc cgaagcctac | 1740 |
| gacttcgccg gacacttgtc gttcctggcc tgcagcggcc agcgcggcta cgccatgctt | 1800 |
| gacgctatcg acgaggtcgg ctcgcagctg gactggaact cccctcacac gtcgctggtg | 1860 |
| acgatcggga tcggcggcaa cgatctgggg ttctccacgg ttttgaagac ctgcatggtg | 1920 |
| cgggtgccgc tgctggacag caaggcgtgc acggaccagg aggacgctat ccgcaagcgg | 1980 |
| atggcgaaat tcgagacgac gtttgaagag ctcatcagcg aagtgcgcac ccgcgcgccg | 2040 |
| gacgcccgga tccttgtcgt gggctacccc cggattttc cggaggaacc gaccggcgcc | 2100 |
| tactacacgc tgaccgcgag caaccagcgg tggctcaacg aaaccattca ggagttcaac | 2160 |
| cagcagctcg ccgaggctgt cgcggtccac gacgaggaga ttgccgcgtc gggcggggtg | 2220 |
| ggcagcgtga agttcgtgga cgtctaccac gcgttggacg gccacgagat cggctcggac | 2280 |
| gagccgtggg tgaacggggt gcagttgcgg gacctcgcca ccggggtgac tgtggaccgc | 2340 |
| agtaccttcc accccaacgc cgctgggcac cgggcggtcg gtgagcgggt catcgagcag | 2400 |
| atcgaaaccg gccgggccg tccgctctat gccactttcg cggtggtggc gggggcgacc | 2460 |
| gtggacactc tcgcgggcga ggtggggtga cccggcttac cgtccggccc gcaggtctgc | 2520 |

```
gagcactgcg gcgatctggt ccactgccca gtgcagttcg tcttcggtga tgaccagcgg    2580
cggggagagc cggatcgttg agccgtgcgt gtctttgacg agcacacccc gctgcaggag    2640
ccgttcgcac agttctcttc cggtggccag agtcgggtcg acgtcgatcc cagcccacag    2700
gccgatgctg cgggccgcga ccacgccgtt gccgaccagt tggtcgaggc gggcgcgcag    2760 cacggggggcg agggcgcgga catggtccag gtaagggccg tcgcggacga ggctcaccac    2820
ggcagtgccg accgcgcagg cgagggcgtt gccgccgaag tgctgccgt gctggccggg     2880 gcggatcacg tcgaagactt ccgcgtcgcc taccgccgcc gccacgggca ggatgccgcc    2940
gcccagcgct ttgccgaaca ggtagatatc ggcgtcgact ccgctgtggt cgcaggcccg    3000
```

<210> SEQ ID NO 40
<211> LENGTH: 372
<212> TYPE: PRT
<213> ORGANISM: Thermobifida fusca

<400> SEQUENCE: 40

```
Val Gly Ser Gly Pro Arg Ala Ala Thr Arg Arg Leu Phe Leu Gly
 1               5                  10                  15

Ile Pro Ala Leu Val Leu Val Thr Ala Leu Thr Leu Val Leu Ala Val
                20                  25                  30

Pro Thr Gly Arg Glu Thr Leu Trp Arg Met Trp Cys Glu Ala Thr Gln
            35                  40                  45

Asp Trp Cys Leu Gly Val Pro Val Asp Ser Arg Gly Gln Pro Ala Glu
        50                  55                  60

Asp Gly Glu Phe Leu Leu Leu Ser Pro Val Gln Ala Ala Thr Trp Gly
65                  70                  75                  80

Asn Tyr Tyr Ala Leu Gly Asp Ser Tyr Ser Ser Gly Asp Gly Ala Arg
                85                  90                  95

Asp Tyr Tyr Pro Gly Thr Ala Val Lys Gly Gly Cys Trp Arg Ser Ala
            100                 105                 110

Asn Ala Tyr Pro Glu Leu Val Ala Glu Ala Tyr Asp Phe Ala Gly His
        115                 120                 125

Leu Ser Phe Leu Ala Cys Ser Gly Gln Arg Gly Tyr Ala Met Leu Asp
    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                165                 170                 175

Val Leu Lys Thr Cys Met Val Arg Val Pro Leu Leu Asp Ser Lys Ala
            180                 185                 190

Cys Thr Asp Gln Glu Asp Ala Ile Arg Lys Arg Met Ala Lys Phe Glu
        195                 200                 205

Thr Thr Phe Glu Glu Leu Ile Ser Glu Val Arg Thr Arg Ala Pro Asp
    210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                245                 250                 255

Glu Thr Ile Gln Glu Phe Asn Gln Gln Leu Ala Glu Ala Val Ala Val
            260                 265                 270

His Asp Glu Glu Ile Ala Ala Ser Gly Gly Val Gly Ser Val Glu Phe
        275                 280                 285
```

```
Val Asp Val Tyr His Ala Leu Asp Gly His Glu Ile Gly Ser Asp Glu
    290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                325                 330                 335

Gly Glu Arg Val Ile Glu Gln Ile Glu Thr Gly Pro Gly Arg Pro Leu
            340                 345                 350

Tyr Ala Thr Phe Ala Val Val Ala Gly Ala Thr Val Asp Thr Leu Ala
        355                 360                 365

Gly Glu Val Gly
    370

<210> SEQ ID NO 41
<211> LENGTH: 300
<212> TYPE: PRT
<213> ORGANISM: Corynebacterium efficiens

<400> SEQUENCE: 41

Met Arg Thr Thr Val Ile Ala Ala Ser Ala Leu Leu Leu Leu Ala Gly
1               5                   10                  15

Cys Ala Asp Gly Ala Arg Glu Glu Thr Ala Gly Ala Pro Pro Gly Glu
            20                  25                  30

Ser Ser Gly Gly Ile Arg Glu Glu Gly Ala Glu Ala Ser Thr Ser Ile
        35                  40                  45

Thr Asp Val Tyr Ile Ala Leu Gly Asp Ser Tyr Ala Ala Met Gly Gly
    50                  55                  60

Arg Asp Gln Pro Leu Arg Gly Glu Pro Phe Cys Leu Arg Ser Ser Gly
65                  70                  75                  80

Asn Tyr Pro Glu Leu Leu His Ala Glu Val Thr Asp Leu Thr Cys Gln
                85                  90                  95

Gly Ala Val Thr Gly Asp Leu Leu Glu Pro Arg Thr Leu Gly Glu Arg
            100                 105                 110

Thr Leu Pro Ala Gln Val Asp Ala Leu Thr Glu Asp Thr Thr Leu Val
        115                 120                 125

Thr Leu Ser Ile Gly Gly Asn Asp Leu Gly Phe Gly Glu Val Ala Gly
    130                 135                 140

Cys Ile Arg Glu Arg Ile Ala Gly Glu Asn Ala Asp Asp Cys Val Asp
145                 150                 155                 160

Leu Leu Gly Glu Thr Ile Gly Glu Gln Leu Asp Gln Leu Pro Pro Gln
                165                 170                 175

Leu Asp Arg Val His Glu Ala Ile Arg Asp Arg Ala Gly Asp Ala Gln
            180                 185                 190

Val Val Val Thr Gly Tyr Leu Pro Leu Val Ser Ala Gly Asp Cys Pro
        195                 200                 205

Glu Leu Gly Asp Val Ser Glu Ala Asp Arg Arg Trp Ala Val Glu Leu
    210                 215                 220

Thr Gly Gln Ile Asn Glu Thr Val Arg Glu Ala Ala Glu Arg His Asp
225                 230                 235                 240

Ala Leu Phe Val Leu Pro Asp Asp Ala Asp Glu His Thr Ser Cys Ala
                245                 250                 255

Pro Pro Gln Gln Arg Trp Ala Asp Ile Gln Gly Gln Gln Thr Asp Ala
            260                 265                 270

Tyr Pro Leu His Pro Thr Ser Ala Gly His Glu Ala Met Ala Ala Ala
        275                 280                 285
```

```
Val Arg Asp Ala Leu Gly Leu Glu Pro Val Gln Pro
    290                 295                 300

<210> SEQ ID NO 42
<211> LENGTH: 3000
<212> TYPE: DNA
<213> ORGANISM: Corynebacterium efficiens

<400> SEQUENCE: 42
ttctggggtg ttatgggggtt gttatcggct cgtcctgggt ggatcccgcc aggtgggta       60 ttcacggggg acttttgtgt ccaacagccg agaatgagtg ccctgagcgg tgggaatgag      120
gtgggcgggg ctgtgtcgcc atgaggggc ggcgggctct gtggtgcccc gcgacccccg       180
gccccggtga gcggtgaatg aaatccggct gtaatcagca tcccgtgccc accccgtcgg      240
ggaggtcagc gcccggagtg tctacgcagt cggatcctct cggactcggc catgctgtcg      300
gcagcatcgc gctcccgggt cttggcgtcc ctcggctgtt ctgcctgctg tccctggaag      360
gcgaaatgat caccggggag tgataccccg gtggtctcat cccggatgcc cacttcggcg      420
ccatccggca attcgggcag ctccgggtgg aagtaggtgg catccgatgc gtcggtgacg      480
ccatagtggg cgaagatctc atcctgctcg agggtgctca ggccactctc cggatcgata      540 tcggggggcgt ccttgatggc gtccttgctg aaaccgaggt gcagcttgtg ggcttccaat      600
ttcgcaccac ggagcgggac gaggctggaa tgacggccga agagcccgtg gtggacctca      660
acgaaggtgg gtagtccccgt gtcatcattg aggaacacgc cctccaccgc acccagcttg      720
tggccggagt tgtcgtaggc gctggcatcc agaaggggaaa cgatctcata tttgtcggtg      780
tgctcagaca tgatcttcct ttgctgtcgg tgtctggtac taccacggta gggctgaatg      840
caactgttat ttttctgtta ttttaggaat tggtccatat cccacaggct ggctgtggtc      900
aaatcgtcat caagtaatcc ctgtcacaca aatgggtgg tgggagccct ggtcgcggtt       960
ccgtggggag cgccgtgccc cgcaggatcg tcggcatcgg cggatctggc cggtaccccg     1020
cggtgaataa aatcattctg taaccttcat cacggttggt tttaggtatc cgccccttc      1080 gtcctgaccc cgtccccggc gcgcgggagc ccgcggttg cggtagacag gggagacgtg      1140
gacaccatga ggacaacggt catcgcagca agcgcattac tccttctcgc cggatgcgcg     1200 gatgggccc gggaggagac cgccggtgca ccgccgggtg agtcctccgg ggcatccgg       1260 gaggagggggg cggaggcgtc gacaagcatc accgacgtct acatcgccct cggggattcc     1320
tatgcggcga tgggcgggcg ggatcagccg ttacggggtg agccgttctg cctgcgctcg     1380
tccggtaatt acccggaact cctccacgca gaggtcaccg atctcacctg ccaggggggcg     1440 gtgaccggg atctgctcga acccaggacg ctgggggagc gcacgctgcc ggcgcaggtg      1500
gatgcgctga cggaggacac caccctggtc accctctcca tcgggggcaa tgacctcgga     1560
ttcggggagg tggcgggatg catccgggaa cggatcgccg gggagaacgc tgatgattgc     1620
gtggacctgc tgggggaaac catcggggag cagctcgatc agcttccccc gcagctggac     1680
cgcgtgcacg aggctatccg ggaccgcgcc ggggacgcgc aggttgtggt caccggttac     1740
ctgccgctcg tgtctgccgg ggactgcccc gaactgggg atgtctccga gcggatcgt       1800 cgttgggcgg ttgagctgac cgggcagatc aacgagaccg tgcgcgaggc ggccgaacga     1860
cacgatgccc tctttgtcct gcccgacgat gccgatgagc acaccagttg tgcaccccca     1920
cagcagcgct gggcggatat ccagggccaa cagaccgatg cctatccgct gcacccgacc     1980
tccgccggcc atgaggcgat ggccgccgcc gtccgggacg cgctgggcct ggaaccggtc     2040
```

-continued

```
cagccgtagc gccgggcgcg cgcttgtcga cgaccaaccc atgccaggct gcagtcacat   2100
ccgcacatag cgcgcgcggg cgatggagta cgcaccatag aggatgagcc cgatgccgac   2160
gatgatgagc agcacactgc cgaagggttg ttccccgagg gtgcgcagag ccgagtccag   2220
acctgcggcc tgctccggat catgggccca accggcgatg acgatcaaca cccccaggat   2280
cccgaaggcg ataccacggg cgacataacc ggctgttccg gtgatgatga tcgcggtccc   2340
gacctgccct gaccccgcac ccgcctccag atcctcccgg aaatcccggg tggccccctt   2400
ccagaggttg tagacacccg cccccagtac caccagcccg gcgaccacaa ccagcaccac   2460
accccagggt tgggatagga cggtggcggt gacatcggtg gcggtctccc catcggaggt   2520
gctgccgccc cgggcgaagg tggaggtggt caccgccagg agaagtagac catggccat   2580 gaccgccccc ttggccccttt ccttgaggtc ctcgcccgcc agcagctggc tcaattgcca   2640
gagtcccagg gccgccaggg cgatgacggc aacccacagg aggaactgcc cacccggagc   2700
ctccgcgatg gtggccaggg cacctgaatt cgaggcctca tcacccgaac cgccggatcc   2760
agtggcgatg cgcaccgcga tccacccgat gaggatgtgc agtatgccca ggacaatgaa   2820
accacctctg gccagggtgg tcagcgcggg gtggtcctcg gcctggtcgg cagcccgttc   2880
gatcgtccgt ttcgcggatc tggtgtcgcc cttatccata gctcccattg aaccgccttg   2940 agggtgggc ggccactgtc agggcggatt gtgatctgaa ctgtgatgtt ccatcaaccc    3000
```

<210> SEQ ID NO 43
<211> LENGTH: 268
<212> TYPE: PRT
<213> ORGANISM: Streptomyces coelicolor

<400> SEQUENCE: 43

```
Met Arg Arg Phe Arg Leu Val Gly Phe Leu Ser Ser Leu Val Leu Ala
1               5                   10                  15

Ala Gly Ala Ala Leu Thr Gly Ala Ala Thr Ala Gln Ala Ala Gln Pro
            20                  25                  30

Ala Ala Ala Asp Gly Tyr Val Ala Leu Gly Asp Ser Tyr Ser Ser Gly
        35                  40                  45

Val Gly Ala Gly Ser Tyr Ile Ser Ser Ser Gly Asp Cys Lys Arg Ser
    50                  55                  60

Thr Lys Ala His Pro Tyr Leu Trp Ala Ala His Ser Pro Ser Thr
65                  70                  75                  80

Phe Asp Phe Thr Ala Cys Ser Gly Ala Arg Thr Gly Asp Val Leu Ser
                85                  90                  95

Gly Gln Leu Gly Pro Leu Ser Ser Gly Thr Gly Leu Val Ser Ile Ser
            100                 105                 110

Ile Gly Gly Asn Asp Ala Gly Phe Ala Asp Thr Met Thr Thr Cys Val
        115                 120                 125

Leu Gln Ser Glu Ser Ser Cys Leu Ser Arg Ile Ala Thr Ala Glu Ala
    130                 135                 140

Tyr Val Asp Ser Thr Leu Pro Gly Lys Leu Asp Gly Val Tyr Ser Ala
145                 150                 155                 160

Ile Ser Asp Lys Ala Pro Asn Ala His Val Val Ile Gly Tyr Pro
                165                 170                 175

Arg Phe Tyr Lys Leu Gly Thr Thr Cys Ile Gly Leu Ser Glu Thr Lys
            180                 185                 190

Arg Thr Ala Ile Asn Lys Ala Ser Asp His Leu Asn Thr Val Leu Ala
        195                 200                 205
```

```
Gln Arg Ala Ala Ala His Gly Phe Thr Phe Gly Asp Val Arg Thr Thr
    210                 215                 220

Phe Thr Gly His Glu Leu Cys Ser Gly Ser Pro Trp Leu His Ser Val
225                 230                 235                 240

Asn Trp Leu Asn Ile Gly Glu Ser Tyr His Pro Thr Ala Ala Gly Gln
            245                 250                 255

Ser Gly Gly Tyr Leu Pro Val Leu Asn Gly Ala Ala
            260                 265

<210> SEQ ID NO 44
<211> LENGTH: 2000
<212> TYPE: DNA
<213> ORGANISM: Streptomyces coelicolor

<400> SEQUENCE: 44
cccggcggcc cgtgcaggag cagcagccgg cccgcgatgt cctcgggcgt cgtcttcatc     60
aggccgtcca tcgcgtcggc gaccggcgcc gtgtagttgg cccggacctc gtcccaggtg    120
cccgcggcga tctggcgggt ggtgcggtgc gggccgcgcc gaggggagac gtaccagaag    180
cccatcgtca cgttctccgg ctgcggttcg ggctcgtccg ccgctccgtc cgtcgcctcg    240
ccgagcacct tctcggcgag gtcggcgctg gtcgccgtca ccgtgacgtc ggcgccccgg    300
ctccagcgcg agatcagcag cgtccagccg tcgccctccg ccagcgtcgc gctgcggtcg    360
tcgtcgcggg cgatccgcag cacgcgcgcg ccgggcggca gcagcgtggc gccggaccgt    420
acgcggtcga tgttcgccgc gtgcgagtac ggctgctcac ccgtggcgaa cggccgagg     480
aacagcgcgt cgacgacgtc ggacggggag tcgctgtcgt ccacgttgag ccggatcggc    540
agggcttcgt gcgggttcac ggacatgtcg ccatgatcgg gcaccggcc gccgcgtgca    600
cccgcttt cc cgggcacgca cgacaggggc tttctcgccg tcttccgtcc gaacttgaac    660
gagtgtcagc catttcttgg catggacact tccagtcaac gcgcgtagct gctaccacgg    720
ttgtggcagc aatcctgcta agggaggttc catgagacgt ttccgacttg tcggcttcct    780
gagttcgctc gtcctcgccg ccggcgccgc cctcaccggg gcagcgaccg cccaggcggc    840
ccaacccgcc gccgccgacg gctatgtggc cctcggcgac tcctactcct ccggggtcgg    900
agcgggcagc tacatcagct cgagcggcga ctgcaagcgc agcacgaagg cccatcccta    960
cctgtgggcg gccgcccact cgccctccac gttcgacttc accgcctgtt ccggcgcccg   1020
tacgggtgat gttctctccg gacagctcgg cccgctcagc tccggcaccg gcctcgtctc   1080
gatcagcatc ggcggcaacg acgccggttt cgccgacacc atgacgacct gtgtgctcca   1140
gtccgagagc tcctgcctgt cgcggatcgc caccgccgag gcgtacgtcg actcgacgct   1200
gcccggcaag ctcgacggcg tctactcggc aatcagcgac aaggcgccga acgcccacgt   1260
cgtcgtcatc ggctacccgc gcttctacaa gctcggcacc acctgcatcg gcctgtccga   1320
gaccaagcgg acggcgatca acaaggcctc cgaccacctc aacaccgtcc tgcccagcg    1380
cgccgccgcc cacggcttca ccttcggcga cgtacgcacc accttcaccg gccacgagct   1440
gtgctccggc agcccctggc tgcacagcgt caactggctg aacatcggcg agtcgtacca   1500
ccccaccgcg gccggccagt ccggtggcta cctgccggtc ctcaacggcg ccgcctgacc   1560
tcaggcggaa ggagaagaag aaggagcgga gggagacgag gagtgggagg ccccgcccga   1620
cggggtcccc gtcccgtct ccgtctccgt cccggtcccg caagtcaccg agaacgccac    1680
cgcgtcggac gtggcccgca ccggactccg cacctccacg cgcacggcac tctcgaacgc   1740
```

-continued

```
gccggtgtcg tcgtgcgtcg tcaccaccac gccgtcctgg cgcgagcgct cgccgcccga      1800
cgggaaggac agcgtccgcc accccggatc ggagaccgac ccgtccgcgg tcacccaccg      1860
gtagccgacc tccgcgggca gccgcccgac cgtgaacgtc gccgtgaacg cgggtgcccg      1920
gtcgtgcggc ggcggacagg cccccgagta gtgggtgcgc gagcccacca cggtcacctc      1980
caccgactgc gctgcggggc                                                  2000
```

<210> SEQ ID NO 45
<211> LENGTH: 269
<212> TYPE: PRT
<213> ORGANISM: Streptomyces avermitilis

<400> SEQUENCE: 45

```
Met Arg Arg Ser Arg Ile Thr Ala Tyr Val Thr Ser Leu Leu Leu Ala
1               5                  10                  15

Val Gly Cys Ala Leu Thr Gly Ala Ala Thr Ala Gln Ala Ser Pro Ala
            20                  25                  30

Ala Ala Ala Thr Gly Tyr Val Ala Leu Gly Asp Ser Tyr Ser Ser Gly
        35                  40                  45

Val Gly Ala Gly Ser Tyr Leu Ser Ser Ser Gly Asp Cys Lys Arg Ser
    50                  55                  60

Ser Lys Ala Tyr Pro Tyr Leu Trp Gln Ala Ala His Ser Pro Ser Ser
65                  70                  75                  80

Phe Ser Phe Met Ala Cys Ser Gly Ala Arg Thr Gly Asp Val Leu Ala
                85                  90                  95

Asn Gln Leu Gly Thr Leu Asn Ser Ser Thr Gly Leu Val Ser Leu Thr
            100                 105                 110

Ile Gly Gly Asn Asp Ala Gly Phe Ser Asp Val Met Thr Thr Cys Val
        115                 120                 125

Leu Gln Ser Asp Ser Ala Cys Leu Ser Arg Ile Asn Thr Ala Lys Ala
    130                 135                 140

Tyr Val Asp Ser Thr Leu Pro Gly Gln Leu Asp Ser Val Tyr Thr Ala
145                 150                 155                 160

Ile Ser Thr Lys Ala Pro Ser Ala His Val Ala Val Leu Gly Tyr Pro
                165                 170                 175

Arg Phe Tyr Lys Leu Gly Gly Ser Cys Leu Ala Gly Leu Ser Glu Thr
            180                 185                 190

Lys Arg Ser Ala Ile Asn Asp Ala Asp Tyr Leu Asn Ser Ala Ile
        195                 200                 205

Ala Lys Arg Ala Ala Asp His Gly Phe Thr Phe Gly Asp Val Lys Ser
    210                 215                 220

Thr Phe Thr Gly His Glu Ile Cys Ser Ser Thr Trp Leu His Ser
225                 230                 235                 240

Leu Asp Leu Leu Asn Ile Gly Gln Ser Tyr His Pro Thr Ala Ala Gly
                245                 250                 255

Gln Ser Gly Gly Tyr Leu Pro Val Met Asn Ser Val Ala
            260                 265
```

<210> SEQ ID NO 46
<211> LENGTH: 1980
<212> TYPE: DNA
<213> ORGANISM: Streptomyces avermitilis

<400> SEQUENCE: 46

```
ccaccgccgg gtcggcggcg agtctcctgg cctcggtcgc ggagaggttg gccgtgtagc        60
```

| | | |
|---|---|---|
| cgttcagcgc ggcgccgaac gtcttcttca ccgtgccgcc gtactcgttg atcaggccct | 120 | |
| tgcccttgct cgacgcggcc ttgaagccgg tgcccttctt gagcgtgacg atgtagctgc | 180 | |
| ccttgatcgc ggtgggggag ccggcggcga gcaccgtgcc ctcggccggg gtggcctggg | 240 | |
| cgggcagtgc ggtgaatccg cccacgaggg cgccggtcgc cacggcggtt atcgcggcga | 300 | |
| tccggatctt cttgctacgc agctgtgcca tacgagggag tcctcctctg ggcagcggcg | 360 | |
| cgcctgggtg gggcgcacgg ctgtgggggg tgcgcgcgtc atcacgcaca cggccctgga | 420 | |
| gcgtcgtgtt ccgccctggg ttgagtaaag cctcggccat ctacgggggt ggctcaaggg | 480 | |
| agttgagacc ctgtcatgag tctgacatga gcacgcaatc aacggggccg tgagcacccc | 540 | |
| ggggcgaccc cggaaagtgc cgagaagtct tggcatggac acttcctgtc aacacgcgta | 600 | |
| gctggtacga cggttacggc agagatcctg ctaaagggag gttccatgag cgttcccga | 660 | |
| attacggcat acgtgacctc actcctcctc gccgtcggct gcgccctcac cggggcagcg | 720 | |
| acggcgcagg cgtccccagc cgccgcggcc acgggctatg tggcccctcg cgactcgtac | 780 | |
| tcgtccggtg tcggcgccgg cagctacctc agctccagcg gcgactgcaa gcgcagttcg | 840 | |
| aaggcctatc cgtacctctg gcaggccgcg cattcaccct cgtcgttcag tttcatggct | 900 | |
| tgctcgggcg ctcgtacggg tgatgtcctg gccaatcagc tcggcaccct gaactcgtcc | 960 | |
| accggcctgg tctccctcac catcggaggc aacgacgcgg gcttctccga cgtcatgacg | 1020 | |
| acctgtgtgc tccagtccga cagcgcctgc ctctcccgca tcaacacggc gaaggcgtac | 1080 | |
| gtcgactcca ccctgcccgg ccaactcgac agcgtgtaca cggcgatcag cacgaaggcc | 1140 | |
| ccgtcggccc atgtggccgt gctgggctac ccccgcttct acaaactggg cggctcctgc | 1200 | |
| ctcgcgggcc tctcggagac caagcggtcc gccatcaacg acgcggccga ctatctgaac | 1260 | |
| agcgccatcg ccaagcgcgc cgccgaccac ggcttcacct tcggcgacgt caagagcacc | 1320 | |
| ttcaccggcc atgagatctg ctccagcagc acctggctgc acagtctcga cctgctgaac | 1380 | |
| atcgccagt cctaccaccc gaccgcgccc ggccagtccg cgggctatct gccggtcatg | 1440 | |
| aacagcgtgg cctgagctcc cacggcctga atttttaagg cctgaatttt taaggcgaag | 1500 | |
| gtgaaccgga agcggaggcc ccgtccgtcg gggtctccgt cgcacaggtc accgagaacg | 1560 | |
| gcacggagtt ggacgtcgtg cgcaccgggt cgcgcacctc gacggcgatc tcgttcgaga | 1620 | |
| tcgttccgct cgtgtcgtac gtggtgacga acacctgctt ctgctgggtc tttccgccgc | 1680 | |
| tcgccgggaa ggacagcgtc ttccagcccg gatccgggac ctcgcccttc ttggtcaccc | 1740 | |
| agcggtactc cacctcgacc ggcacccggc ccaccgtgaa ggtcgccgtg aacgtgggcg | 1800 | |
| cctgggcggt gggcggcggg caggcaccgg agtagtcggt gtgcacgccg gtgaccgtca | 1860 | |
| ccttcacgga ctgggccggc ggggtcgtcg taccgccgcc gccaccgccg cctcccggag | 1920 | |
| tggagcccga gctgtggtcg cccccgccgt cggcgttgtc gtcctcgggg gttttcgaac | 1980 | |

<210> SEQ ID NO 47
<211> LENGTH: 372
<212> TYPE: PRT
<213> ORGANISM: Thermobifida fusca

<400> SEQUENCE: 47

Met Gly Ser Gly Pro Arg Ala Ala Thr Arg Arg Leu Phe Leu Gly
1               5                   10                  15

Ile Pro Ala Leu Val Leu Val Thr Ala Leu Thr Leu Val Leu Ala Val
            20                  25                  30

Pro Thr Gly Arg Glu Thr Leu Trp Arg Met Trp Cys Glu Ala Thr Gln

```
              35                  40                  45
Asp Trp Cys Leu Gly Val Pro Val Asp Ser Arg Gly Gln Pro Ala Glu
 50                  55                  60

Asp Gly Glu Phe Leu Leu Leu Ser Pro Val Gln Ala Ala Thr Trp Gly
 65                  70                  75                  80

Asn Tyr Tyr Ala Leu Gly Asp Ser Tyr Ser Gly Asp Gly Ala Arg
                     85                  90                  95

Asp Tyr Tyr Pro Gly Thr Ala Val Lys Gly Gly Cys Trp Arg Ser Ala
                    100                 105                 110

Asn Ala Tyr Pro Glu Leu Val Ala Glu Ala Tyr Asp Phe Ala Gly His
                    115                 120                 125

Leu Ser Phe Leu Ala Cys Ser Gly Gln Arg Gly Tyr Ala Met Leu Asp
                    130                 135                 140

Ala Ile Asp Glu Val Gly Ser Gln Leu Asp Trp Asn Ser Pro His Thr
145                 150                 155                 160

Ser Leu Val Thr Ile Gly Ile Gly Gly Asn Asp Leu Gly Phe Ser Thr
                    165                 170                 175

Val Leu Lys Thr Cys Met Val Arg Val Pro Leu Leu Asp Ser Lys Ala
                    180                 185                 190

Cys Thr Asp Gln Glu Asp Ala Ile Arg Lys Arg Met Ala Lys Phe Glu
                    195                 200                 205

Thr Thr Phe Glu Glu Leu Ile Ser Glu Val Arg Thr Arg Ala Pro Asp
210                 215                 220

Ala Arg Ile Leu Val Val Gly Tyr Pro Arg Ile Phe Pro Glu Glu Pro
225                 230                 235                 240

Thr Gly Ala Tyr Tyr Thr Leu Thr Ala Ser Asn Gln Arg Trp Leu Asn
                    245                 250                 255

Glu Thr Ile Gln Glu Phe Asn Gln Gln Leu Ala Glu Ala Val Ala Val
                    260                 265                 270

His Asp Glu Glu Ile Ala Ala Ser Gly Gly Val Gly Ser Val Glu Phe
                    275                 280                 285

Val Asp Val Tyr His Ala Leu Asp Gly His Glu Ile Gly Ser Asp Glu
290                 295                 300

Pro Trp Val Asn Gly Val Gln Leu Arg Asp Leu Ala Thr Gly Val Thr
305                 310                 315                 320

Val Asp Arg Ser Thr Phe His Pro Asn Ala Ala Gly His Arg Ala Val
                    325                 330                 335

Gly Glu Arg Val Ile Glu Gln Ile Glu Thr Gly Pro Gly Arg Pro Leu
                    340                 345                 350

Tyr Ala Thr Phe Ala Val Val Ala Gly Ala Thr Val Asp Thr Leu Ala
                    355                 360                 365

Gly Glu Val Gly
    370

<210> SEQ ID NO 48
<211> LENGTH: 968
<212> TYPE: DNA
<213> ORGANISM: Thermobifida fusca

<400> SEQUENCE: 48
ctgcagacac cgccccgcc ttctcccgga tcgtcatgtt cggcgactcc ctcagcgaca      60
ccggcaagat gtactccaag atgcgcggct acctgccgtc ctccccgccg tactacgagg     120
gccgcttctc gaacggcccg gtctggctgg agcagctgac gaagcagttc cccggcctga    180
```

```
cgatcgccaa cgaggccgag gggggcgcga ccgcagtcgc ctacaacaag atctcctgga    240
acccgaagta ccaggtcatt aacaacctcg actacgaggt cacccagttc ttgcagaagg    300
actcgttcaa gcccgacgac ctggtcatcc tgtgggtggg cgccaacgac tacctggcct    360
acggttggaa cacggagcag gacgccaagc gggtgcgcga cgccatctcg gacgcggcaa    420
accgcatggt cctgaacggc gcgaagcaga tcctgctgtt caacctgccc gacctgggcc    480
agaacccgtc cgcccgctcc cagaaggtcg tcgaggccgt ctcgcacgtg tccgcctacc    540
acaacaagct gctcctcaac ctcgcccggc agctcgcccc gacgggcatg gtcaagctgt    600
tcgagatcga caagcagttc gcggagatgc tgcgcgaccc ccagaacttc ggcctgagcg    660
acgtggagaa cccgtgctac gacggcggct acgtgtggaa gccgttcgcc acccggtccg    720
tctcgaccga ccggcagctg tcggccttct cgccccagga gcgcctggcg atcgctggca    780
acccgctcct ggcacaggcg gtagcttcgc cgatggcccg ccgctcggcc tcgcccctca    840
actgcgaggg caagatgttc tgggaccagg tccacccccac caccgtggtc cacgccgccc    900
tctcggagcg cgccgccacc ttcatcgaga cccagtacga gttcctcgcc cactagtcta    960
gaggatcc                                                              968
```

<210> SEQ ID NO 49
<211> LENGTH: 232
<212> TYPE: PRT
<213> ORGANISM: Artificial Sequence
<220> FEATURE:
<223> OTHER INFORMATION: structural model sequence for homology mapping

<400> SEQUENCE: 49

```
Thr Thr Val Tyr Leu Ala Gly Asp Ser Thr Met Ala Lys Asn Gly Gly
1               5                   10                  15

Gly Ser Gly Thr Asn Gly Trp Gly Glu Tyr Leu Ala Ser Tyr Leu Ser
            20                  25                  30

Ala Thr Val Val Asn Asp Ala Val Ala Gly Arg Ser Ala Arg Ser Tyr
        35                  40                  45

Thr Arg Glu Gly Arg Phe Glu Asn Ile Ala Asp Val Val Thr Ala Gly
    50                  55                  60

Asp Tyr Val Ile Val Glu Phe Gly His Asn Asp Gly Gly Ser Leu Ser
65                  70                  75                  80

Thr Asp Asn Gly Arg Thr Asp Cys Ser Gly Thr Gly Ala Glu Val Cys
                85                  90                  95

Tyr Ser Val Tyr Asp Gly Val Asn Glu Thr Ile Leu Thr Phe Pro Ala
            100                 105                 110

Tyr Leu Glu Asn Ala Ala Lys Leu Phe Thr Ala Lys Gly Ala Lys Val
        115                 120                 125

Ile Leu Ser Ser Gln Thr Pro Asn Asn Pro Trp Glu Thr Gly Thr Phe
    130                 135                 140

Val Asn Ser Pro Thr Arg Phe Val Glu Tyr Ala Glu Leu Ala Ala Glu
145                 150                 155                 160

Val Ala Gly Val Glu Tyr Val Asp His Trp Ser Tyr Val Asp Ser Ile
                165                 170                 175

Tyr Glu Thr Leu Gly Asn Ala Thr Val Asn Ser Tyr Phe Pro Ile Asp
            180                 185                 190

His Thr His Thr Ser Pro Ala Gly Ala Glu Val Val Ala Glu Ala Phe
        195                 200                 205

Leu Lys Ala Val Val Cys Thr Gly Thr Ser Leu Lys Ser Val Leu Thr
    210                 215                 220
```

Thr Thr Ser Phe Glu Gly Thr Cys
225                 230

<210> SEQ ID NO 50
<211> LENGTH: 184
<212> TYPE: PRT
<213> ORGANISM: Artificial Sequence
<220> FEATURE:
<223> OTHER INFORMATION: structural model sequence for homology mapping

<400> SEQUENCE: 50

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu
            180

<210> SEQ ID NO 51
<211> LENGTH: 225
<212> TYPE: PRT
<213> ORGANISM: Artificial Sequence
<220> FEATURE:
<223> OTHER INFORMATION: consensus sequence

<400> SEQUENCE: 51

Met Arg Arg Ser Arg Phe Leu Ala Ala Leu Ile Leu Leu Thr Leu Ala
1               5                   10                  15

Ala Leu Gly Ala Ala Ala Arg Ala Ala Pro Ala Ala Tyr Val Ala Leu
            20                  25                  30

Gly Asp Ser Tyr Ser Ser Gly Ala Gly Ser Tyr Ser Ser Gly Asp
        35                  40                  45

Cys Arg Ser Thr Lys Ala Tyr Pro Ala Leu Trp Ala Ala His Ala
    50                  55                  60

Ser Ser Phe Ser Phe Ala Cys Ser Gly Ala Arg Thr Tyr Asp Val Leu
65                  70                  75                  80

Ala Gln Leu Leu Asn Ser Thr Leu Val Ser Ile Thr Ile Gly Gly Asn
                85                  90                  95

Asp Ala Gly Phe Ala Asp Met Thr Thr Cys Val Leu Ser Asp Ser Ala

```
                    100                 105                 110
Cys Leu Arg Ile Ala Ala Lys Tyr Ile Thr Leu Pro Ala Arg Leu Asp
            115                 120                 125

Ser Val Tyr Ser Ala Ile Thr Arg Ala Pro Ala Arg Val Val Val Leu
            130                 135                 140

Gly Tyr Pro Arg Ile Tyr Ser Gly Leu Gly Leu Ser Thr Lys Arg Ala
145                 150                 155                 160

Ala Ile Asn Asp Ala Ala Asp Leu Asn Ser Val Ile Ala Lys Arg Ala
            165                 170                 175

Ala Asp His Gly Phe Thr Phe Gly Asp Val Thr Phe Gly His Glu Leu
            180                 185                 190

Cys Ser Ala Pro Trp Leu His Ser Leu Thr Leu Pro Val Ser Tyr His
            195                 200                 205

Pro Thr Ala Gly His Ala Ala Gly Tyr Leu Pro Val Leu Asn Ser Ile
            210                 215                 220

Thr
225

<210> SEQ ID NO 52
<211> LENGTH: 4
<212> TYPE: PRT
<213> ORGANISM: Artificial Sequence
<220> FEATURE:
<223> OTHER INFORMATION: sequence motif
<220> FEATURE:
<221> NAME/KEY: SITE
<222> LOCATION: (4)..(4)
<223> OTHER INFORMATION: Leu, Ala, Val, Ile, Phe, Tyr, His, Gln, Thr,
      Asn, Met or Ser

<400> SEQUENCE: 52

Gly Asp Ser Xaa
1

<210> SEQ ID NO 53
<211> LENGTH: 5
<212> TYPE: PRT
<213> ORGANISM: Artificial Sequence
<220> FEATURE:
<223> OTHER INFORMATION: sequence motif
<220> FEATURE:
<221> NAME/KEY: SITE
<222> LOCATION: (2)..(2)
<223> OTHER INFORMATION: Ala or Gly.
<220> FEATURE:
<221> NAME/KEY: SITE
<222> LOCATION: (5)..(5)
<223> OTHER INFORMATION: Tyr, Ala or Leu.

<400> SEQUENCE: 53

Gly Ala Asn Asp Tyr
1               5
```

US 8,927,036 B2

ENZYMATIC OIL-DEGUMMING METHOD

REFERENCE TO RELATED APPLICATIONS

This application is a continuation of U.S. patent application Ser. No. 11/623,689 filed Jan. 16, 2007 now U.S. Pat. No. 8,192,782, which is a continuation-in-part of International Patent Application PCT/GB2005/002823 filed Jul. 18, 2005 which published as WO 2006/008508 on Jan. 26, 2006, and which claims priority to Great Britain Patent Application Nos. 0513859.9 filed Jul. 7, 2005 and 0416035.4 filed Jul. 16, 2004, and to U.S. Patent Application No. 60/591,185 filed Jul. 26, 2004.

Each of the above referenced applications, and each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

It is noted that in this disclosure, terms such as " comprises", "comprised", "comprising", "contains", "containing" and the like can have the meaning attributed to them in U.S. Patent law; e.g., they can mean "includes", "included", "including" and the like. Terms such as "consisting essentially of" and "consists essentially of " have the meaning attributed to them in U.S. Patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, non-obvious, inventive, over the prior art, e.g., over documents cited herein or incorporated by reference herein. And, the terms "consists of" and "consisting of" have the meaning ascribed to them in U.S. Patent law; namely, that these terms are closed ended.

REFERENCE TO RELATED APPLICATIONS

Reference is made to the following related applications: U.S. application Ser. No. 09/750,990 filed on 20 Jul. 1999, U.S. application Ser. No. 10/409,391, WO2004/064537, WO2004/064987, PCT/IB2004/004378 and PCT/IB2004/004374. Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("herein cited documents"). Each of the herein cited documents, and each document cited or referenced in the herein cited documents, is hereby incorporated herein by reference.

FIELD OF INVENTION

The present invention relates to a method for enzymatically degumming edible oils using a lipid acyltransferase.

The present invention further relates to one or more lipid acyltransferases.

The present invention yet further relates to the use of a lipid acyltransferase to the degumming of edible oils.

TECHNICAL BACKGROUND

Traditionally two processes have been used for degumming of oil which are the physical degumming and the chemical degumming processes. Back in the 1990's the enzymatic degumming process was developed based on the use of pancreatic phospholipase. Because this enzyme was non-kosher the phospholipase was eventually substituted by a microbial phospholipase A1 (Lecitase Ultra™—Novozymes, Denmark). The enzymatic process has several advantages over the chemical or the physical degumming processes including cost savings, higher yield and a more environmentally friendly process.

SUMMARY ASPECTS OF THE PRESENT INVENTION

In one aspect, the present invention provides a method for the enzymatic degumming of vegetable oils or edible oils using a lipid acyltransferase as defined herein.

The present invention also provides a process of enzymatic degumming of vegetable or edible oils, comprising treating the edible or vegetable oil with a lipid acyl transferase according to the present invention so as to remove a major part of the phospholipid.

The present invention also provides a process of enzymatic degumming of vegetable or edible oils, comprising treating the edible or vegetable oil with a lipid acyl transferase according to the present invention so as to transfer an acyl group from a major part of the phospholipid to one or more acyl acceptors, for example to one or more sterols and/or stanols.

In another aspect, the present invention provides one or more lipid acyltransferases.

In one aspect, the present invention provides a lipid acyltransferase comprising the amino acid sequence shown as SEQ ID No. 16.

In another aspect, the present invention provides a lipid acyltransferase comprising the amino acid sequence shown as SEQ ID No. 16, or an amino acid sequence which has 75% or more, preferably 85% or more, more preferably 90% or more, even more preferably 95% or more, even more preferably 98% or more, or even more preferably 99% or more identity to SEQ ID No. 16.

In a yet further aspect, the present invention provides the use of a lipid acyltransferase in the degumming of edible oils (i) to remove phospholipids (such as phosphatidylcholine) and/or (ii) to increase the formation of sterol esters and/or stanol esters in the oil and/or (iii) to remove phospholipids (such as phosphatidylcholine) and/or to increase the formation of sterol esters and/or stanol esters in the oil without significantly increasing free fatty acids in the oil.

Preferable Aspects

The lipid acyltransferase for use in the present invention may be a natural lipid acyltransferase or may be a variant lipid acyltransferase.

For instance, the lipid acyltransferase for use in the method and uses of the present invention may be one as described in WO2004/064537 or WO2004/064987, or PCT/IB2004/004378 or GB0513859.9, for example.

The term "lipid acyltransferase" as used herein means an enzyme that has acyltransferase activity (generally classified as E.C. 2.3.1.x), whereby the enzyme is capable of transferring an acyl group from a lipid to one or more acceptor substrates, such as one or more of the following: a sterol; a stanol; a carbohydrate; a protein; a protein subunit; glycerol—preferably a sterol and/or a stanol.

Preferably, the lipid acyltransferase according to the present invention or for use in the methods and/or uses of the present invention is capable of transferring an acyl group from a lipid (as defined herein) to one or more of the following acyl acceptor substrates: a sterol or a stanol, preferably a sterol.

For some aspects the "acyl acceptor" according to the present invention may be any compound comprising a hydroxy group (—OH), such as for example, polyvalent alcohols, including glycerol; sterols; stanols; carbohydrates; hydroxy acids including fruit acids, citric acid, tartaric acid, lactic acid and ascorbic acid; proteins or a sub-unit thereof, such as amino acids, protein hydrolysates and peptides (partly hydrolysed protein) for example; and mixtures and derivatives thereof. Preferably, the "acyl acceptor" according to the present invention is not water.

The acyl acceptor is preferably not a monoglyceride.

In one aspect, the lipid acyltransferase according to the present invention or for use in the methods and/or uses of the present invention may, as well as being able to transfer an acyl group from a lipid to a sterol and/or a stanol, additionally be able to transfer the acyl group from a lipid to one or more of the following: a carbohydrate, a protein, a protein subunit, glycerol.

Preferably, the lipid substrate upon which the lipid acyltransferase according to the present invention acts is one or more of the following lipids: a phospholipid, such as a lecithin, e.g. phosphatidylcholine.

This lipid substrate may be referred to herein as the "lipid acyl donor". The term lecithin as used herein encompasses phosphatidylcholine, phosphatidylethanolamine, phosphatidylinositol, phosphatidylserine and phosphatidylglycerol.

For some aspects, preferably the lipid substrate upon which the lipid acyltransferase according to the present invention or for use in the method and/or uses of the present invention acts as a phospholipid, such as lecithin, for example phosphatidylcholine.

For some aspects, preferably the lipid acyltransferase according to the present invention or for use in the method and/or uses of the present invention is incapable, or substantially incapable, of acting on a triglyceride and/or a 1-monoglyceride and/or 2-monoglyceride.

Suitably, the lipid acyltransferase according to the present invention or for use in the method and/or uses of the present invention may exhibit one or more of the following phospholipase activities: phospholipase A2 activity (E.C. 3.1.1.4) or phospholipase A1 activity (E.C. 3.1.1.32).

Suitably, for some aspects the lipid acyltransferase according to the present invention or for use in the method and/or uses of the present invention may be capable of transferring an acyl group from a phospholipid to a sterol and/or a stanol.

For some aspects, preferably the lipid acyltransferase according to the present invention or for use in methods and/or uses of the present invention is capable of transferring an acyl group from a phospholipid to a sterol and/or a stanol to form at least a sterol ester and/or a stanol ester.

For some aspects, preferably the lipid acyltransferase according to the present invention or for use in the method and/or uses of the present invention does not exhibit triacylglycerol lipase activity (E.C. 3.1.1.3) or does not exhibit significant triacylglycerol lipase activity (E.C. 3.1.1.3).

The lipid acyltransferase according to the present invention or for use in the method and/or uses of the present invention may be capable of transferring an acyl group from a lipid to a sterol and/or a stanol. Thus, in one embodiment the "acyl acceptor" according to the present invention may be either a sterol or a stanol or a combination of both a sterol and a stanol.

Preferably, the lipid acyltransferase enzyme according to the present invention or for use in methods and uses of the present invention may be characterised using the following criteria:

(i) the enzyme possesses acyl transferase activity which may be defined as ester transfer activity whereby the acyl part of an original ester bond of a lipid acyl donor is transferred to an acyl acceptor to form a new ester; and (ii) the enzyme comprises the amino acid sequence motif GDSX, wherein X is one or more of the following amino acid residues L, A, V, I, F, Y, H, Q, T, N, M or S.

Preferably, X of the GDSX motif is L or Y. More preferably, X of the GDSX motif is L. Thus, preferably the enzyme according to the present invention comprises the amino acid sequence motif GDSL.

The GDSX motif is comprised of four conserved amino acids. Preferably, the serine within the motif is a catalytic serine of the lipid acyltransferase enzyme. Suitably, the serine of the GDSX motif may be in a position corresponding to Ser-16 in *Aeromonas hydrophila* lipolytic enzyme taught in Brumlik & Buckley (Journal of Bacteriology April 1996, Vol. 178, No. 7, p 2060-2064).

To determine if a protein has the GDSX motif according to the present invention, the sequence is preferably compared with the hidden markov model profiles (HMM profiles) of the pfam database in accordance with the procedures taught in WO2004/064537 or WO2004/064987.

Pfam is a database of protein domain families. Pfam contains curated multiple sequence alignments for each family as well as profile hidden Markov models (profile HMMs) for identifying these domains in new sequences. An introduction to Pfam can be found in Bateman A et al. (2002) Nucleic Acids Res. 30; 276-280. Hidden Markov models are used in a number of databases that aim at classifying proteins, for review see Bateman A and Haft DH (2002) Brief Bioinform 3; 236-245.

--- http://www.ncbi.nlm.nih.gov/entrez/query.fcgi?cmd=Retrieve&db=PubMed&list_uids=12230032&dopt=Abstract
http://www.ncbi.nlm.nih.gov/entrez/query.fcgi?cmd=Retrieve&db=PubMed&list_uids=11752314&dopt=Abstract

---

For a detailed explanation of hidden Markov models and how they are applied in the Pfam database see Durbin R, Eddy S, and Krogh A (1998) Biological sequence analysis; probabilistic models of proteins and nucleic acids. Cambridge University Press, ISBN 0-521-62041-4. The Hammer software package can be obtained from Washington University, St Louis, USA.

Alternatively, the GDSX motif can be identified using the Hammer software package, the instructions are provided in Durbin R, Eddy S, and Krogh A (1998) Biological sequence analysis; probabilistic models of proteins and nucleic acids. Cambridge University Press, ISBN 0-521-62041-4 and the references therein, and the HMMER2 profile provided within this specification.

The PFAM database can be accessed, for example, through several servers which are currently located at the following websites.

http://www.sanger.ac.uk/Software/Pfam/index.shtml
http://pfam.wustl.edu/
http://pfam.jouy.inra.fr/
http://pfam.cgb.ki.se/

The database offers a search facility where one can enter a protein sequence. Using the default parameters of the database the protein sequence will then be analysed for the presence of Pfam domains. The GDSX domain is an established domain in the database and as such its presence in any query sequence will be recognised. The database will return the alignment of the Pfam00657 consensus sequence to the query sequence.

Preferably the lipid acyltransferase enzyme for use in methods and uses of the invention can be aligned using the Pfam00657 consensus sequence (for a full explanation see WO2004/064537 or WO2004/064987).

Preferably, a positive match with the hidden markov model profile (HMM profile) of the pfam00657 domain family indicates the presence of the GDSL or GDSX domain according to the present invention.

Preferably when aligned with the Pfam00657 consensus sequence the lipid acyltransferase for use in the methods or uses of the invention may have at least one, preferably more than one, preferably more than two, of the following, a GDSx block, a GANDY block, a HPT block. Suitably, the lipid acyltransferase may have a GDSx block and a GANDY block. Alternatively, the enzyme may have a GDSx block and a HPT block. Preferably the enzyme comprises at least a GDSx block.

Preferably, residues of the GANDY motif are selected from GANDY, GGNDA, GGNDL, most preferably GANDY.

Preferably, when aligned with the Pfam00657 consensus sequence the enzyme for use in the methods or uses of the invention have at least one, preferably more than one, preferably more than two, preferably more than three, preferably more than four, preferably more than five, preferably more than six, preferably more than seven, preferably more than eight, preferably more than nine, preferably more than ten, preferably more than eleven, preferably more than twelve, preferably more than thirteen, preferably more than fourteen, of the following amino acid residues when compared to the reference *A. hydrophilia* polypeptide sequence, namely SEQ ID No. 1: 28hid, 29hid, 30hid, 31hid, 32gly, 33Asp, 34Ser, 35hid, 130hid, 131 Gly, 132Hid, 133Asn, 134Asp, 135hid, 309H is.

The pfam00657 GDSX domain is a unique identifier which distinguishes proteins possessing this domain from other enzymes.

The pfam00657 consensus sequence is presented in FIG. 12 as SEQ ID No. 2. This is derived from the identification of the pfam family 00657, database version 6, which may also be referred to as pfam00657.6 herein.

The consensus sequence may be updated by using further releases of the pfam database (for example see WO2004/064537 or WO2004/064987).

The presence of the GDSx, GANDY and HPT blocks are found in the pfam family 00657 from both releases of the database. Future releases of the pfam database can be used to identify the pfam family 00657.

In one embodiment, the lipid acyltransferase enzyme for use in methods and uses of the present invention may be characterised using the following criteria:
  (i) the enzyme possesses acyl transferase activity which may be defined as ester transfer activity whereby the acyl part of an original ester bond of a lipid acyl donor is transferred to acyl acceptor to form a new ester;
  (ii) the enzyme comprises the amino acid sequence motif GDSX, wherein X is one or more of the following amino acid residues L, A, V, I, F, Y, H, Q, T, N, M or S.;
  (iii) the enzyme comprises His-309 or comprises a histidine residue at a position corresponding to His-309 in the *Aeromonas hydrophila* lipid acyltransferase enzyme shown in FIGS. 11 and 13 (SEQ ID NO. 1 or SEQ ID No. 3).

Preferably, the amino acid residue of the GDSX motif is L.

In SEQ ID No. 3 or SEQ ID No. 1 the first 18 amino acid residues form a signal sequence. His-309 of the full length sequence, that is the protein including the signal sequence, equates to His-291 of the mature part of the protein, i.e. the sequence without the signal sequence.

In one embodiment, the lipid acyltransferase enzyme for use in methods and uses of the present invention comprises the following catalytic triad: Ser-34, Asp-134 and His-309 or comprises a serine residue, an aspartic acid residue and a histidine residue, respectively, at positions corresponding to Ser-34, Asp-134 and His-309 in the *Aeromonas hydrophila* lipid acyltransferase enzyme shown in FIG. 13 (SEQ ID No. 3) or FIG. 11 (SEQ ID No. 1). As stated above, in the sequence shown in SEQ ID No. 3 or SEQ ID No. 1 the first 18 amino acid residues form a signal sequence. Ser-34, Asp-134 and His-309 of the full length sequence, that is the protein including the signal sequence, equate to Ser-16, Asp-116 and His-291 of the mature part of the protein, i.e. the sequence without the signal sequence. In the pfam00657 consensus sequence, as given in FIG. 12 (SEQ ID No. 2) the active site residues correspond to Ser-7, Asp-157 and His-348.

In one embodiment, the lipid acyltransferase enzyme for use in methods and uses of the present invention may be characterised using the following criteria:
  (i) the enzyme possesses acyl transferase activity which may be defined as ester transfer activity whereby the acyl part of an original ester bond of a first lipid acyl donor is transferred to an acyl acceptor to form a new ester; and
  (ii) the enzyme comprises at least Gly-32, Asp-33, Ser-34, Asp-134 and His-309 or comprises glycine, aspartic acid, serine, aspartic acid and histidine residues at positions corresponding to Gly-32, Asp-33, Ser-34, Asp-134 and His-309, respectively, in the *Aeromonas hydrophila* lipid acyltransferase enzyme shown in FIG. 13 (SEQ ID No. 3) or FIG. 11 (SEQ ID No. 1).

Suitably, the lipid acyltransferase enzyme for use in methods and uses of present invention comprises one or more of the following amino acid sequences:
  (i) the amino acid sequence shown as SEQ ID No. 3 (see FIG. 13)
  (ii) the amino acid sequence shown as SEQ ID No. 4 (see FIG. 14)
  (iii) the amino acid sequence shown as SEQ ID No. 5 (see FIG. 15)
  (iv) the amino acid sequence shown as SEQ ID No. 6 (see FIG. 16)
  (v) the amino acid sequence shown as SEQ ID No. 7 (see FIG. 17)
  (vi) the amino acid sequence shown as SEQ ID No. 8 (see FIG. 18)
  (vii) the amino acid sequence shown as SEQ ID No. 9 (FIG. 19)
  (viii) the amino acid sequence shown as SEQ ID No. 10 (FIG. 20)
  (ix) the amino acid sequence shown as SEQ ID No. 11 (FIG. 21)

(x) the amino acid sequence shown as SEQ ID No. 12 (FIG. 22)
(xi) the amino acid sequence shown as SEQ ID No. 13 (FIG. 23)
(xii) the amino acid sequence shown as SEQ ID No. 14 (FIG. 24)
(xiii) the amino acid sequence shown as SEQ ID No. 1 (FIG. 11)
(xiv) the amino acid sequence shown as SEQ ID No. 15 (FIG. 25) or
an amino acid sequence which has 75% or more identity with any one of the sequences shown as SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, or SEQ ID No. 15.

Suitably, the lipid acyltransferase enzyme for use in methods and uses of the present invention comprises either the amino acid sequence shown as SEQ ID No. 3 or as SEQ ID No. 4 or SEQ ID No. 1 or SEQ ID No. 15 or comprises an amino acid sequence which has 75% or more, preferably 80% or more, preferably 85% or more, preferably 90% or more, preferably 95% or more, identity with the amino acid sequence shown as SEQ ID No. 3 or the amino acid sequence shown as SEQ ID No. 4 or the amino acid sequence shown as SEQ ID No. 1 or the amino acid sequence shown as SEQ ID No. 15.

Suitably the lipid acyltransferase enzyme for use in methods and uses of the present invention comprises an amino acid sequence which has 80% or more, preferably 85% or more, more preferably 90% or more and even more preferably 95% or more identity with any one of the sequences shown as SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 1, or SEQ ID No. 15.

Suitably, the lipid acyltransferase enzyme for use in methods and uses of the present invention comprises one or more of the following amino acid sequences:
(a) an amino acid sequence shown as amino acid residues 1-100 of SEQ ID No. 3 or SEQ ID No. 1;
(b) an amino acid sequence shown as amino acids residues 101-200 of SEQ ID No. 3 or SEQ ID No. 1;
(c) an amino acid sequence shown as amino acid residues 201-300 of SEQ ID No. 3 or SEQ ID No. 1; or
(d) an amino acid sequence which has 75% or more, preferably 85% or more, more preferably 90% or more, even more preferably 95% or more identity to any one of the amino acid sequences defined in (a)-(c) above.

Suitably, the lipid acyltransferase enzyme for use in methods and uses of the present invention comprises one or more of the following amino acid sequences:
(a) an amino acid sequence shown as amino acid residues 28-39 of SEQ ID No. 3 or SEQ ID No. 1;
(b) an amino acid sequence shown as amino acids residues 77-88 of SEQ ID No. 3 or SEQ ID No. 1;
(c) an amino acid sequence shown as amino acid residues 126-136 of SEQ ID No. 3 or SEQ ID No. 1;
(d) an amino acid sequence shown as amino acid residues 163-175 of SEQ ID No. 3 or SEQ ID No. 1;
(e) an amino acid sequence shown as amino acid residues 304-311 of SEQ ID No. 3 or SEQ ID No. 1; or
(f) an amino acid sequence which has 75% or more, preferably 85% or more, more preferably 90% or more, even more preferably 95% or more identity to any one of the amino acid sequences defined in (a)-(e) above.

In one aspect, the lipid acyltransferase for use in the method and uses of the present invention may be the lipid acyl transferase from *Candida parapsilosis* as taught in EP 1 275 711. Thus in one aspect the lipid acyltransferase for use in the method and uses of the present invention may be a lipid acyltransferase comprising one of the amino acid sequences taught in SEQ ID No. 17 (FIG. 28) or SEQ ID No. 18 (FIG. 29).

Much by preference, the lipid acyltransferase for use in the method and uses of the present invention may be a lipid acyltransferase comprising the amino acid sequence shown as SEQ ID No. 16 (FIG. 10), or an amino acid sequence which has 75% or more, preferably 85% or more, more preferably 90% or more, even more preferably 95% or more, even more preferably 98% or more, or even more preferably 99% or more identity to SEQ ID No. 16. This enzyme could be considered a variant enzyme.

In one aspect, the lipid acyltransferase for use in the methods and uses of the present invention may be a lecithin: cholesterol acyltransferase (LCAT) or variant thereof (for example a variant made by molecular evolution)

Suitable LCATs are known in the art and may be obtainable from one or more of the following organisms for example: mammals, rat, mice, chickens, *Drosophila melanogaster*, plants, including *Arabidopsis* and *Oryza sativa*, nematodes, fungi and yeast.

In one embodiment the lipid acyltransferase enzyme for use in the methods and uses of the present invention may be the lipid acyltransferase obtainable, preferably obtained, from the *E. coli* strains TOP 10 harbouring pPet12aAhydro and pPet12aASalmo deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 22 Dec. 2003 under accession numbers NICMB 41204 and NICMB 41205, respectively.

Highly preferred lipid acyl transferases for use in the methods of the invention include those isolated from *Aeromonas* spp., preferably *Aeromonas hydrophila* or *A. salmonicida*, most preferable *A. salmonicida*. Most preferred lipid acyl transferases for use in the present invention are encoded by SEQ ID No.s 1, 3, 4, 15, 16. It will be recognised by the skilled person that it is preferable that the signal peptides of the acyl transferase has been cleaved during expression of the transferase. The signal peptide of SEQ ID 1, 3, 4, 15 and 16 are amino acids 1-18. Therefore the most preferred regions are amino acids 19-335 for SEQ ID No. 1 and SEQ ID No. 3 (*A. hydrophilia*) and amino acids 19-336 for SEQ ID No. 4, SEQ ID No. 15 and SEQ ID No. 16. (*A. salmonicida*). When used to determine the homology of identity of the amino acid sequences, it is preferred that the alignments as herein described use the mature sequence.

Therefore the most preferred regions for determining homology (identity) are amino acids 19-335 for SEQ ID No. 1 and 3 (*A. hydrophilia*) and amino acids 19-336 for SEQ ID No.s 4, 15 and 16. (*A. salmonicida*). SEQ ID 34 and 35 are mature protein sequences of the highly preferred lipid acyl transferases from *A. hydrophilia* and *A. salmonicida* respectively.

A lipid acyl transferase for use in the invention may also be isolated from *Thermobifida*, preferably *T. fusca*, most preferably that encoded by SEQ ID No. 28.

A lipid acyl transferase for use in the invention may also be isolated from *Streptomyces*, preferable *S. avermitis*, most preferably that encoded by SEQ ID No. 32. Other possible enzymes for use in the present invention from *Streptomyces* include those encoded by SEQ ID No.s 5, 6, 9, 10, 11, 12, 13, 14, 31, 33. The examples show that the enzyme encoded by SEQ ID No. 33 is highly effective in enzymatic degumming.

An enzyme for use in the invention may also be isolated from *Corynebacterium*, preferably *C. efficiens*, most preferably that encoded by SEQ ID No. 29.

Suitably, the lipid acyltransferase for use in the methods and uses according to the present invention may be a lipid acyltransferase comprising any one of the amino acid sequences shown as SEQ ID No.s 37, 38, 40, 41, 43, 45, or 47 or an amino acid sequence which has at least 70%, 75%, 80%, 85%, 90%, 95%, 96%, 97% or 98% identity therewith, or encoded by any one of the nucleotide sequences shown as SEQ ID No.s 36, 39, 42, 44, 46, or 48 or a nucleotide sequence which has at least 70%, 75%, 80%, 85%, 90%, 95%, 96%, 97% or 98% identity therewith.

Preferably, the lipid acyltransferase for use in the methods and uses according to the present invention is a lipid acyltransferase capable of hydrolysing at least galactolipids and/or capable of transferring an acyl group from at least a galactolipid to one or more acyl acceptor substrates, wherein the enzyme is obtainable, preferably obtained, from *Streptomyces* species.

In one embodiment the lipid acyltransferase for use in the methods and uses according to the present invention is preferably a lipid acyltransferase capable of hydrolysing at least galactolipids and/or capable of transferring an acyl group from at least a galactolipid to one or more acyl acceptor substrates, wherein the enzyme is encoded by a nucleic acid selected from the group consisting of:
  a) a nucleic acid comprising a nucleotide sequence shown in SEQ ID No. 36;
  b) a nucleic acid which is related to the nucleotide sequence of SEQ ID No. 36 by the degeneration of the genetic code; and
  c) a nucleic acid comprising a nucleotide sequence which has at least 70% identity with the nucleotide sequence shown in SEQ ID No. 36.

In one embodiment, the lipid acyltransferase for use in the methods and uses according to the present invention is preferably a lipid acyltransferase comprising an amino acid sequence as shown in SEQ ID No. 37 or an amino acid sequence which has at least 60% identity thereto.

In another embodiment the lipid acyltransferase for use in the methods and uses according to the present invention is preferably a lipid acyltransferase capable of hydrolysing at least a galactolipid and/or capable of transferring an acyl group from at least a galactolipid to one or more acyl acceptor substrates, wherein the enzyme comprises an amino acid sequence as shown in SEQ ID No. 37 or an amino acid sequence which has at least 60% identity thereto.

Preferably, the lipid acyltransferase for use in the methods and uses according to the present invention is a lipid acyltransferase capable of hydrolysing at least galactolipids and/or capable of transferring an acyl group from at least a galactolipid to one or more acyl acceptor substrates, wherein the enzyme is obtainable, preferably obtained, from *Thermobifida* species, preferably *Thermobifida fusca*.

Preferably, the lipid acyltransferase for use in the methods and uses according to the present invention is a lipolytic enzyme capable of hydrolysing at least galactolipids and/or capable of transferring an acyl group from at least a galactolipid to one or more acyl acceptor substrates, wherein the enzyme is obtainable, preferably obtained, from *Corynebacterium* species, preferably *Corynebacterium efficiens*.

In a further embodiment the lipid acyltransferase for use in the methods and uses according to the present invention may be a lipid acyltransferase comprising any one of the amino acid sequences shown as SEQ ID No. 37, 38, 40, 41, 43, 45 or 47 or an amino acid sequence which has at least 70%, 75%, 80%, 85%, 90%, 95%, 96%, 97% or 98% identity therewith, or encoded by any one of the nucleotide sequences shown as SEQ ID No. 39, 42, 44, 46 or 48 or a nucleotide sequence which has at least 70%, 75%, 80%, 85%, 90%, 95%, 96%, 97% or 98% identity therewith.

In a further embodiment the lipid acyltransferase for use in the methods and uses according to the present invention may be a lipid acyltransferase comprising any one of amino sequences shown as SEQ ID No. 38, 40, 41, 45 or 47 or an amino acid sequence which has at least 70%, 75%, 80%, 85%, 90%, 95%, 96%, 97% or 98% identity therewith for the uses described herein.

In a further embodiment the lipid acyltransferase for use in the methods and uses according to the present invention may be a lipid acyltransferase comprising any one of amino sequences shown as SEQ ID No. 38, 40, or 47 or an amino acid sequence which has at least 70%, 75%, 80%, 85%, 90%, 95%, 96%, 97% or 98% identity therewith for the uses described herein.

More preferably in one embodiment the lipid acyltransferase for use in the methods and uses according to the present invention may be a lipid acyltransferase comprising the amino acid sequence shown as SEQ ID No. 47 or an amino acid sequence which has at least 70%, 75%, 80%, 85%, 90%, 95%, 96%, 97% or 98% identity therewith.

In another embodiment the lipid acyltransferase for use in the methods and uses according to the present invention may be a lipid acyltransferase comprising the amino acid sequence shown as SEQ ID No. 43 or 44 or an amino acid sequence which has at least 80%, 85%, 90%, 95%, 96%, 97% or 98% identity therewith.

In another embodiment the lipid acyltransferase for use in the methods and uses according to the present invention may be a lipid acyltransferase comprising the amino acid sequence shown as SEQ ID No. 41 or an amino acid sequence which has at least 70%, 75%, 80%, 85%, 90%, 95%, 96%, 97% or 98% identity therewith.

In one embodiment the lipid acyltransferase for use in the methods and uses according to the present invention may be a lipid acyltransferase capable of hydrolysing at least galactolipids and/or capable of transferring an acyl group from at least a galactolipid to one or more acyl acceptor substrates, wherein the enzyme is encoded by a nucleic acid selected from the group consisting of:
  a) a nucleic acid comprising a nucleotide sequence shown in SEQ ID No. 36;
  b) a nucleic acid which is related to the nucleotide sequence of SEQ ID No. 36 by the degeneration of the genetic code; and
  c) a nucleic acid comprising a nucleotide sequence which has at least 70% identity with the nucleotide sequence shown in SEQ ID No. 36.

In one embodiment the lipid acyltransferase according to the present invention may be a lipid acyltransferase obtainable, preferably obtained, from the *Streptomyces* strains L130 or L131 deposited by Danisco A/S of Langebrogade 1, DK-1001 Copenhagen K, Denmark under the Budapest Treaty on the International Recognition of the Deposit of Microorganisms for the purposes of Patent Procedure at the National Collection of Industrial, Marine and Food Bacteria (NCIMB) 23 St. Machar Street, Aberdeen Scotland, GB on 25 Jun. 2004 under accession numbers NCIMB 41226 and NCIMB 41227, respectively.

Suitable lipid acyltransferases for use in accordance with the present invention and/or in the methods of the present invention may comprise any one of the following amino acid sequences and/or be encoded by the following nucleotide sequences:
a polynucleotide encoding a lipid acyltransferase according to the present invention (SEQ ID No. 16);
an amino acid sequence of a lipid acyltransferase according to the present invention (SEQ ID No. 17).

A suitable lipid acyl-transferase enzyme for use in the methods of the invention may also be identified by alignment to the L131 (SEQ ID No. 37) sequence using Align X, the Clustal W pairwise alignment algorithm of VectorNTI using default settings.

An alignment of the L131 and homologues from *S. avermitilis* and *T. fusca* illustrates that the conservation of the GDSx motif (GDSY in L131 and *S. avermitilis* and *T. fusca*), the GANDY box, which is either GGNDA or GGNDL, and the HPT block (considered to be the conserved catalytic histadine). These three conserved blocks are highlighted in FIG. 61.

When aligned to either the pfam Pfam00657 consensus sequence (as described in WO04/064987) and/or the L131 sequence herein disclosed (SEQ ID No 37) it is possible to identify three conserved regions, the GDSx block, the GANDY block and the HTP block (see WO04/064987 for further details).

When aligned to either the pfam Pfam00657 consensus sequence (as described in WO04/064987) and/or the L131 sequence herein disclosed (SEQ ID No 37)
  i) The lipid acyl-transferase enzyme of the invention, or for use in methods of the invention, has preferably a GDSx motif, more preferably a GDSx motif selected from GDSL or GDSY motif.
  and/or
  ii) The lipid acyl-transferase enzyme of the invention, or for use in methods of the invention, has preferably a GANDY block, more preferably a GANDY block comprising amino GGNDx, more preferably GGNDA or GGNDL.
  and/or
  iii) The enzyme of the invention, or for use in methods of the invention, has preferable an HTP block.
  and preferably
  iv) The galactolipase/lipid acyl-transferase enzyme of the invention, or for use in methods of the invention, has preferably a GDSx or GDSY motif, and a GANDY block comprising amino GGNDx, preferably GGNDA or GGNDL, and a HTP block (conserved histidine).

Suitably, when the lipid acyltransferase for use in the methods or uses of the present invention, may be a variant lipid acyltransferase, in which case the enzyme may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7 (defined hereinbelow).

For instance the variant lipid acyltransferase enzyme for use in the methods or uses of the present invention may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues detailed in set 2 or set 4 or set 6 or set 7 (defined hereinbelow) identified by said parent sequence being structurally aligned with the structural model of P10480 defined herein, which is preferably obtained by structural alignment of P10480 crystal structure coordinates with 1IVN.PDB and/or 1DEO.PDB as taught herein.

In a further embodiment the variant lipid acyltransferase enzyme for use in the methods or uses of the present invention may be characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues taught in set 2 identified when said parent sequence is aligned to the pfam consensus sequence (SEQ ID No. 2—FIG. 12) and modified according to a structural model of P10480 to ensure best fit overlap (see FIG. 30) as taught herein.

Suitably the variant lipid acyltransferase enzyme may comprise an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues defined in set 2 or set 4 or set 6 or set 7 (hereinafter defined) identified by sequence alignment with SEQ ID No. 34.

Alternatively the variant lipid acyltransferase enzyme may be a variant enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues defined in set 2 or set 4 or set 6 or set 7 identified by said parent sequence being structurally aligned with the structural model of P10480 defined herein, which is preferably obtained by structural alignment of P10480 crystal structure coordinates with 1IVN.PDB and/or 1DEO.PDB as taught herein.

Alternatively, the variant lipid acyltransferase enzyme may be a variant enzyme comprising an amino acid sequence, which amino acid sequence is shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32, or SEQ ID No. 33 except for one or more amino acid modifications at any one or more of the amino acid residues taught in set 2 identified when said parent sequence is aligned to the pfam consensus sequence (SEQ ID No. 2) and modified according to a structural model of P10480 to ensure best fit overlap (see FIG. 30) as taught hereinbelow.

The term "modifying" as used herein means adding, substituting and/or deleting. Preferably the term "modifying" means "substituting".

For the avoidance of doubt, when an amino acid is substituted in the parent enzyme it is preferably substituted with an amino acid which is different from that originally found at that position in the parent enzyme thus to produce a variant enzyme. In other words, the term "substitution" is not intended to cover the replacement of an amino acid with the same amino acid.

Preferably, the parent enzyme is an enzyme which comprises the amino acid sequence shown as SEQ ID No. 34 and/or SEQ ID No. 15 and/or SEQ ID No. 35.

Preferably, the variant enzyme is an enzyme which comprises an amino acid sequence, which amino acid sequence is shown as SEQ ID No. 34 or SEQ ID No. 35 except for one or more amino acid modifications at any one or more of the amino acid residues defined in set 2 or set 4 or set 6 or set 7.

In one embodiment, preferably the variant enzyme comprises one or more amino acid modifications compared with the parent sequence at least one of the amino acid residues defined in set 4.

Suitably, the variant enzyme comprises one or more of the following amino acid modifications compared with the parent enzyme:
S3E, A, G, K, M, Y, R, P, N, T or G
E309Q, R or A, preferably Q or R
−318Y, H, S or Y, preferably Y.

Preferably, X of the GDSX motif is L. Thus, preferably the parent enzyme comprises the amino acid motif GDSL.

Preferably the method of producing a variant lipid acyltransferase enzyme further comprises one or more of the following steps:
1) structural homology mapping or
2) sequence homology alignment.

Suitably, the structural homology mapping may comprise one or more of the following steps:
i) aligning a parent sequence with a structural model (1IVN.PDB) shown in FIG. 46;
ii) selecting one or more amino acid residue within a 10Å sphere centred on the central carbon atom of the glycerol molecule in the active site (see FIG. 47) (such as one or more of the amino acid residues defined in set 1 or set 2); and
iii) modifying one or more amino acids selected in accordance with step (ii) in said parent sequence.

In one embodiment the amino acid residue selected may reside within a 9, preferably within a 8, 7, 6, 5, 4, or 3Å sphere centred on the central carbon atom of the glycerol molecule in the active site (see FIG. 47).

Suitably, the structural homology mapping may comprise one or more of the following steps:
i) aligning a parent sequence with a structural model (1IVN.PDB) shown in FIG. 46;
ii) selecting one or more amino acids within a 10Å sphere centred on the central carbon atom of the glycerol molecule in the active site (see FIG. 47) (such as one or more of the amino acid residues defined in set 1 or set 2);
iii) determining if one or more amino acid residues selected in accordance with step (ii) are highly conserved (particularly are active site residues and/or part of the GDSx motif and/or part of the GANDY motif); and
iv) modifying one or more amino acids selected in accordance with step (ii), excluding conserved regions identified in accordance with step (iii) in said parent sequence.

In one embodiment the amino acid residue selected may reside within a 9, preferably within a 8, 7, 6, 5, 4, or 3Å sphere centred on the central carbon atom of the glycerol molecule in the active site (see FIG. 47).

Alternatively to, or in combination with, the structural homology mapping described above, the structural homology mapping can be performed by selecting specific loop regions (LRs) or intervening regions (IVRs) derived from the pfam alignment (Alignment 2, FIG. 48) overlaid with the P10480 model and 1IVN. The loop regions (LRs) or intervening regions (IVRs) are defined in the Table below:

|  | P10480 amino acid positions (SEQ ID No 34) |
| --- | --- |
| IVR1 | 1-19 |
| Loop1 (LR1) | 20-41 |
| IVR2 | 42-76 |
| Loop2 (LR2) | 77-89 |
| IVR3 | 90-117 |
| Loop3 (LR3) | 118-127 |
| IVR4 | 128-145 |
| Loop4 (LR4) | 146-176 |
| IVR5 | 177-207 |
| Loop5 (LR5) | 208-287 |
| IVR6 | 288-317 |

In some embodiments of the present invention the variant acyltransferase enzyme for use in the methods and uses of the present invention not only comprises an amino acid modifications at one or more of the amino acids defined in any one of sets 1-4 and 6-7, but also comprises at least one amino acid modification in one or more of the above defined intervening regions (IVR1-6) (preferably in one or more of the IVRs 3, 5 and 6, more preferably in IVR 5 or IVR 6) and/or in one or more of the above-defined loop regions (LR1-5) (preferably in one or more of LR1, LR2 or LR5, more preferably in LR5).

In one embodiment, the variant acyltransferase for use in the methods and uses of the present invention may comprise one or more amino acid modification which is not only defined by one or more of set 2, 4, 6 and 7, but also is within one or more of the IVRs 1-6 (preferably within IVR 3, 5 or 6, more preferably within in IVR 5 or IVR 6) or within one or more of the LRs 1-5 (preferably within LR1, LR2 or LR5, more preferably within LR5).

Suitably, the variant acyltransferase for use in the methods and uses of the present invention may comprise one or more amino acid modification which is not only in set 1 or 2, but also is within IVR 3.

Suitably, the variant acyltransferase for use in the methods and uses of the present invention may comprise one or more amino acid modification which is not only in set 1 or 2, but also is within IVR 5.

Suitably, the variant acyltransferase for use in the methods and uses of the present invention may comprise one or more amino acid modification which is not only in set 1 or 2, but also is within IVR 6.

Suitably, the variant acyltransferase for use in the methods and uses of the present invention may comprise one or more amino acid modification which is not only in set 1 or 2, but also is within LR 1.

Suitably, the variant acyltransferase for use in the methods and uses of the present invention may comprise one or more amino acid modification which is not only in set 1 or 2, but also is within LR 2.

Likewise, in some embodiments of the present invention the variant acyltransferase enzyme for use in the methods and uses of the present invention not only comprises an amino acid modification at one or more amino acid residues which reside within a 10, preferably within a 9, 8, 7, 6, 5, 4, or 3, Å sphere centred on the central carbon atom of the glycerol molecule in the active site (see FIG. 47), but also comprises at least one amino acid modification in one or more of the above defined intervening regions (IVR1-6) (preferably in one or more of IVRs 3, 5 and 6, more preferably in IVR 5 or IVR 6) and/or in one or more of the above-defined loop regions (LR1-5) (preferably in one or more of LR1, LR2 or LR5, more preferably in LR5).

In one embodiment, preferably the amino acid modification is at one or more amino acid residues which reside within a 10Å sphere and also within LR5.

Thus, the structural homology mapping may comprise one or more of the following steps:
  i) aligning a parent sequence with a structural model (1IVN.PDB) shown in FIG. 46;
  ii) selecting one or more amino acid residue within a 10Å sphere centred on the central carbon atom of the glycerol molecule in the active site (see FIG. 47) (such as one or more of the amino acid residues defined in set 1 or set 2); and/or selecting one or more amino acid residues within IVR1-6) (preferably within IVR 3, 5 or 6, more preferably within in IVR 5 or IVR 6); and/or selecting one or more amino acid residues within LR1-5 (preferably within LR1, LR2 or LR5, more preferably within LR5); and
  iii) modifying one or more amino acids selected in accordance with step (ii) in said parent sequence.

In one embodiment the amino acid residue selected may reside within a 9Å sphere, preferably within an 8, 7, 6, 5, 4, or 3Å sphere centred on the central carbon atom of the glycerol molecule in the active site (see FIG. 47).

Suitably, the structural homology mapping may comprise one or more of the following steps:
  i) aligning a parent sequence with a structural model (1IVN.PDB) shown in FIG. 46;
  ii) selecting one or more amino acids within a 10Å sphere centred on the central carbon atom of the glycerol molecule in the active site (see FIG. 47) (such as one or more of the amino acid residues defined in set 1 or set 2); and/or selecting one or more amino acid residues within IVR1-6) (preferably within IVR 3, 5 or 6, more preferably within in IVR 5 or IVR1-6); and/or selecting one or more amino acid residues within LR1-5 (preferably within LR1, LR2 or LR5, more preferably within LR5);
  iii) determining if one or more amino acid residues selected in accordance with step (ii) are highly conserved (particularly are active site residues and/or part of the GDSx motif and/or part of the GANDY motif); and
modifying one or more amino acids selected in accordance with step (ii), excluding conserved regions identified in accordance with step (iii) in said parent sequence.

Suitably, the one or more amino acids selected in the methods detailed above are not only within a 10Å sphere centred on the central carbon atom of the glycerol molecule in the active site (see FIG. 47) (such as one or more of the amino acid residues defined in set 1 or set 2), but are also within one or more of the IVRs 1-6 (preferably within IVR 3, 5 or 6, more preferably within in IVR 5 or IVR 6) or within one or more of the LRs 1-5 (preferably within LR1, LR2 or LR5, more preferably within LR5).

In one embodiment, preferably the one or more amino acid modifications is/are within LR5. When it is the case that the modification(s) is within LR5, the modification is not one which is defined in set 5. Suitably, the one or more amino acid modifications not only fall with the region defined by LR5, but also constitute an amino acid within one or more of set 2, set 4, set 6 or set 7.

Suitably, the sequence homology alignment may comprise one or more of the following steps:
  i) selecting a first parent lipid acyltransferase;
  ii) identifying a second related lipid acyltransferase having a desirable activity;
  iii) aligning said first parent lipid acyltransferase and the second related lipid acyltransferase;
  iv) identifying amino acid residues that differ between the two sequences; and
  v) modifying one or more of the amino acid residues identified in accordance with step (iv) in said parent lipid acyltransferase.

Suitably, the sequence homology alignment may comprise one or more of the following steps:
  i) selecting a first parent lipid acyltransferase;
  ii) identifying a second related lipid acyltransferase having a desirable activity;
  iii) aligning said first parent lipid acyltransferase and the second related lipid acyltransferase;
  iv) identifying amino acid residues that differ between the two sequences;
  v) determining if one or more amino acid residues selected in accordance with step (iv) are highly conserved (particularly are active site residues and/or part of the GDSx motif and/or part of the GANDY motif); and
  vi) modifying one or more of the amino acid residues identified in accordance with step (iv) excluding conserved regions identified in accordance with step (v) in said parent sequence.

Suitably, said first parent lipid acyltransferase may comprise any one of the following amino acid sequences: SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32 or SEQ ID No. 33.

Suitably, said second related lipid acyltransferase may comprise any one of the following amino acid sequences: SEQ ID No. 3, SEQ ID No. 34, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 32 or SEQ ID No. 33.

The variant enzyme must comprise at least one amino acid modification compared with the parent enzyme. In some embodiments, the variant enzyme may comprise at least 2, preferably at least 3, preferably at least 4, preferably at least 5, preferably at least 6, preferably at least 7, preferably at least 8, preferably at least 9, preferably at least 10 amino acid modifications compared with the parent enzyme.

When referring to specific amino acid residues herein the numbering is that obtained from alignment of the variant sequence with the reference sequence shown as SEQ ID No. 34 or SEQ ID No. 35.

In one aspect preferably the variant enzyme comprises one or more of the following amino acid substitutions:
S3A, C, D, E, F, G, H, I, K, L, M, N, P, Q, R, T, V, W, or Y; and/or
L17A, C, D, E, F, G, H, I, K, M, N, P, Q, R, S, T, V, W, or Y; and/or
S18A, C, D, E, F, H, I, K, L, M, N, P, Q, R, T, W, or Y; and/or
K22A, C, D, E, F, G, H, I, L, M, N, P, Q, R, S, T, V, W, or Y; and/or
M23A, C, D, E, F, G, H, I, K, L, N, P, Q, R, S, T, V, W, or Y; and/or Y30A, C, D, E, G, H, I, K, L, M, N, P, Q, R, S, T, V, or W; and/or
G40A, C, D, E, F, H, I, K, L, M, N, P, Q, R, S, T, V, W, or Y; and/or
N80A, C, D, E, F, G, H, I, K, L, M, P, Q, R, S, T, V, W, or Y; and/or
P81A, C, D, E, F, G, H, I, K, L, M, N, Q, R, S, T, V, W, or Y; and/or
K82A, C, D, E, F, G, H, I, L, M, N, P, Q, R, S, T, V, W, or Y; and/or
N87A, C, D, E, F, G, H, I, K, L, M, P, Q, R, S, T, V, W, or Y; and/or
N88A, C, D, E, F, G, H, I, K, L, M, P, Q, R, S, T, V, W, or Y; and/or
W111A, C, D, E, F, G, H, I, K, L, M, N, P, Q, R, S, T, V, W or Y; and/or
V112A, C, D, E, F, G, H, I, K, L, M, N, P, Q, R, S, T, W, or Y; and/or
A114C, D, E, F, G, H, I, K, L, M, N, P, Q, R, S, T, V, W, or Y; and/or
Y117A, C, D, E, F, G, H, I, K, L, M, N, P, Q, R, S, T, V, or W; and/or
L118A, C, D, E, F, G, H, I, K, M, N, P, Q, R, S, T, V, W, or Y; and/or
P156A, C, D, E, F, G, H, I, K, L, M, N, Q, R, S, T, V, W, or Y; and/or
D157A, C, E, F, G, H, I, K, L, M, P, Q, R, S, T, V, W, or Y; and/or
G159A, C, D, E, F, H, I, K, L, M, N, P, Q, R, S, T, V, W, or Y; and/or
Q160A, C, D, E, F, G, H, I, K, L, M, N, P, R, S, T, V, W, or Y; and/or
N161A, C, D, E, F, G, H, I, K, L, M P, Q, R, S, T, V, W, or Y; and/or
P162A, C, D, E, F, G, H, I, K, L, M, N, Q, R, S, T, V, W, or Y; and/or
S163A, C, D, E, F, G, H, I, K, L, M, N, P, Q, R, T, V, W, or Y; and/or
A164C, D, E, F, G, H, I, K, L, M, N, P, Q, R, S, T, V, W, or Y; and/or
R165A, C, D, E, F, G, H, I, K, L, M, N, P, Q, S, T, V, W, or Y; and/or
S166A, C, D, E, F, G, H, I, K, L, M, N, P, Q, R, T, V, W, or Y; and/or
Q167A, C, D, E, F, G, H, I, K, L, M, N, P, R, S, T, V, W, or Y; and/or
K168A, C, D, E, F, G, H, I, L, M, N, P, Q, R, S, T, V, W, or Y; and/or
V169A, C, D, E, F, G, H, I, K, L, M, N, P, Q, R, S, T, W, or Y; and/or
V170A, C, D, E, F, G, H, I, K, L, M, N, P, Q, R, S, T, W, or Y; and/or
E171A, C, D, F, G, H, I, K, L, M, N, P, Q, R, S, T, V, W, or Y; and/or
A172C, D, E, F, G, H, I, K, L, M, N, P, Q, R, S, T, V, W, or Y; and/or
Y179A, C, D, E, F, G, H, I, K, L, M, N, P, Q, R, S, T, V, or W; and/or
H180A, C, D, E, F, G, I, K, L, M, P, Q, R, S, T, V, W, or Y; and/or
N181A, C, D, E, F, G, H, I, K, L, M, P, Q, R, S, T, V, W, or Y; and/or
Q182A, C, D, E, F, G, H, I, K, L, M, N, P, R, S, T, V, W, or Y, preferably K; and/or
M209A, C, D, E, F, G, H, I, K, L, N, P, Q, R, S, T, V, W, or Y; and/or
L210 A, C, D, E, F, G, H, I, K, M, N, P, Q, R, S, T, V, W, or Y; and/or
R211 A, C, D, E, F, G, H, I, K, L, M, N, P, Q, R, S, T, V, W, or Y; and/or
N215 A, C, D, E, F, G, H, I, K, L, M, N, P, Q, R, S, T, V, W, or Y; and/or
Y226A, C, D, E, G, H, I, K, L, M, N, P, Q, R, S, T, V, or W; and/or
Y230A, C, D, E, G, H, I, K, L, M, N, P, Q, R, S, T, V or W; and/or
K284A, C, D, E, F, G, H, I, L, M, N, P, Q, R, S, T, V, W, or Y; and/or
M285A, C, D, E, F, G, H, I, K, L, N, P, Q, R, S, T, V, W, or Y; and/or
Q289A, C, D, E, F, G, H, I, K, L, M, N, P, R, S, T, V, W, or Y; and/or
V290A, C, D, E, F, G, H, I, K, L, M, N, P, Q, R, S, T, W, or Y; and/or
E309A, C, D, F, G, H, I, K, L, M, N, P, Q, R, S, T, V, W, or Y; and/or
S310A, C, D, E, F, G, H, I, K, L, M, N, P, Q, R, T, V, W, or Y.

In addition or alternatively thereto there may be one or more C-terminal extensions. Preferably the additional C-terminal extension is comprised of one or more aliphatic amino acids, preferably a non-polar amino acid, more preferably of I, L, V or G. Thus, the present invention further provides for a variant enzyme comprising one or more of the following C-terminal extensions: 318I, 318L, 318V, 318G.

When it is the case that the residues in the parent backbone differ from those in P10480 (SEQ ID No. 2), as determined by homology alignment and/or structural alignment to P10480 and/or 1IVN, it may be desirable to replace the residues which align to any one or more of the following amino acid residues in P10480 (SEQ ID No. 2): Ser3, Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309 or Ser310, with the residue found in P10480 respectively.

Variant enzymes which have a decreased hydrolytic activity against a phospholipid, such as phosphatidylcholine (PC), may also have an increased transferase activity from a phospholipid.

Variants enzymes which have an increased transferase activity from a phospholipid, such as phosphatidylcholine (PC), may also have an increased hydrolytic activity against a phospholipid.

Suitably, one or more of the following sites may be involved in substrate binding: Leu17; Ala114; Tyr179; His180; Asn181; Met209; Leu210; Arg211; Asn215; Lys284; Met285; Gln289; Val290.

1. Modification of One or More of the Following Residues May Result in a Variant Enzyme Having an Increased Absolute Transferase Activity Against Phospholipid:
S3, D157, S310, E309, Y179, N215, K22, Q289, M23, H180, M209, L210, R211, P81, V112, N80, L82, N88; N87

Specific modifications which may provide a variant enzyme having an improved transferase activity from a phospholipid may be selected from one or more of the following:
S3A, C, D, E, F, G, H, I, K, L, M, N, P, Q, R, T, V, W or Y; preferably N, E, K, R, A, P or M, most preferably S3A
D157A, C, E, F, G, H, I, K, L, M, N, P, Q, R, S, T, V, W or Y; preferably D157S, R, E, N, G, T, V, Q, K or C
S310A, C, D, E, F, G, H, I, K, L, M, N, P, Q, R, T, V, W or Y; preferably S310T –318 E E309 A, C, D, E, F, G, H, I, K, L, M, N, P, Q, R, T, V, W or Y; preferably E309 R, E, L, R or A Y179 A, C, D, E, F, G, H, I, K, L, M, N, P, Q, R, S, T, V or W; preferably Y179 D, T, E, R, N, V, K, Q or S, more preferably E, R, N, V, K or Q N215 A, C, D, E, F, G, H, I, K, L, M, N, P, Q, R, S, T, V, W or Y; preferably N215 S, L, R or Y K22 A, C, D, E, F, G, H, I, L, M, N, P, Q, R, S, T, V, W or Y; preferably K22 E, R, C or A Q289 A, C, D, E, F, G, H, I, K, L, M, N, P, R, S, T, V, W or Y; preferably Q289 R, E, G, P or N M23 A, C, D, E, F, G, H, I, K, L N, P, Q, R, S, T, V, W or Y; preferably M23 K, Q, L, G, T or S H180 A, C, D, E, F, G, I, K, L, M, P, Q, R, S, T, V, W or Y; preferably H180 Q, R or K M209 A, C, D, E, F, G, H, I, K, L, N, P, Q, R, S, T, V, W or Y; preferably M209 Q, S, R, A, N, Y, E, V or L L210 A, C, D, E, F, G, H, I, K, M, N, P, Q, R, S, T, V, W or Y; preferably L210 R, A, V, S, T, I, W or M R211 A, C, D, E, F, G, H, I, K, L, M, N, P, Q, S, T, V, W or Y; preferably R211T P81 A, C, D, E, F, G, H, I, K, L, M, N, Q, R, S, T, V, W or Y; preferably P81G V112 A, C, D, E, F, G, H, I, K, L, M, N, P, Q, R, S, T, W or Y; preferably V112C N80 A, C, D, E, F, G, H, I, K, L, M, P, Q, R, S, T, V, W or Y; preferably N80 R, G, N, D, P, T, E, V, A or G L82 A, C, D, E, F, G, H, I, M, N, P, Q, R, S, T, V, W or Y; preferably L82 N, S or E N88 A, C, D, E, F, G, H, I, K, L, M, P, Q, R, S, T, V, W or Y; preferably N88C N87 A, C, D, E, F, G, H, I, K, L, M, P, Q, R, S, T, V, W or Y; preferably N87 M or G Modification of one or more of the following residues results in a variant enzyme having an increased absolute transferase activity against phospholipid:

S3 N, R, A, G
M23 K, Q, L, G, T, S
H180 R
L82 G
Y179 E, R, N, V, K or Q
E309 R, S, L or A

One preferred modification is N80D. This is particularly the case when using the reference sequence SEQ ID No. 35. Therefore in a preferred embodiment of the present invention the lipid acyltransferase according to the present invention comprises SEQ ID No. 35.

As noted above, when referring to specific amino acid residues herein the numbering is that obtained from alignment of the variant sequence with the reference sequence shown as SEQ ID No. 34 or SEQ ID No. 35

Much by preference, the lipid acyltransferase for use in the method and uses of the present invention may be a lipid acyltransferase comprising the amino acid sequence shown as SEQ ID No. 16 (FIG. 10), or an amino acid sequence which has 75% or more, preferably 85% or more, more preferably 90% or more, even more preferably 95% or more, even more preferably 98% or more, or even more preferably 99% or more identity to SEQ ID No. 16. This enzyme may be considered a variant enzyme.

For the avoidance of doubt, when a particular amino acid is taught at a specific site, for instance L118 for instance, this refers to the specific amino acid at residue number 118 in SEQ ID No. 34 unless otherwise stated. However, the amino acid residue at site 118 in a different parent enzyme may be different from leucine.

Thus, when taught to substitute an amino acid at residue 118, although reference may be made to L118 it would be readily understood by the skilled person that when the parent enzyme is other than that shown in SEQ ID No. 34, the amino acid being substituted may not be leucine. It is, therefore, possible that when substituting an amino acid sequence in a parent enzyme which is not the enzyme having the amino acid sequence shown as SEQ ID No. 34, the new (substituting) amino acid may be the same as that taught in SEQ ID No. 34. This may be the case, for instance, where the amino acid at say residue 118 is not leucine and is, therefore different from the amino acid at residue 118 in SEQ ID No. 34. In other words, at residue 118 for example, if the parent enzyme has at that position an amino acid other than leucine, this amino acid may be substituted with leucine in accordance with the present invention.

For the purposes of the present invention, the degree of identity is based on the number of sequence elements which are the same. The degree of identity in accordance with the present invention may be suitably determined by means of computer programs known in the art, such as GAP provided in the GCG program package (Program Manual for the Wisconsin Package, Version 8, August 1994, Genetics Computer Group, 575 Science Drive, Madison, Wis., US 53711) (Needleman & Wunsch (1970), J. of Molecular Biology 48, 443-45) using the following settings for polypeptide sequence comparison: GAP creation penalty of 3.0 and GAP extension penalty of 0.1. Suitably, the degree of identity with regard to an amino acid sequence is determined over at least 20 contiguous amino acids, preferably over at least 30 contiguous amino acids, preferably over at least 40 contiguous amino acids, preferably over at least 50 contiguous amino acids, preferably over at least 60 contiguous amino acids.

Suitably, the lipid acyltransferase enzyme according to the present invention may be obtainable, preferably obtained, from organisms from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium.*

Suitably, the lipid acyltransferase enzyme according to the present invention may be obtainable, preferably obtained, from one or more of the following organisms: *Aeromonas hydrophila, Aeromonas salmonicida, Streptomyces coelicolor, Streptomyces rimosus, Mycobacterium, Streptococcus pyogenes, Lactococcus lactis, Streptococcus pyogenes, Streptococcus thermophilus, Streptomyces thermosacchari, Streptomyces avermitilis Lactobacillus helveticus, Desulfitobacterium dehalogenans, Bacillus* sp, *Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis Thermobda fusca* and *Corynebacterium efciens.*

In one aspect, preferably the lipid acyltransferase enzyme according to the present invention is obtainable, preferably obtained, from one or more of *Aeromonas hydrophila* or *Aeromonas salmonicida.*

In one embodiment suitably the sterol and/or stanol may comprise one or more of the following structural features:
i) a 3-beta hydroxy group or a 3-alpha hydroxy group; and/or
ii) A:B rings in the cis position or A:B rings in the trans position or C5-C6 is unsaturated.

Suitable sterol acyl acceptors include cholesterol and phytosterols, for example alpha-sitosterol, beta-sitosterol, stigmasterol, ergosterol, campesterol, 5,6-dihydrosterol, brassicasterol, alpha-spinasterol, beta-spinasterol, gamma-spinasterol, deltaspinasterol, fucosterol, dimosterol, ascosterol, serebisterol, episterol, anasterol, hyposterol, chondrillasterol, desmosterol, chalinosterol, poriferasterol, clionasterol, sterol glycosides, tocopherol, tocotrienol and other natural or synthetic isomeric forms and derivatives.

Advantageously, in one embodiment, the sterol acyl acceptor is tocopherol. Suitably the tocopherol may be one or more of gamma, delta, beta or d-alpha tocopherol—including d-alpha tocopherol acid succinate for example. In one embodiment, preferably the sterol acyl acceptor is alpha-tocopherol.

In one embodiment, preferably the method according to the present invention includes the step of adding tocopherol, preferably alpha-tocopherol, to the oil.

In one aspect, preferably the sterol acyl acceptor is cholesterol.

In one aspect, preferably the sterol and/or stanol acyl acceptor is a sterol and/or a stanol other than cholesterol.

In one aspect of the present invention suitably more than one sterol and/or stanol may act as the acyl acceptor, suitably more than two sterols and/or stanols may act as the acyl acceptor. In other words, in one aspect of the present invention, suitably more than one sterol ester and/or stanol ester may be produced. Suitably, when cholesterol is the acyl acceptor one or more further sterols or one or more stanols may also act as the acyl acceptor. Thus, in one aspect, the present invention provides a method for the in situ production of both a tocopherol ester and at least one other sterol or stanol ester in combination. In other words, the lipid acyltransferase for some aspects of the present invention may transfer an acyl group from a lipid to both tocopherol and at least one further sterol and/or at least one stanol.

In some aspects, the oil prepared in accordance with the present invention may be used to reduce the risk of cardiovascular diseases.

In one aspect, the oil prepared in accordance with the present invention may be used to reduce blood serum cholesterol and/or to reduce low density lipoprotein. Blood serum cholesterol and low density lipoproteins have both been associated with certain diseases in humans, such as atherosclerosis and/or heart disease for example. Thus, it is envisaged that the oils prepared in accordance with the present invention may be used to reduce the risk of such diseases.

In another aspect the present invention provides the use of an edible oil according to the present invention for use in the treatment and/or prevention of cardiovascular diseases.

Thus, in one aspect the present invention provides the use of an edible oil according to the present invention for use in the treatment and/or prevention of atherosclerosis and/or heart disease.

In a further aspect, the present invention provides a medicament comprising an edible oil according to the present invention.

In a further aspect, the present invention provides a method of treating and/or preventing a disease in a human or animal patient which method comprising administering to the patient an effective amount of an edible oil according to the present invention.

Suitably the sterol acyl acceptor may be one which is naturally found in edible or vegetable oils.

Alternatively, or in addition, the sterol acyl acceptor may be one which added to the edible or vegetable oil.

When it is the case that a sterol and/or a stanol is added to the edible oil, the sterol and/or stanol may be added before, simultaneously with, and/or after the addition of the lipid acyltransferase according to the present invention. Suitably, the present invention may encompass the addition of exogenous sterols/stanols, particularly phytosterols/phytostanols, to an edible or vegetable oil prior to or simultaneously with the addition of the enzyme according to the present invention.

For some aspects, one or more sterols present in the edible oil may be converted to one or more stanols prior to or at the same time as the lipid acyltransferase is added according to the present invention. Any suitable method for converting sterols to stanols may be employed. For example, the conversion may be carried out by chemical hydrogenation for example. The conversion may be conducted prior to the addition of the lipid acyltransferase in accordance with the present invention or simultaneously with the addition of the lipid acyltransferase in accordance with the present invention. Suitably enzymes for the conversion of sterols to stanols are taught in WO00/061771.

Suitably the present invention may be employed to produce phytostanol esters in situ in an edible oil. Phytostanol esters have increased solubility through lipid membranes, bioavailability and enhanced health benefits (see for example WO92/99640).

An advantage of the present invention is that sterol and/or stanol esters are produced in the edible oil during the degumming thereof. A further advantage is that enzyme is degummed without an increase, or a substantial, increase, in the free fatty acid content of the edible oil. The production of free fatty acids can be detrimental in the edible oil. Preferably, the method according to the present invention results in the degumming of an edible oil wherein the accumulation of free fatty acids is reduced and/or eliminated. Without wishing to be bound by theory, in accordance with the present invention the fatty acid which is removed from the lipid is transferred by the lipid acyltransferase to an acyl acceptor, for example a sterol and/or a stanol. Thus, the overall level of free fatty acids in the foodstuff does not increase or increases only to an insignificant degree. This is in sharp contradistinction to the situation when phospholipases, such as Lecitase Ultra™ are used in enzymatic degumming of edible oils. In particular, the use of such phospholipases can result in an increased amount of free fatty acid in the edible oil, which can be detrimental. In accordance with the present invention, the accumulation of free fatty acids is reduced and/or eliminated when compared with the amount of free fatty acids which would have been accumulated had a phospholipase A enzyme, such as Lecitase Ultra™, been used in place of the lipid acyltransferase in accordance with the present invention.

A lipid acyl transferase according to the present invention may be suitable for use in the enzymatic degumming of vegetable or edible oils. In processing of vegetable or edible oil the edible or vegetable oil is treated with a lipid acyl transferase according to the present invention so as to hydrolyse a major part of the phospholipid. Preferably, the fatty acyl groups are transferred from the polar lipids to an acyl acceptor. The degumming process typically results in the reduction of the content of the polar lipids, particularly of phospholipids, in an edible oil due to hydrolysis of a major part (i.e. more than 50%) of the phospholipid. Typically, the aqueous phase containing the hydrolysed phospholipid is separated from the oil. Suitably, the edible or vegetable oil may initially (pretreatment with the enzyme according to the present invention) have a phosphorus content of 50-250 ppm.

As the skilled person is aware, the term "degumming" as used herein means the refining of oil by converting phosphatides (such as lecithin, phospholipids and occluded oil) into hydratable phosphatides. Oil which has been degummed is more fluid and thus has better handling properties than oil which has not been degummed.

The term "transferase" as used herein is interchangeable with the term "lipid acyltransferase".

Suitably, the lipid acyltransferase as defined herein catalyses one or more of the following reactions: interesterification, transesterification, alcoholysis, hydrolysis. The term "interesterification" refers to the enzymatic catalysed transfer of acyl groups between a lipid donor and lipid acceptor, wherein the lipid donor is not a free acyl group.

The term "transesterification" as used herein means the enzymatic catalysed transfer of an acyl group from a lipid donor (other than a free fatty acid) to an acyl acceptor (other than water).

As used herein, the term "alcoholysis" refers to the enzymatic cleavage of a covalent bond of an acid derivative by reaction with an alcohol ROH so that one of the products combines with the H of the alcohol and the other product combines with the OR group of the alcohol.

As used herein, the term "alcohol" refers to an alkyl compound containing a hydroxyl group.

As used herein, the term "hydrolysis" refers to the enzymatic catalysed transfer of an acyl group from a lipid to the OH group of a water molecule.

The term "without increasing or without substantially increasing the free fatty acids" as used herein means that preferably the lipid acyl transferase according to the present invention has 100% transferase activity (i.e. transfers 100% of the acyl groups from an acyl donor onto the acyl acceptor, with no hydrolytic activity); however, the enzyme may transfer less than 100% of the acyl groups present in the lipid acyl donor to the acyl acceptor. In which case, preferably the acyltransferase activity accounts for at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity. The % transferase activity (i.e. the transferase activity as a percentage of the total enzymatic activity) may be determined by the following protocol:

Enzyme suitable for use in the methods of the invention preferably have phospholipase activity in a standard phospholipase activity assay taught hereinbelow.

Determination of Phospholipase Activity (Phospholipase Activity Assay (PLU-7)):

Substrate 0.6% L-α Phosphatidylcholine 95% Plant (Avanti #441601), 0.4% Triton-X 100 (Sigma X-100) and 5 mM $CaCl_2$ was dispersed in 0.05M HEPES buffer pH 7.

Assay Procedure:

400 µl, substrate was added to a 1.5 mL Eppendorf tube and placed in an Eppendorf Thermomixer at 37° C. for 5 minutes. At time t=0 min, 50 µL enzyme solution was added. Also a blank with water instead of enzyme was analyzed. The sample was mixed at 10×100 rpm in an Eppendorf Thermomixer at 37° C. for 10 minutes. At time t=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-7 at pH 7 was calculated as micromole fatty acid produced per minute under assay conditions.

More preferably the lipid acyl-transferase will also have transferase activity as defined by the protocol below:

Protocol for the Determination of % Acyltransferase Activity:

An edible oil to which a lipid acyltransferase according to the present invention has been added may be extracted following the enzymatic reaction with $CHCl_3:CH_3OH$ 2:1 and the organic phase containing the lipid material is isolated and analysed by GLC and HPLC according to the procedure detailed hereinbelow. From the GLC and HPLC analyses the amount of free fatty acids and one or more of sterol/stanol esters; are determined. A control edible oil to which no enzyme according to the present invention has been added, is analysed in the same way.

Calculation:

From the results of the GLC and HPLC analyses the increase in free fatty acids and sterol/stanol esters can be calculated:

Δ% fatty acid=% Fatty acid(enzyme)−% fatty acid (control); $Mv$ fatty acid=average molecular weight of the fatty acids;

$A$ΔA % sterol ester/$Mv$ sterol ester (where Δ% sterol ester=% sterol/stanol ester(enzyme)−% sterol/stanol ester(control) and $Mv$ sterol ester=average molecular weight of the sterol/stanol esters);

The transferase activity is calculated as a percentage of the total enzymatic activity:

$$\% \text{ transferase activity} = \frac{A \times 100}{A + \Delta \% \text{ fatty acid}/(Mv \text{ fatty acid})}$$

If the free fatty acids are increased in the edible oil they are preferably not increased substantially, i.e. to a significant degree. By this we mean, that the increase in free fatty acid does not adversely affect the quality of the edible oil.

The edible oil used for the acyltransferase activity assay is preferably the soya bean oil supplemented with plant sterol (1%) and phosphatidylcholine (2%) oil using the method in Example 3. For the assay the enzyme dosage used is preferably 0.2 PLU-7/g oil, more preferably 0.08 PLU-7/g oil. The level of phospholipid present in the oil and/or the % conversion of sterol is preferably determined after 4 hours, more preferably after 20 hours.

In some aspects of the present invention, the term "without substantially increasing free fatty acids" as used herein means that the amount of free fatty acid in a edible oil treated with an lipid acyltransferase according to the present invention is less than the amount of free fatty acid produced in the edible oil when an enzyme other than a lipid acyltransferase according to the present invention had been used, such as for example as compared with the amount of free fatty acid produced when a conventional phospholipase enzyme, e.g. Lecitase Ultra™ (Novozymes A/S, Denmark), had been used.

In addition to, or instead of, assessing the % transferase activity in an oil (above), to identify the lipid acyl transferase enzymes most preferable for use in the methods of the invention the following assay entitled "Protocol for identifying lipid acyltransferases for use in the present invention" can be employed.

Protocol for Identifying Lipid Acyltransferases

A lipid acyltransferase in accordance with the present invention is on which results in:

i) the removal of phospholipid present in a soya bean oil supplemented with plant sterol (1%) and phosphatidylcholine (2%) oil using the method taught in Example 3. and/or ii) the conversion (% conversion) of the added sterol to sterol-ester when using the method taught in Example 3.

The GLC method for determining the level of sterol and sterol esters as taught in Example 5 may be used.

For the assay the enzyme dosage used may be 0.2 PLU-7/g oil, preferably 0.08 PLU-7/g oil. The level of phospholipid present in the oil and/or the conversion (% conversion) of sterol is preferably determined after 4 hours, more preferably after 20 hours.

In the protocol for identifying lipid acyl transferases, after enzymatic treatment, 5% water is preferably added and thoroughly mixed with the oil. The oil is then separated into an oil and water phase using centrifugation (see "Enzyme-catalyzed degumming of vegetable oils" by Buchold, H. and Laurgi A.-G., Fett Wissenschaft Technologie (1993), 95(8), 300-4, ISSN: 0931-5985), and the oil phase can then be analysed for phosphorus content using the following protocol ("Assay for Phosphorus Content"):

Assay for Phosphorus Content

The level of phospholipid present in an oil after degumming is determined by first preparing the oil sample according to the sample preparation taught in the AOAC Official Method 999.10 (>Lead, Cadmium, Zinc, Copper, and Iron in Foods Atomic Absorption Spectrophotometry after Microwave Digestion, First Action 1999 NMKL-AOAC Method). The amount of phospholipids in the oil is then measured by analysing the phosphorus content in the oil sample after degumming according to the AOAC Official Method 985.01 (>Metals and Other Elements in Plants and Pet Foods Inductively Coupled Plasma Spectroscopic Method First Action 1985 Final Action 1988).

The amount of phosphorus present in the oil after degumming is preferably less than 50 ppm, preferably less than 40 ppm, preferably less than 30 ppm, preferably less than 20 ppm, preferably less than 10 ppm, preferably less than 5 ppm. The oil after degumming, as illustrated in the examples may be substantially free of phospholipid, i.e. contain less than 1 ppm phospholipid.

The % conversion of the sterol present in the oil is at least 1%, preferably at least 5%, preferably at least 10%, preferably at least 20%, preferably at least 30%, preferably at least 40%, preferably at least 50%, preferably at least 60%, preferably at least 70%, preferably at least 80%, preferably at least 90%, preferably at least 95%.

In one embodiment the % conversion of the sterol present in the oil is at least 5%, preferably at least 20%.

Low Water Degumming

It has surprisingly been found that when a lipid acyl transferase is used in a process of enzymatic degumming of an edible oil, the enzymatic degumming can be performed in a very low water environment. Some water may still be required, for example when adding the enzyme to the oil the enzyme may be added in small amount of water, such as less than 1%, preferably 0.5%, more preferably less than 0.2%, more preferably less than 1%.

Preferably the water content of the edible oil in the processes and uses according to the present invention is less than 1%, preferably less than 0.5%, more preferably less than 0.2%, more preferably less than 0.1%.

Thus, one advantage of the present invention is that when only a small amount of water (i.e. <5%, preferably <1%, preferably <0.5%, preferably <0.2%) is used during the enzymatic degumming the gums (i.e. the phosphorus containing portion) separates from the oil, for example in the form of a solid precipitate. The solid precipitate can be readily removed from the degummed oil by methods such as simply decanting the oil or removing or the gum by filtration for example.

This contrasts sharply with conventional enzymatic degumming processes in which a significant amount of water is added to the oil. This is because in the conventional enzymatic degumming processes post-degumming because of the high water content, one obtains a water layer which comprises the phosphorus containing portion (for example that portion comprising lysophospholipids). This water lay must be removed and can be removed by centrifugation for example. However, the removal of the water layer is significantly more difficult that the removal of the solid precipitate obtained when using the process of the present invention.

Therefore the enzymatic degumming process according to the present invention could be considered as a "low water degumming process".

In one embodiment of the present invention, the gum may be removed by adjusting the oil to 5% water followed by centrifugation of the oil. (see "Enzyme-catalyzed degumming of vegetable oils" by Buchold, H. and Laurgi A.-G., Fett Wissenschaft Technologie (1993), 95(8), 300-4).

Therefore, the invention provides a process for the degumming of an edible oil, such as a crude edible oil (for example a crude soya oil), without the need for either a prewashing step prior to degumming and/or a step of removing the water added during degumming, which is required when using conventional phospholipases such as pancreatic phospholipase and Lecitase Ultra™.

Preferably, the edible oil has a less than a 4.5% water content, more preferably less than 4%, less than 3%, less than 2%, less than 1%, less than 0.5%.

Suitably, the edible oil may contain at least 0.1% water, such as at least 0.3%, 0.4% or 0.5%.

Preferred lipid acyltransferases for use in the present invention are identified as those which have a high activity such as high phospholipid hydrolytic activity or high phospholipid transferase activity on phospholipids in an oil environment, most preferably lipid acyl transferases for use in enzymatic degumming have a high phospholipid to sterol transferase activity.

As detailed above, other acyl-transferases suitable for use in the methods of the invention may be identified by identifying the presence of the GDSx, GANDY and HPT blocks either by alignment of the pFam00657 consensus sequence (SEQ ID No 1), and/or alignment to a GDSx acyltransferase, for example SEQ ID No 28. In order to assess their suitability for degumming, i.e. identify those enzymes which have a transferase activity of at least 5%, more preferably at least 10%, more preferably at least 20%, more preferably at least 30%, more preferably at least 40%, more preferably 50%, more preferably at least 60%, more preferably at least 70%, more preferably at least 80%, more preferably at least 90% and more preferably at least 98% of the total enzyme activity, such acyltransferases are tested using the "Protocol for the determination of % acyltransferase activity" assay detailed hereinabove.

The present invention relates to the use of a lipid acyl transferase according to the present invention in degumming edible vegetable oils and/or edible oils and to methods for degumming edible or vegetable oils.

In one aspect, the present invention may provide a method comprising using a lipid acyl transferase to remove the non-hydratable phosphorus (NHP) content in oil comprising a relatively high amount of NHP.

The term "edible oil" as uses herein may encompass vegetable oils.

Preferably, the edible oil prior to treatment in accordance with the present invention comprises a non-hydratable phosphorus content of 50-250 ppm, preferably at least 60 ppm, more preferably at least 100 ppm, and even more preferably at least 200 ppm, even more preferably above 250 ppm.

More preferably, the edible oil prior to treatment in accordance with the present invention comprises a non-hydratable phosphorous content in the range of 60-500 ppm, more preferably in the range of 100-500 ppm, and even more preferably in the range of 200-500 ppm.

An edible oil as referred to herein may be any oil having a relatively high amount of a non-hydratable phosphorus, this may include water degummed oil, or more preferably this is a crude-oil or a semi-crude oil.

In one aspect, the crude edible oil has, prior to carrying out the method of the invention, a phosphorous content above 350 ppm, more preferably above 400 ppm, even more preferably above 500 ppm, and most preferably above 600 ppm.

Oils encompassed by the method according to the present invention may include, but are not limited to, one or more of soya bean oil, canola oil, corn oil, cottonseed oil, palm oil, coconut oil, peanut oil, olive oil, safflower oil, palm kernel oil, rape seed oil and sunflower oil.

Preferably, the oil is one or more of soya bean oil, sunflower oil and rape seed oil (sometimes referred to as canola oil).

More preferably, the oil is one or more of soya bean oil, sunflower oil or rape seed oil.

Most preferably, the oil is soya bean oil.

These oils may be in the form of a crude oil, a semicrude oil, or a water-degummed oil.

As used herein, "crude oil" (also referred to herein as a non-degummed oil) may be a pressed or extracted oil or a mixture thereof from e.g. rapeseed, soybean, or sunflower. The phosphatide content in a crude oil may vary from 0.5-3% w/w corresponding to a phosphorus content in the range of 200-1200 ppm, more preferably in the range of 250-1200 ppm. Apart from the phosphatides the crude oil also contains small concentrations of carbohydrates, sugar compounds and metal/phosphatide acid complexes of Ca, Mg and Fe.

As used herein, "semicrude oil" refers to any oil which is not a crude oil, but which has a phosphatide content above 250 ppm, more preferably above 500 ppm. Such an oil could e.g. be obtained by subjecting a crude oil to a process similar to the "water degumming" process described below.

As used herein, "water-degummed oil" may be typically be obtained by a "water degumming process" comprising mixing 1-3% w/w of hot water with warm (60-90° C.) crude oil. Usual treatment periods are 30-60 minutes. The water-degumming step removes the phosphatides and mucilaginous gums which become insoluble in the oil when hydrated. The hydrated phosphatides and gums can be separated from the oil by settling, filtration or centrifugation—centrifugation being the more prevalent practice. The essential object in said water-degumming process is to separate the hydrated phosphatides from the oil. The mixing of hot water into the oil, described above, should herein be understood broadly as mixing of an aqueous solution into the oil according to standard water-degumming procedures in the art.

Advantageously, the method and uses of the present invention enable degumming of edible oils in a low water (<5%, preferably less than 2%, more preferably less than 1%) environments. Therefore degumming can be performed with adding less water than when using conventional enzymes. A further advantage of the present invention is the production of sterol esters (in particular tocopherol esters) in the oil. A yet further advantage of the present invention is removal (preferably complete removal) of phospholipids. A further advantage of the present invention is the removal (preferably complete removal) of phospholipids without removal of phytosterol, and in particular tocopherol. It is preferred that, due to the esterification of the phytosterol, there is no significant removal of phytosterols such as tocopherol from the oil instead they are simply esterified. However, in one embodiment the amount of phytosterol such as tocopherol may be reduced. In such embodiments the absolute levels of phytosterol such as tocopherol may be reduced by preferably no more than 10%, alternatively no more than 25%, alternatively no more than 50%, alternatively no more than 75%. A yet further advantage of the present invention is the removal (preferably complete removal) of phospholipids without hydrolysis of triglycerides.

For the ease of reference, these and further aspects of the present invention are now discussed under appropriate section headings. However, the teachings under each section are not necessarily limited to each particular section.

Definition of Sets
Amino Acid Set 1:
Amino Acid Set 1

Gly8, Asp9, Ser10, Leu11, Ser12, Tyr15, Gly44, Asp45, Thr46, Glu69, Leu70, Gly71, Gly72, Asn73, Asp74, Gly75, Leu76, Gln106, Ile107, Arg108, Leu109, Pro110, Tyr113, Phe121, Phe139, Phe140, Met141, Tyr145, Met151, Asp154, His157, Gly155, Ile156, Pro158

The highly conserved motifs, such as GDSx and catalytic residues, were deselected from set 1 (residues underlined). For the avoidance of doubt, set 1 defines the amino acid residues within 10Å of the central carbon atom of a glycerol in the active site of the 1IVN model.

Amino Acid Set 2:

Amino Acid Set 2 (Note that the Numbering of the Amino Acids Refers to the Amino Acids in the P10480 Mature Sequence)

Leu17, Lys22, Met23, Gly40, Asn80, Pro81, Lys82, Asn87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Met209, Leu210, Arg211, Asn215, Lys284, Met285, Gln289 and Val290.

Table of selected residues in Set 1 compared with Set 2:

| IVN model | | | P10480 |
|---|---|---|---|
| | A. hyd homologue | | Mature sequence Residue |
| IVN | PFAM | Structure | Number |
| Gly8 | Gly32 | | |
| Asp9 | Asp33 | | |
| Ser10 | Ser34 | | |
| Leu11 | Leu35 | | Leu17 |
| Ser12 | Ser36 | | Ser18 |
| | | | Lys22 |
| | | | Met23 |
| Tyr15 | Gly58 | | Gly40 |
| Gly44 | Asn98 | | Asn80 |
| Asp45 | Pro99 | | Pro81 |
| Thr46 | Lys100 | | Lys82 |
| | | | Asn87 |
| | | | Asn88 |
| Glu69 | Trp129 | | Trp111 |
| Leu70 | Val130 | | Val112 |
| Gly71 | Gly131 | | |
| Gly72 | Ala132 | | Ala114 |
| Asn73 | Asn133 | | |
| Asp74 | Asp134 | | |
| Gly75 | Tyr135 | | Tyr117 |
| Leu76 | Leu136 | | Leu118 |
| Gln106 | | Pro174 | Pro156 |
| Ile107 | | Gly177 | Gly159 |
| Arg108 | | Gln178 | Gln160 |
| Leu109 | | Asn179 | Asn161 |
| Pro110 | | 180 to 190 | Pro162 |

| IVN model | | | P10480 |
|---|---|---|---|
| | A. hyd homologue | | Mature sequence Residue |
| IVN | PFAM | Structure | Number |
| Tyr113 | | | Ser163 |
| | | | Ala164 |
| | | | Arg165 |
| | | | Ser166 |
| | | | Gln167 |
| | | | Lys168 |
| | | | Val169 |
| | | | Val170 |
| | | | Glu171 |
| | | | Ala172 |
| Phe121 | His198 | Tyr197 | Tyr179 |
| | | His198 | His180 |
| | | Asn199 | Asn181 |
| Phe139 | Met227 | | Met209 |
| Phe140 | Leu228 | | Leu210 |
| Met141 | Arg229 | | Arg211 |
| Tyr145 | Asn233 | | Asn215 |
| | | | Lys284 |
| Met151 | Met303 | | Met285 |
| Asp154 | Asp306 | | |
| Gly155 | Gln307 | | Gln289 |
| Ile156 | Val308 | | Val290 |
| His157 | His309 | | |
| Pro158 | Pro310 | | |

Amino Acid Set 3:

Amino acid set 3 is identical to set 2 but refers to the *Aeromonas salmonicida* (SEQ ID No. 28) coding sequence, i.e. the amino acid residue numbers are 18 higher in set 3 as this reflects the difference between the amino acid numbering in the mature protein (SEQ ID No. 2) compared with the protein including a signal sequence (SEQ ID No. 28).

The mature proteins of *Aeromonas salmonicida* GDSX (SEQ ID No. 28) and *Aeromonas hydrophila* GDSX (SEQ ID No. 26) differ in five amino acids. These are Thr3Ser, Gln182Lys, Glu309Ala, Ser310Asn, Gly318-, where the *salmonicida* residue is listed first and the hydrophila residue is listed last (FIG. 59). The *hydrophila* protein is only 317 amino acids long and lacks a residue in position 318. The *Aeromonas salmonicidae* GDSX has considerably high activity on polar lipids such as galactolipid substrates than the *Aeromonas hydrophila* protein. Site scanning was performed on all five amino acid positions.

Amino Acid Set 4:

Amino acid set 4 is S3, Q182, E309, S310, and –318.

Amino Acid Set 5:

F13S, D15N, S18G, S18V, Y30F, D116N, D116E, D157N, Y226F, D228N Y230F.

Amino Acid Set 6:

Amino acid set 6 is Scr3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, –318.

The numbering of the amino acids in set 6 refers to the amino acids residues in P10480 (SEQ ID No. 2)—corresponding amino acids in other sequence backbones can be determined by homology alignment and/or structural alignment to P10480 and/or 1IVN.

Amino Acid Set 7:

Amino acid set 7 is Ser3, Leu17, Lys22, Met23, Gly40, Asn80, Pro81, Lys82, Asn 87, Asn88, Trp111, Val112, Ala114, Tyr117, Leu118, Pro156, Gly159, Gln160, Asn161, Pro162, Ser163, Ala164, Arg165, Ser166, Gln167, Lys168, Val169, Val170, Glu171, Ala172, Tyr179, His180, Asn181, Gln182, Met209, Leu210, Arg211, Asn215, Lys284, Met285, Gln289, Val290, Glu309, Ser310, –318, Y30X (where X is selected from A, C, D, E, G, H, I, K, L, M, N, P, Q, R, S, T, V, or W), Y226X (where X is selected from A, C, D, E, G, H, I, K, L, M, N, P, Q, R, S, T, V, or W), Y230X (where X is selected from A, C, D, E, G, H, I, K, L, M, N, P, Q, R, S, T, V, or W), S18X (where X is selected from A, C, D, E, F, H, I, K, L, M, N, P, Q, R, T, W or Y), D157X (where X is selected from A, C, E, F, G, H, I, K, L, M, P, Q, R, S, T, V, W or Y).

The numbering of the amino acids in set 7 refers to the amino acids residues in P10480 (SEQ ID No. 2)—corresponding amino acids in other sequence backbones can be determined by homology alignment and/or structural alignment to P10480 and/or 1IVN).

Isolated

In one aspect, preferably the polypeptide or protein for use in the present invention is in an isolated form. The term "isolated" means that the sequence is at least substantially free from at least one other component with which the sequence is naturally associated in nature and as found in nature.

Purified

In one aspect, preferably the polypeptide or protein for use in the present invention is in a purified form. The term "purified" means that the sequence is in a relatively pure state—e.g. at least about 51% pure, or at least about 75%, or at least about 80%, or at least about 90% pure, or at least about 95% pure or at least about 98% pure.

Cloning a Nucleotide Sequence Encoding a Polypeptide According to the Present Invention A nucleotide sequence encoding either a polypeptide which has the specific properties as defined herein or a polypeptide which is suitable for modification may be isolated from any cell or organism producing said polypeptide. Various methods are well known within the art for the isolation of nucleotide sequences.

For example, a genomic DNA and/or cDNA library may be constructed using chromosomal DNA or messenger RNA from the organism producing the polypeptide. If the amino acid sequence of the polypeptide is known, labelled oligonucleotide probes may be synthesised and used to identify polypeptide-encoding clones from the genomic library prepared from the organism. Alternatively, a labelled oligonucleotide probe containing sequences homologous to another known polypeptide gene could be used to identify polypeptide-encoding clones. In the latter case, hybridisation and washing conditions of lower stringency are used.

Alternatively, polypeptide-encoding clones could be identified by inserting fragments of genomic DNA into an expression vector, such as a plasmid, transforming enzyme-negative bacteria with the resulting genomic DNA library, and then plating the transformed bacteria onto agar containing an enzyme inhibited by the polypeptide, thereby allowing clones expressing the polypeptide to be identified.

In a yet further alternative, the nucleotide sequence encoding the polypeptide may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding polypeptides having the specific properties as defined herein. The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence.

In a preferred embodiment, the nucleotide sequence per se encoding a polypeptide having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the polypeptide of the present invention can be expressed by a nucleotide sequence in its native organism but wherein the nucleotide sequence is not under the control of the promoter with which it is naturally associated within that organism.

Preferably the polypeptide is not a native polypeptide. In this regard, the term "native polypeptide" means an entire polypeptide that is in its native environment and when it has been expressed by its native nucleotide sequence.

Typically, the nucleotide sequence encoding polypeptides having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Molecular Evolution

Once an enzyme-encoding nucleotide sequence has been isolated, or a putative enzyme-encoding nucleotide sequence has been identified, it may be desirable to modify the selected nucleotide sequence, for example it may be desirable to mutate the sequence in order to prepare an enzyme in accordance with the present invention.

Mutations may be introduced using synthetic oligonucleotides. These oligonucleotides contain nucleotide sequences flanking the desired mutation sites.

A suitable method is disclosed in Morinaga et al (Biotechnology (1984)2, p646-649). Another method of introducing mutations into enzyme-encoding nucleotide sequences is described in Nelson and Long (Analytical Biochemistry (1989), 180, p 147-151).

Instead of site directed mutagenesis, such as described above, one can introduce mutations randomly for instance using a commercial kit such as the GeneMorph PCR mutagenesis kit from Stratagene, or the Diversify PCR random mutagenesis kit from Clontech. EP 0 583 265 refers to methods of optimising PCR based mutagenesis, which can also be combined with the use of mutagenic DNA analogues such as those described in EP 0 866 796. Error prone PCR technologies are suitable for the production of variants of lipid acyl transferases with preferred characteristics. WO0206457 refers to molecular evolution of lipases.

A third method to obtain novel sequences is to fragment non-identical nucleotide sequences, either by using any number of restriction enzymes or an enzyme such as Dnase I, and reassembling full nucleotide sequences coding for functional proteins. Alternatively one can use one or multiple non-identical nucleotide sequences and introduce mutations during the reassembly of the full nucleotide sequence. DNA shuffling and family shuffling technologies are suitable for the production of variants of lipid acyl transferases with preferred characteristics. Suitable methods for performing 'shuffling' can be found in EP0 752 008, EP1 138 763, EP1 103 606. Shuffling can also be combined with other forms of DNA mutagenesis as described in U.S. Pat. No. 6,180,406 and WO 01/34835.

Thus, it is possible to produce numerous site directed or random mutations into a nucleotide sequence, either in vivo or in vitro, and to subsequently screen for improved functionality of the encoded polypeptide by various means. Using in silico and exo mediated recombination methods (see WO 00/58517, U.S. Pat. Nos. 6,344,328, 6,361,974), for example, molecular evolution can be performed where the variant produced retains very low homology to known enzymes or proteins. Such variants thereby obtained may have significant structural analogy to known transferase enzymes, but have very low amino acid sequence homology.

As a non-limiting example, in addition, mutations or natural variants of a polynucleotide sequence can be recombined with either the wild type or other mutations or natural variants to produce new variants. Such new variants can also be screened for improved functionality of the encoded polypeptide.

The application of the above-mentioned and similar molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimisation or alteration of enzyme activity, such examples include, but are not limited to one or more of the following: optimised expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, and/or substrate.

As will be apparent to a person skilled in the art, using molecular evolution tools an enzyme may be altered to improve the functionality of the enzyme.

Suitably, the lipid acyltransferase used in the invention may be a variant, i.e. may contain at least one amino acid substitution, deletion or addition, when compared to a parental enzyme. Variant enzymes retain at least 1%, 2%, 3%, 5%, 10%, 15%, 20%, 30%, 40%, 50%, 60%, 70%, 80%, 90%, 95%, 97%, 99% homology with the parent enzyme. Suitable parent enzymes may include any enzyme with esterase or lipase activity. Preferably, the parent enzyme aligns to the pfam00657 consensus sequence.

In a preferable embodiment a variant lipid acyltransferase enzyme retains or incorporates at least one or more of the pfam00657 consensus sequence amino acid residues found in the GDSx, GANDY and HPT blocks.

Enzymes, such as lipases with no or low lipid acyltransferase activity in an aqueous environment may be mutated using molecular evolution tools to introduce or enhance the transferase activity, thereby producing a lipid acyltransferase enzyme with significant transferase activity suitable for use in the compositions and methods of the present invention.

Suitably, the lipid acyltransferase for use in the invention may be a variant with enhanced enzyme activity phospholipids when compared to the parent enzyme. Preferably, such variants also have low or no activity on lyso polar lipids. The enhanced activity on phospholipids may be the result of hydrolysis and/or transferase activity or a combination of both.

Variant lipid acyltransferases for use in the invention may have decreased activity on triglycerides, and/or monoglycerides and/or diglycerides compared with the parent enzyme.

Suitably the variant enzyme may have no activity on triglycerides and/or monoglycerides and/or diglycerides.

Alternatively, the variant enzyme for use in the invention may have increased activity on triglycerides, and/or may also have increased activity on one or more of the following, polar lipids, phospholipids, lecithin, phosphatidylcholine.

Variants of lipid acyltransferases are known, and one or more of such variants may be suitable for use in the methods and uses according to the present invention and/or in the enzyme compositions according to the present invention. By way of example only, variants of lipid acyltransferases are described in the following references may be used in accordance with the present invention: Hilton & Buckley J. Biol. Chem. 1991 Jan. 15: 266 (2): 997-1000; Robertson et al J. Biol. Chem. 1994 Jan. 21; 269(3):2146-50; Brumlik et al J. Bacteriol 1996 April; 178 (7): 2060-4; Peelman et al Protein Sci. 1998 March; 7(3):587-99.

Amino Acid Sequences

The present invention also encompasses amino acid sequences of polypeptides having the specific properties as defined herein.

As used herein, the term "amino acid sequence" is synonymous with the term "polypeptide" and/or the term "protein". In some instances, the term "amino acid sequence" is synonymous with the term "peptide".

The amino acid sequence may be prepared/isolated from a suitable source, or it may be made synthetically or it may be prepared by use of recombinant DNA techniques.

Suitably, the amino acid sequences may be obtained from the isolated polypeptides taught herein by standard techniques.

One suitable method for determining amino acid sequences from isolated polypeptides is as follows:

Purified polypeptide may be freeze-dried and 100 µg of the freeze-dried material may be dissolved in 50 µl of a mixture of 8 M urea and 0.4 M ammonium hydrogen carbonate, pH 8.4. The dissolved protein may be denatured and reduced for 15 minutes at 50° C. following overlay with nitrogen and addition of 5 µl of 45 mM dithiothreitol. After cooling to room temperature, 5 µl of 100 mM iodoacetamide may be added for the cysteine residues to be derivatized for 15 minutes at room temperature in the dark under nitrogen.

135 µl of water and 5 µg of endoproteinase Lys-C in 5 µl of water may be added to the above reaction mixture and the digestion may be carried out at 37° C. under nitrogen for 24 hours.

The resulting peptides may be separated by reverse phase HPLC on a VYDAC C18 column (0.46×15 cm; 10 µm; The Separation Group, California, USA) using solvent A: 0.1% TFA in water and solvent B: 0.1% TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA), Sequence Identity or Sequence Homology The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the enzyme.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p387). Examples of other software that can perform sequence comparisons include, but are not limited to, the BLAST package (see Ausubel et al 1999 Short Protocols in Molecular Biology, 4$^{th}$ Ed—Chapter 18), FASTA (Altschul et al 1990 J. Mol. Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

In a preferable aspect of the present invention the following software and settings for calculating percentage homology/identity are used. For amino acid sequences percentage of identities (homology) or "positives" are calculated by the AlignX Vector NTI (Vector NTI Advance 9.1 from Invitrogen Corporation, Carlsbad, Calif., USA.), for each possible pair of amino acid sequences Settings are default parameters (Gap opening penalty −10, Gap extension penalty 0.1).

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Nucleotide sequences for use in the present invention or encoding a polypeptide having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction polypeptide recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The present invention also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the present invention encompasses sequences that are complementary to sequences that are capable of hybridising under high stringency conditions or intermediate stringency conditions to nucleotide sequences encoding polypeptides having the specific properties as defined herein.

More preferably, the present invention encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding polypeptides having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Expression of Polypeptides

A nucleotide sequence for use in the present invention or for encoding a polypeptide having the specific properties as defined herein can be incorporated into a recombinant replicable vector. The vector may be used to replicate and express the nucleotide sequence, in polypeptide form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The polypeptide produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

The nucleotide sequence of the present invention or coding for a polypeptide having the specific properties as defined herein may be present in a vector, in which the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide having the specific properties as defined herein.

The choice of vector, e.g. plasmid, cosmid, virus or phage vector, will often depend on the host cell into which it is to be introduced.

The vectors may contain one or more selectable marker genes—such as a gene which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect or transform a host cell.

Thus, in a further embodiment, the invention provides a method of making nucleotide sequences of the present invention or nucleotide sequences encoding polypeptides having the specific properties as defined herein by introducing a nucleotide sequence into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence for use in the present invention or a nucleotide sequence encoding a polypeptide having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under conditions compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions.

Preferably, the nucleotide sequence of the present invention may be operably linked to at least a promoter.

Examples of suitable promoters for directing the transcription of the nucleotide sequence in a bacterial, fungal or yeast host are well known in the art.

Constructs

The term "construct"—which is synonymous with terms such as "conjugate", "cassette" and "hybrid"—includes a nucleotide sequence encoding a polypeptide having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct.

For some applications, preferably the construct comprises at least a nucleotide sequence of the present invention or a nucleotide sequence encoding a polypeptide having the specific properties as defined herein operably linked to a promoter.

Host Cells

The term "host cell"—in relation to the present invention includes any cell that comprises either a nucleotide sequence encoding a polypeptide having the specific properties as defined herein or an expression vector as described above and which is used in the recombinant production of a polypeptide having the specific properties as defined herein.

Thus, a further embodiment of the present invention provides host cells transformed or transfected with a nucleotide sequence of the present invention or a nucleotide sequence that expresses a polypeptide having the specific properties as defined herein. The cells will be chosen to be compatible with the said vector and may for example be prokaryotic (for example bacterial), fungal, yeast or plant cells. Preferably, the host cells are not human cells.

Examples of suitable bacterial host organisms are gram negative bacterium or gram positive bacteria.

Depending on the nature of the nucleotide sequence encoding a polypeptide having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells, such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain.

Organism

The term "organism" in relation to the present invention includes any organism that could comprise a nucleotide sequence according to the present invention or a nucleotide sequence encoding for a polypeptide having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for a polypeptide having the specific properties as defined herein and/or the products obtained therefrom, and/or wherein a promoter can allow expression of the nucleotide sequence coding for a polypeptide having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for a polypeptide having the specific properties as defined herein, constructs as defined herein, vectors as defined herein, plasmids as defined herein, cells as defined herein, or the products thereof. For example the transgenic organism can also comprise a nucleotide sequence coding for a polypeptide having the specific properties as defined herein under the control of a heterologous promoter.

Transformation of Host Cells/Organism

As indicated earlier, the host organism can be a prokaryotic or a eukaryotic organism. Examples of suitable prokaryotic hosts include *E. coli* and *Bacillus subtilis.*

In one embodiment the host cell is a bacteria, preferably a gram-positive bacteria, preferably a host cell selected from *Actinobacteria*, such as *Biofidobacteria* and *Aeromonas*, particularly preferably *Aeromonas salmonicida*. Still more preferred are Actinomicetales such as *Corynebacteria*, in particular *Corynebacterium glutamicum* and *Nocardia*. Particularly preferred are *Streptomycetaceae*, such as *Streptomyces*, especially *S. lividans.*

A microbial host can be used for expression of the galactolipase gene, e.g. Eubacteria, Archea or Fungi, including yeast. Preferred are Eubacteria, for example, *Firmicutes* (low GC-Gram positive bacteria), such as *Bacillus subtilis* and other *bacillus* species, lactic acid bacteria such as species of genera *Lactobacillus* and *Lactococcus.*

Also preferred are Gram-negative Proteobacteria, in particular Gammaproteobacteria, such as host species belonging to the genera *Pseudomonas, Xanthomonas, Citrobacter* and *Escherichia*, especially *Escherichia coli.*

Preferably the host species is a Gram positive expression host such as *Aeromonas salmonicida, Streptomyces lividans* or *Corynebacterium glutamicum* as detailed in GB application number 0513859.9

In another embodiment the host cell is the same genus as the native host species, i.e. the recombinant gene is re-introduced and expressed in a species from the same genus as the species from which the recombinant gene was isolated.

In another embodiment the host cell is the native host species, i.e. the recombinant gene is re-introduced and expressed in the same species from which the recombinant gene was isolated.

Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the nucleotide sequence may need to be suitably modified before transformation—such as by removal of introns.

In another embodiment the transgenic organism can be a yeast.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol* [1991] 42:205-225) and Christou (Agro-Food-Industry Hi-Tech March/April 1994 17-27). Further teachings on plant transformation may be found in EP-A-0449375.

General teachings on the transformation of fungi, yeasts and plants are presented in following sections.

Transformed Fungus

A host organism may be a fungus—such as a filamentous fungus. Examples of suitable such hosts include any member belonging to the genera *Thermomyces, Acremonium, Aspergillus, Penicillium, Mucor, Neurospora, Trichoderma* and the like.

Teachings on transforming filamentous fungi are reviewed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings on transforming filamentous fungi are reviewed in U.S. Pat. No. 5,674,707.

In one aspect, the host organism can be of the genus *Aspergillus*, such as *Aspergillus niger*.

A transgenic *Aspergillus* according to the present invention can also be prepared by following, for example, the teachings of Turner G. 1994 (Vectors for genetic manipulation. In: Martinelli S. D., Kinghorn J. R. (Editors) *Aspergillus: 50 years on*. Progress in industrial microbiology vol 29. Elsevier Amsterdam 1994. pp. 641-666).

Gene expression in filamentous fungi has been reviewed in Punt et al. (2002) Trends Biotechnol 2002 May; 20(5):200-6, Archer & Peberdy Crit. Rev Biotechnol (1997) 17(4):273-306.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisi* or *Pichia pastoris* (see FEMS Microbiol Rev (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *Proceedings of the National Academy of Sciences of the USA* 75, 1929); Beggs, J D (1978, Nature, London, 275, 104); and Ito, H et al (1983, J Bacteriology 153, 163-168).

The transformed yeast cells may be selected using various selective markers—such as auxotrophic markers dominant antibiotic resistance markers.

A suitable yeast host organism can be selected from the biotechnologically relevant yeasts species such as, but not limited to, yeast species selected from *Pichia* spp., *Hansenula* spp., *Kluyveromyces*, *Yarrowinia* spp., *Saccharomyces* spp., including *S. cerevisiae*, or *Schizosaccharomyce* spp. including *Schizosaccharomyce pombe*.

A strain of the methylotrophic yeast species *Pichia pastoris* may be used as the host organism.

In one embodiment, the host organism may be a *Hansenula* species, such as *H. polymorpha* (as described in WO01/39544).

Transformed Plants/Plant Cells

A host organism suitable for the present invention may be a plant. A review of the general techniques may be found in articles by Potrykus (*Annu Rev Plant Physiol Plant Mod Biol* [1991] 42:205-225) and Christou (Agro-Food-Industry Hi-Tech March/April 1994 17-27), or in WO01/16308.

Secretion

Often, it is desirable for the polypeptide to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces*, *Kluyveromyces* and *Hansenula*) or the α-amylase gene (Bacillus).

Detection

A variety of protocols for detecting and measuring the expression of the amino acid sequence are known in the art. Examples include enzyme-linked immunosorbent assay (ELISA), radioimmunoassay (RIA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

A polypeptide having the specific properties as defined herein may be produced as a fusion protein, for example to aid in extraction and purification thereof. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the activity of the protein sequence.

Gene fusion expression systems in *E. coli* have been reviewed in Curr. Opin. Biotechnol. (1995) 6(5):50'-6.

In another embodiment of the invention, the amino acid sequence of a polypeptide having the specific properties as defined herein may be ligated to a heterologous sequence to encode a fusion protein. For example, for screening of peptide libraries for agents capable of affecting the substance activity, it may be useful to encode a chimeric substance expressing a heterologous epitope that is recognised by a commercially available antibody.

The invention will now be described, by way of example only, with reference to the following figures and examples.

Figure 3:
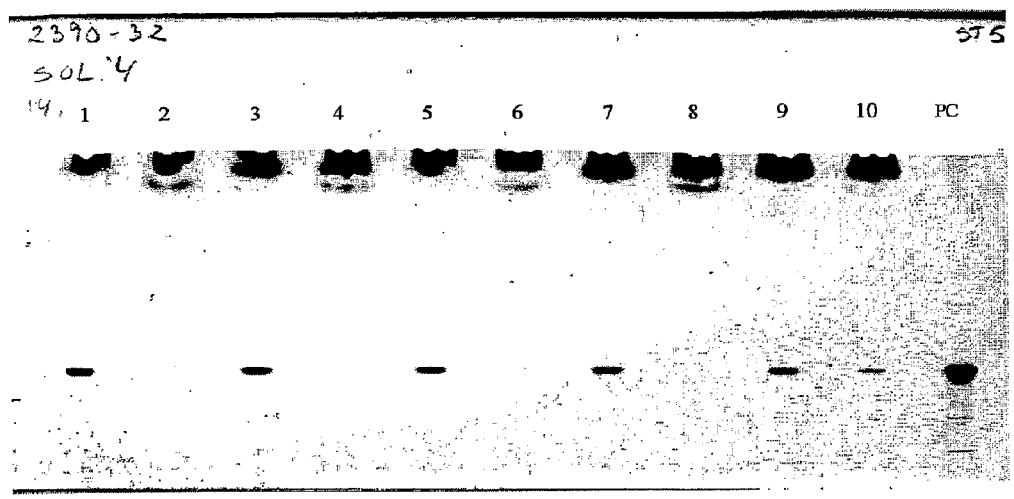
Figure 4:
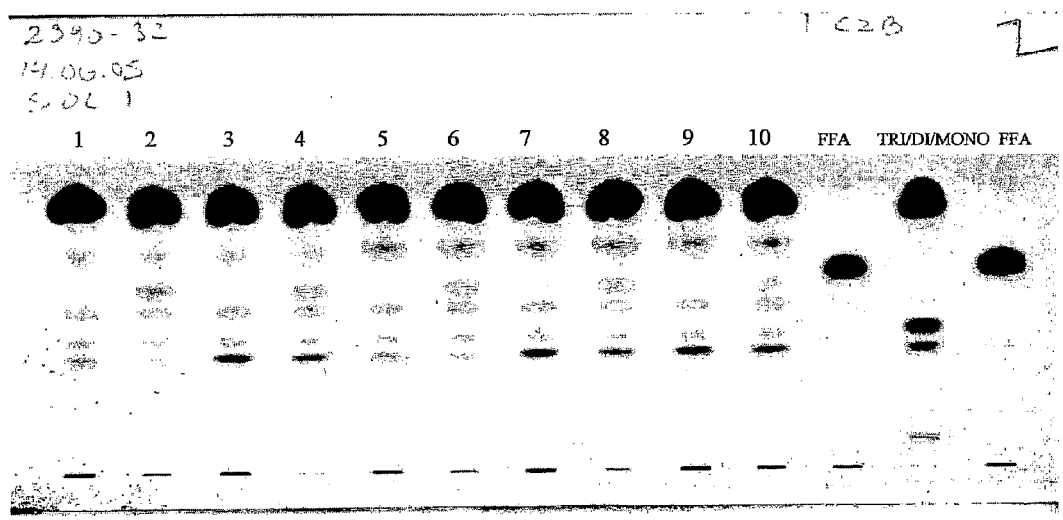
Figure 5:
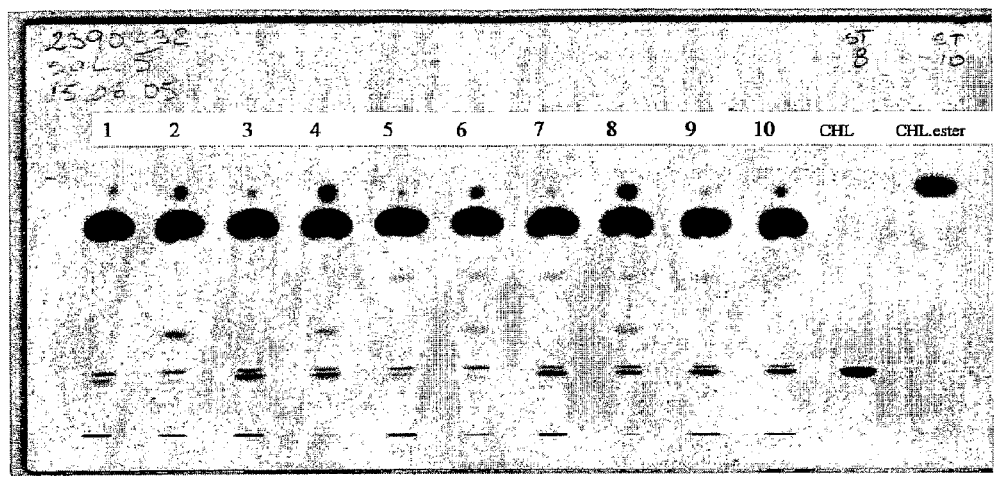
Figure 6:
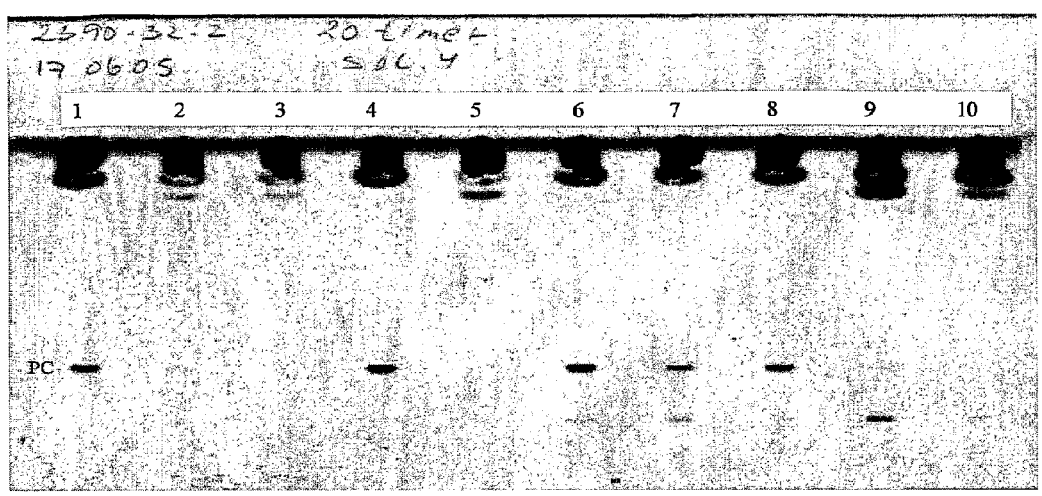
Figure 7:
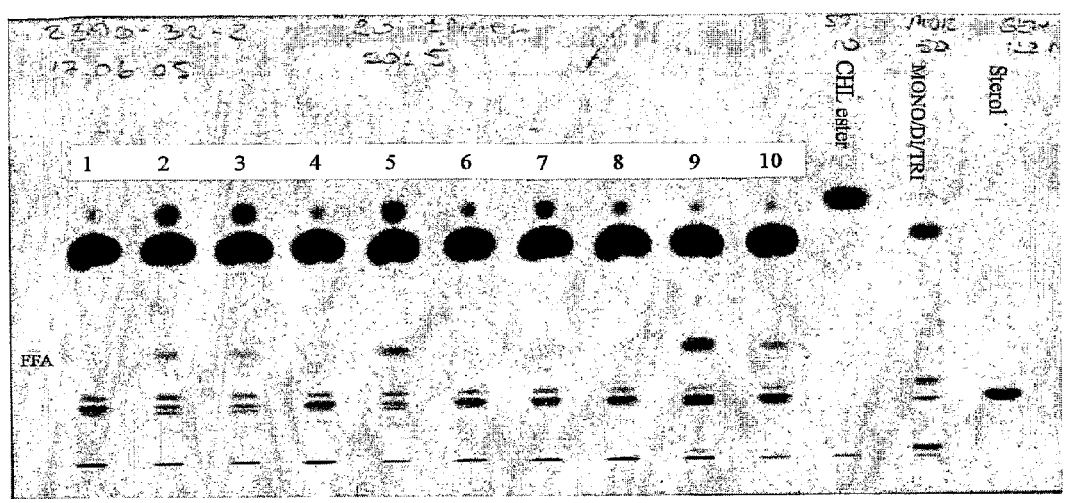
Figure 8:
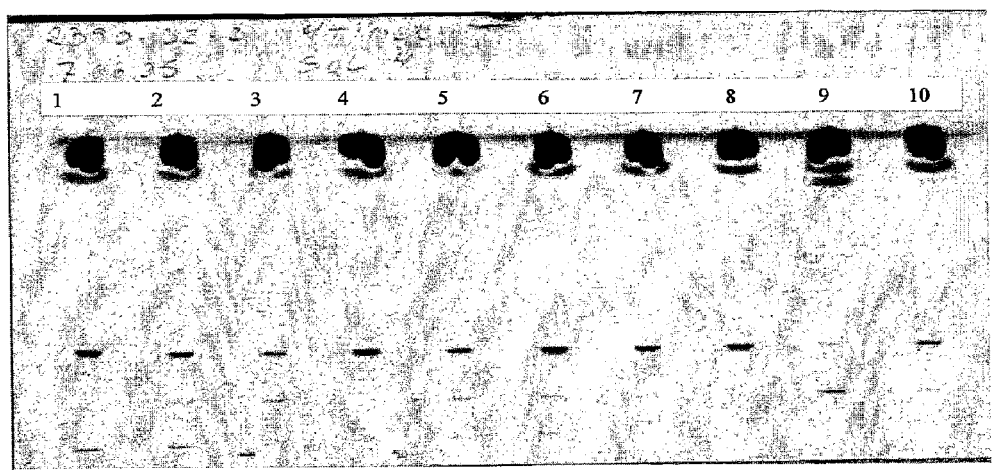
Figure 9:
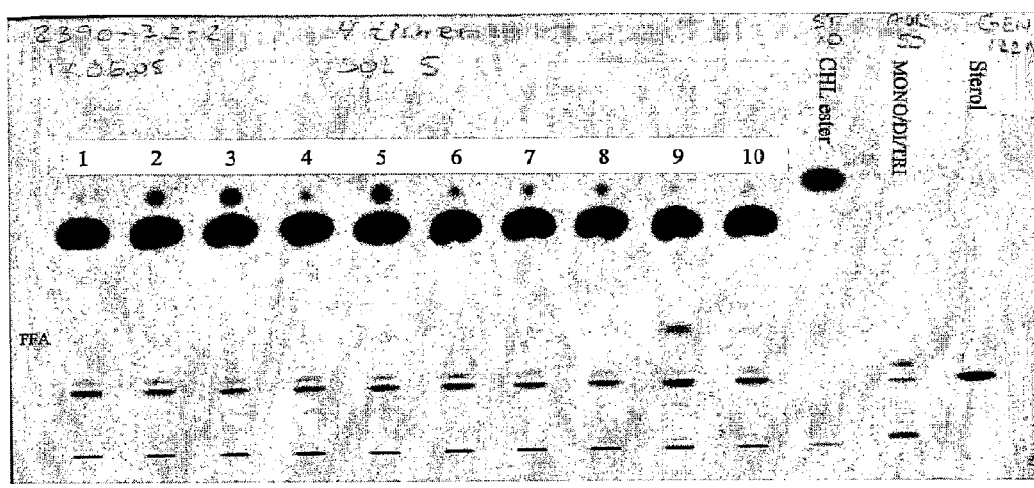
Figure 26:
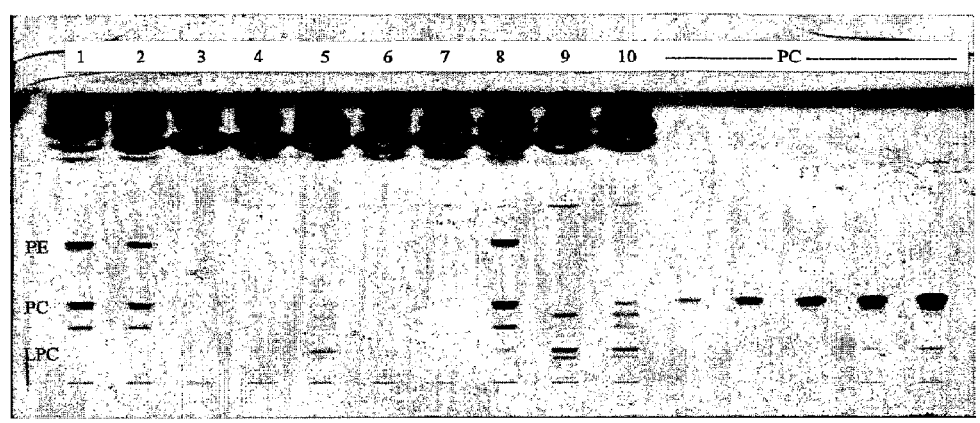

Lane 1. Lipid acyltransferase sample after desalting, 40 μl was applied to the gel Lane 2. Lipid acyltransferase sample after desalting, 10 μl was applied to the gel Lane 3. Purified Lipid acyltransferase lipase after IEC (pool 27-39), 40 μl was applied to the gel Lane 4. Purified Lipid acyltransferase lipase after IEC (pool 27-39, 10 µl was applied to the gel;

FIG. 3 shows a TLC (Solvent 4) of reaction products from the lipid acyltransferase treatment of soya bean oil samples according to Table 2. As a reference phosphatidylcholine (PC) was also analysed;

FIG. 4 shows a TLC (Solvent 1) of reaction products from the lipid acyltransferase treatment of soya bean oil samples according to Table 2. As reference free fatty acid (FFA) and Mono-di-triglyceride (TRI/DI/MONO) were also analysed;

FIG. 5 shows a TLC (Solvent 5) of reaction products from the lipid acyltransferase treatment of soya bean oil samples according to Table 2. As reference Cholesterol (CHL) and Cholesterolester (CHL-ester) were also analysed;

FIG. 6 shows a TLC (Solvent 4) of reaction products from the lipid acyltransferase or Lecitase Ultra™ treatment of soya bean oil samples according to Table 3 for 20 hours;

FIG. 7 shows a TLC (Solvent 5) of reaction products from the lipid acyltransferase or Lecitase Ultra™ treatment of soya bean oil samples according to Table 3 for 20 hours. Cholesterol ester (CHL ester); Mono-di-Triglyceride(MONO/DI/TRI) and plant sterol were also analysed as references. Identification of free fatty acid (FFA) is also indicated;

FIG. 8 shows a TLC (Solvent 4) of reaction products from the lipid acyltransferase or Lecitase Ultra™ treatment of soya bean oil samples according to Table 3 for 4 hours;

FIG. 9 shows a TLC (Solvent 5) of reaction products from the lipid acyltransferase or Lecitase Ultra™ treatment of soya bean oil samples according to Table 3 for 4 hours. Cholesterol ester (CHL ester); Mono-di-Triglyceride (MONO/DI/TRI) and plant sterol were also analysed as references. Identification of free fatty acid (FFA) is also indicated;

FIG. 10 shows the amino acid sequence of a mutant *Aeromonas salmonicida* mature lipid acyltransferase (GCAT) with a mutation of Asn80Asp (notably, amino acid 80 is in the mature sequence);

FIG. 11 shows an amino acid sequence (SEQ ID No. 1) a lipid acyl transferase from *Aeromonas hydrophila* (ATCC #7965);

FIG. 12 shows a pfam00657 consensus sequence from database version 6 (SEQ ID No. 2);

FIG. 13 shows an amino acid sequence (SEQ ID No. 3) obtained from the organism *Aeromonas hydrophila* (P10480; GI:121051);

FIG. 14 shows an amino acid sequence (SEQ ID No. 4) obtained from the organism *Aeromonas salmonicida* (AAG098404; GI:9964017);

FIG. 15 shows an amino acid sequence (SEQ ID No. 5) obtained from the organism *Streptomyces coelicolor* A3(2) (Genbank accession number NP_631558);

FIG. 16 shows an amino acid sequence (SEQ ID No. 6) obtained from the organism *Streptomyces coelicolor* A3(2) (Genbank accession number: CAC42140);

FIG. 17 shows an amino acid sequence (SEQ ID No. 7) obtained from the organism *Saccharomyces cerevisiae* (Genbank accession number P41734);

FIG. 18 shows an amino acid sequence (SEQ ID No. 8) obtained from the organism Ralstonia (Genbank accession number: AL646052);

FIG. 19 shows SEQ ID No. 9. Scoe1 NCBI protein accession code CAB39707.1 GI:4539178 conserved hypothetical protein [*Streptomyces coelicolor* A3(2)];

FIG. 20 shows an amino acid shown as SEQ ID No. 10. Scoe2 NCBI protein accession code CAC01477.1 GI:9716139 conserved hypothetical protein [*Streptomyces coelicolor* A3(2)];

FIG. 21 shows an amino acid sequence (SEQ ID No. 11) Scoe3 NCBI protein accession code CAB88833.1 GI:7635996 putative secreted protein. [*Streptomyces coelicolor* A3(2)];

FIG. 22 shows an amino acid sequence (SEQ ID No. 12) Scoe4 NCBI protein accession code CAB89450.1 GI:7672261 putative secreted protein. [*Streptomyces coelicolor* A3(2)];

FIG. 23 shows an amino acid sequence (SEQ ID No. 13) Scoe5 NCBI protein accession code CAB62724.1 GI:6562793 putative lipoprotein [*Streptomyces coelicolor* A3(2)];

FIG. 24 shows an amino acid sequence (SEQ ID No. 14) Srim1 NCBI protein accession code AAK84028.1 GI:15082088 GDSL-lipase [*Streptomyces rimosus*];

FIG. 25 shows an amino acid sequence (SEQ ID No. 15) of a lipid acyltransferase from *Aeromonas salmonicida* subsp. *Salmonicida* (ATCC#14174);

FIG. 26 shows a TLC (solvent 4) of sample 1 to 10 of crude soya oil treated 20 hours with enzymes according to Table 4. PC is phosphatidylcholine added in 5 different concentrations (reference material).

Figure 27:
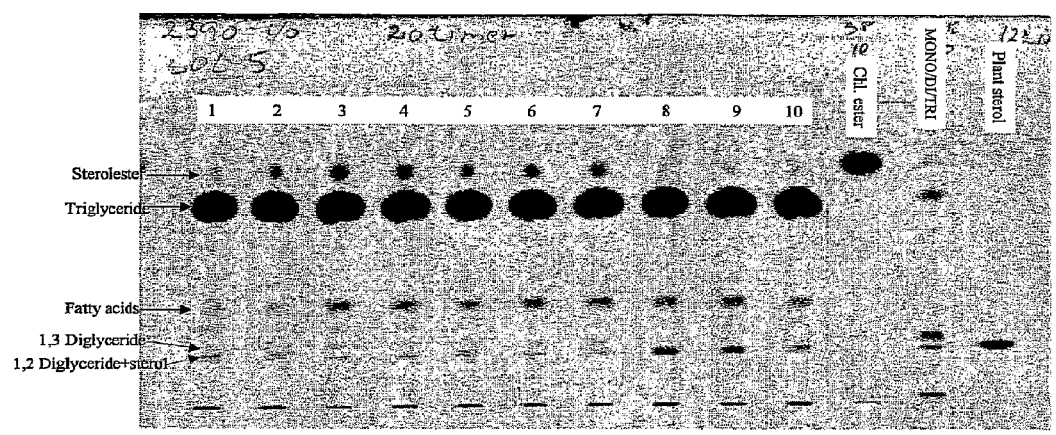

FIG. 27 shows a TLC (Solvent 5) of reaction products from lipid acyl transferase or Lecitase Ultra™ treatment of crude soya oil samples according to Table 4 (20 hours). Cholesterol ester (CHL-ester), Mono-di-Triglyceride (MONO/DI/TRI), and plant sterol were also analysed as references. Identification of free fatty acid is also indicated.

FIG. 28 shows SEQ ID No 17 which is the amino acid sequence of a lipid acyltransferase from *Candida parapsilosis*;

FIG. 29 shows SEQ ID No 18 which is the amino acid sequence of a lipid acyltransferase from *Candida parapsilosis*;

FIG. 30 shows alignment 1;

FIG. 31 shows SEQ ID No. 19. Scoe1 NCBI protein accession code CAB39707.1 GI:4539178 conserved hypothetical protein [*Streptomyces coelicolor* A3(2)];

FIG. 32 shows an amino acid sequence (SEQ ID No. 25) of the fusion construct used for mutagenesis of the *Aeromonas hydrophila* lipid acyltransferase gene. The underlined amino acids is a xylanase signal peptide;

FIG. 33 shows a polypeptide sequence of a lipid acyltransferase enzyme from *Streptomyces* (SEQ ID No. 26);

FIG. 34 shows a polypeptide sequence of a lipid acyltransferase enzyme from *Thermobifida* (SEQ ID No. 27);

FIG. 35 shows a polypeptide sequence of a lipid acyltransferase enzyme from *Thermobifida* (SEQ ID No. 28);

FIG. 36 shows a polypeptide of a lipid acyltransferase enzyme from *Corynebacterium efficiens* GDSx 300 amino acid (SEQ ID No. 29);

FIG. 37 shows a polypeptide of a lipid acyltransferase enzyme from *Novosphingobium aromaticivorans* GDSx 284 amino acid (SEQ ID No. 30);

FIG. 38 shows a polypeptide of a lipid acyltransferase enzyme from *Streptomyces coelicolor* GDSx 269 aa (SEQ ID No. 31)

Figure 41:
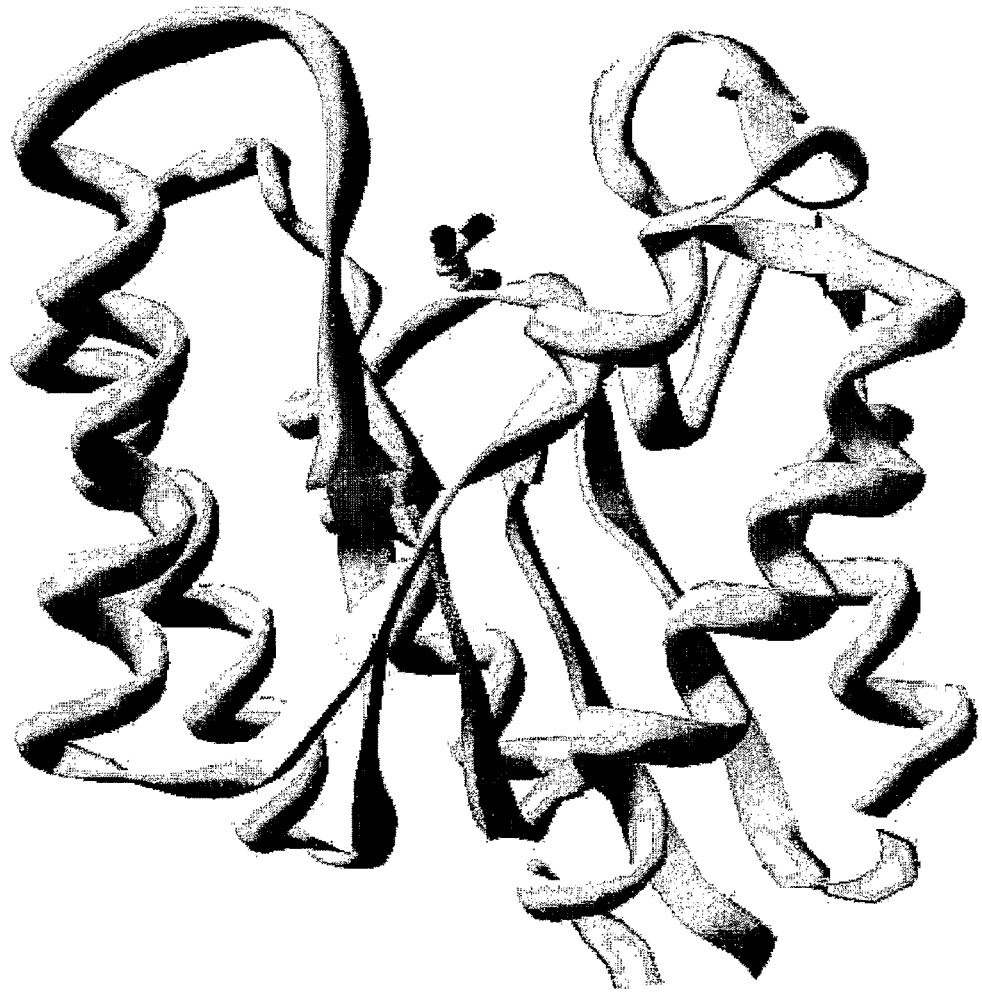
Figure 42:
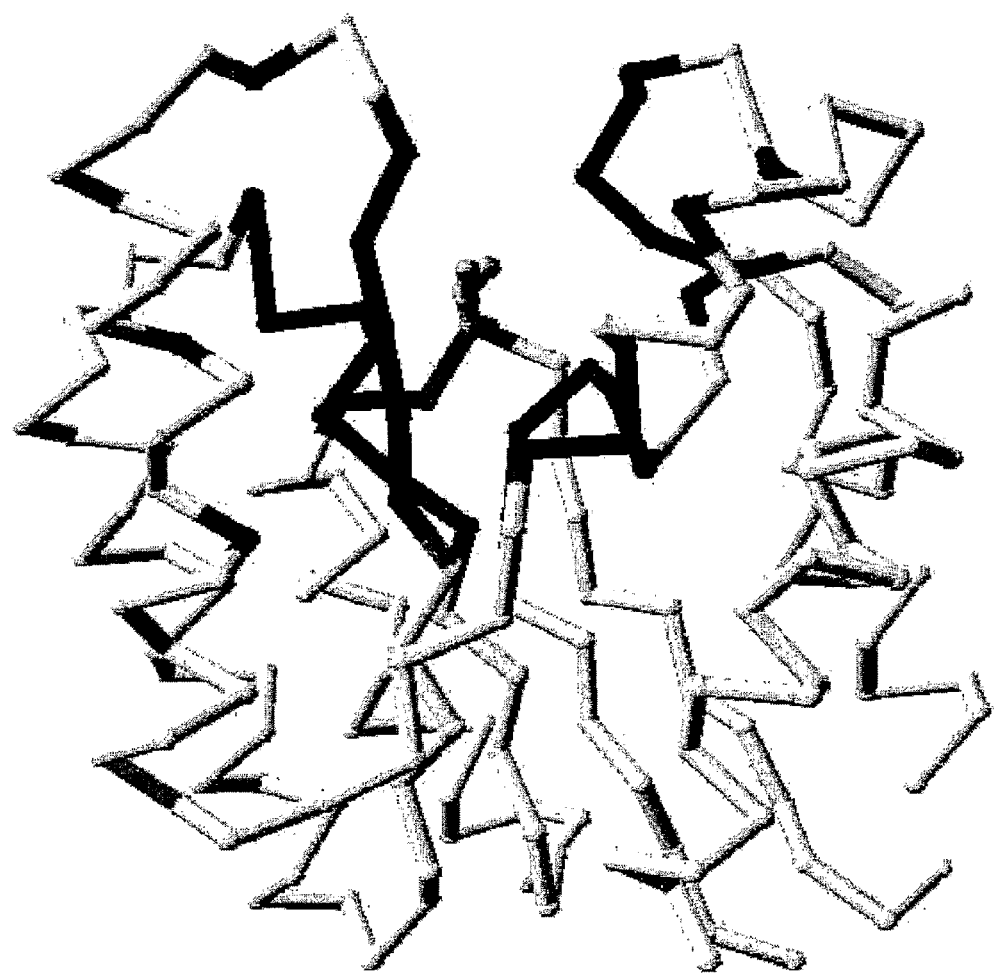

FIG. 39 shows a polypeptide of a lipid acyltransferase enzyme from *Streptomyces avermitilis*\GDSx 269 amino acid (SEQ ID No. 32);

FIG. 40 shows a polypeptide of a lipid acyltransferase enzyme from *Streptomyces* (SEQ ID No. 33);

FIG. 41 shows a ribbon representation of the 1IVN.PDB crystal structure which has glycerol in the active site. The Figure was made using the Deep View Swiss-PDB viewer;

FIG. 42 shows 1IVN.PDB Crystal Structure—Side View using Deep View Swiss-PDB viewer, with glycerol in active site—residues within 10Å of active site glycerol are coloured black;

FIG. 43 shows alignment 2;

FIG. 44 shows an amino acid sequence (SEQ ID No. 34) obtained from the organism *Aeromonas hydrophila* (P10480; GI:121051) (notably, this is the mature sequence).

FIG. 45 shows the amino acid sequence (SEQ ID No. 35) of a mutant *Aeromonas salmonicida* mature lipid acyltransferase (GCAT) (notably, this is the mature sequence)

FIG. 46 shows a nucleotide sequence (SEQ ID No. 36) from *Streptomyces thermosacchari*

FIG. 47 shows an amino acid sequence (SEQ ID No. 37) from *Streptomyces thermosacchari*

FIG. 48 shows an amino acid sequence (SEQ ID No. 38) from *Thermobifida fusca*/GDSx 548 amino acid FIG. 49 shows a nucleotide sequence (SEQ ID No. 39) from *Thermobifida fusca*

FIG. 50 shows an amino acid sequence (SEQ ID No. 40) from *Thermobifida fusca*/GDSx FIG. 51 shows an amino acid sequence (SEQ ID No. 41) from *Corynebacterium efficiens*/GDSx 300 amino acid FIG. 52 shows a nucleotide sequence (SEQ ID No. 42) from *Corynebacterium efficiens*

FIG. 53 shows an amino acid sequence (SEQ ID No. 43) from *S. coelicolor*/GDSx 268 amino acid FIG. 54 shows a nucleotide sequence (SEQ ID No. 44) from *S. coelicolor*

FIG. 55 shows an amino acid sequence (SEQ ID No. 45) from *S. avermitilis*

FIG. 56 shows a nucleotide sequence (SEQ ID No. 46) from *S. avermitilis*

Figure 59:
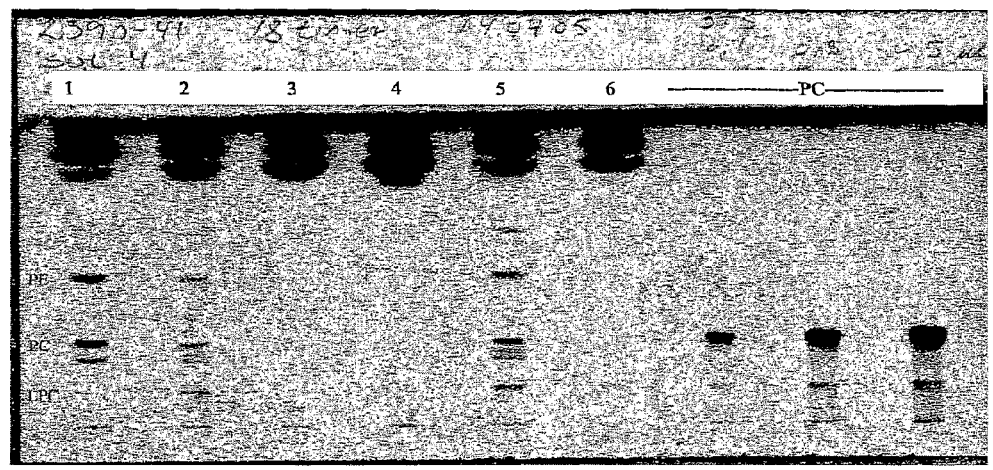

FIG. 57 shows an amino acid sequence (SEQ ID No. 47) from *Thermobifida fusca*/GDSx FIG. 58 shows a nucleotide sequence (SEQ ID No. 48) from *Thermobifida fusca*/GDSx FIG. 59 shows TLC (Solvent 4) of reaction products from enzyme treatment of crude soya oil samples according to table 6. As reference, phosphatidylcholine (PC) was also analysed. PE (phosphatydylethanolamine (PE) and lysophosphatidylcholine (LPC) are also indicated.

Figure 60:
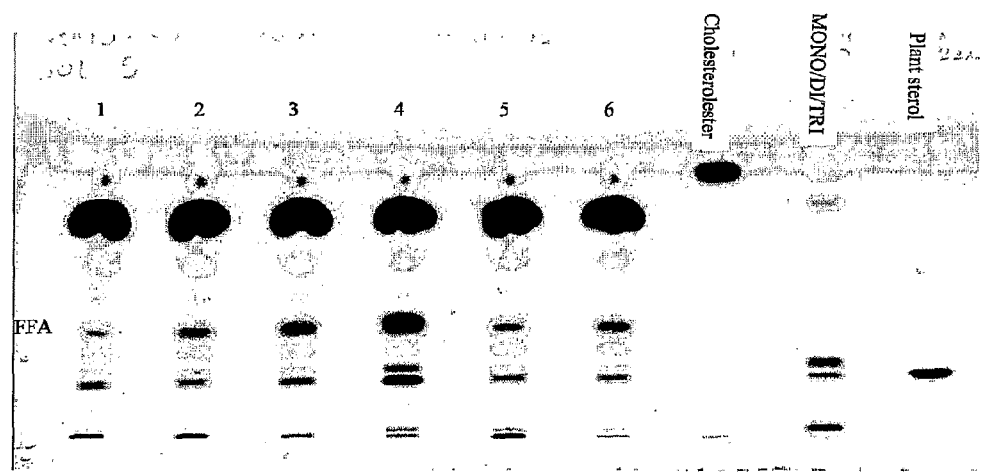

FIG. 60 shows TLC (Solvent 5) of reaction products from enzyme treatment of crude soya oil samples according to table 6. References Cholesterolester, mono-di-triglyceride and plant sterol. Free fatty acid (FFA) is also indicated FIG. 61 shows an alignment of the L131 and homologues from *S. avermitilis* and *T. fusca* illustrates that the conservation of the GDSx motif (GDSY in L131 and *S. avermitilis* and *T. fusca*), the GANDY box, which is either GGNDA or GGNDL, and the HPT block (considered to be the conserved catalytic histadine). These three conserved blocks are highlighted

EXAMPLES

The purpose of this study was to investigate the possible use of a lipid acyltransferase (sometimes referred to herein as a glycerophospholipid Cholesterol Acyl-Transferase (GCAT)) for degumming of vegetable oil like soya bean oil, sunflower oil and rape seed oil.

One purpose of this study was to investigate whether in particular a lipid acyltransferase mutant (N80D) is a more suitable enzyme for degumming. From earlier studies it is known that lipid acyltransferases (particularly GCATs) catalyse the acyl-transfer of fatty acid from phospholipid to sterols to form lysolecithin and sterol esters.

The present study was conducted in a model based on refined soya bean oil where phosphatidylcholine and plant sterols were added. This model was selected because it is easier to analyse reaction product in a model system instead of using crude soya oil.

Enzymatic degumming processes of plant oils including soya oil and rape seed oil is expanding in recent years because this process is a cheaper and better process to remove lecithins from oil. The enzyme used for oil degumming is a phospholipase A1 (Lecitase Ultra™ or pancreatic phospholipase A2—Novozymes A/S, Denmark).

One advantage of the enzyme of the present invention when used in degumming compared with prior art phospholipase A1 is that the enzyme according to the present invention facilitates the formation of sterol esters during the degumming process and contributes to the accumulation of sterol esters, which is not achieved with the currently used phospholipase A1 (Lecitase Ultra™).

Materials and Methods.

Enzymes

Lipid acyltransferase according to the present invention: *Aeromonas salmonicidae* enzyme with a mutation Asn80Asp (amino acid 80 of the mature enzyme) (SEQ ID No. 16 (see FIG. 10));

Lecitase Ultra (#3108) from Novozymes, Denmark

Soya bean oil: Soya olie IP (Item No. 005018/batch nr T-6, 8-4)

Lecithin: L-α Phosphatidylcholine 95% Plant (Avanti #441601)

Plant Sterol Generol 122 N from Henkel, Germany.

Tocopherol: Alpha-tocopherol (Item no. 050908/lot. nr 4010140554)

Phospholipase Activity

Substrate 0.6% L-α Phosphatidylcholine 95% Plant (Avanti #441601), 0.4% Triton-X 100 (Sigma X-100) and 5 mM $CaCl_2$ was dissolved in 0.05M HEPES buffer pH 7.

Assay Procedure:

400 μl substrate was added to an 1.5 ml Eppendorf tube and placed in an Eppendorf Thermomixer at 37° C. for 5 minutes. At time T=0 mM, 50 μl enzyme solution was added. Also a blank with water instead of enzyme was analyzed. The sample was mixed at 10*100 rpm in an Eppendorf Thermomixer at 37° C. for 10 minutes. At time T=10 min the Eppendorf tube was placed in another thermomixer at 99° C. for 10 minutes to stop the reaction.

Free fatty acid in the samples was analyzed by using the NEFA C kit from WAKO GmbH.

Enzyme activity PLU-NEFA pH 7 was calculated as micromole fatty acid produced per minute under assay conditions.

HPTLC

Applicator: Automatic TLC Sampler 4, CAMAG

HPTLC plate: 20×10 cm, Merck no. 1.05641. Activated 30 min. at 160° C. before use.

Application: 1 μl of a 8% solution of oil in buffer is applied to the HPTLC plate using Automatic TLC applicator.

Running buffer 1: P-ether:Methyl-tert-butyl-ether:Acetic acid 60:40:1

Running buffer 4: Chloroform:Methanol:Water 75:25:4

Running buffer 5: P-ether:Methyl-tert-butylether:Acetic acid 70:30:1

Application/Elution time: Running buffer 1: 12 min
  Running buffer 4: 20 min
  Running buffer 5: 10 mM Developing The plate is dried in an oven at 160° C. for 10 minutes, cooled, and dipped into 6% cupri acetate in 16% $H_3PO_4$. Dried additionally 10 minutes at 160° C. and evaluated directly.

Example 1

Enzyme Purification

Sample: The sample lipid acyltransferase (Asn80Asp) (SEQ ID No. 16) was filtered through 0.8/0.22 μm filter. 510 ml filtrate was collected.

Step 1. Desalting, Sephadex 25 G, 3.2 l Gel (10 cm id)

The Sephadex column was prepared as described by the manufacturer (Amersham biosciences). The column was equilibrated with 20 mM Na—P-buffer, pH 8.0. The sample (510 ml) was applied to the column at a flow rate of 25 ml/min. 815 ml desalted sample was collected and kept at +4° C.

Step 2. Anion Exchange Chromatography, Q-Sepharose FF 300 ml Gel (XK 50)

Q-Sepharose FF column was prepared as described by the manufacturer (Amersham biosciences). The column was equilibrated with 20 mM Na—P-buffer, pH 8.0. The desalted sample was applied to the column at a flow rate of 15 ml/min. The column was then washed with buffer A. The lipase was eluted with a linear gradient of 0-0.4 M NaCl in 20 mM Na—P-buffer (pH 8.0, buffer 13). Fractions of 15 ml were collected during the entire run. The lipase was eluted at approx. 0.2 M NaCl, and no lipase activity was detected in running through fractions.

Enzyme Assay Based on PNP-Caprylate

The assay was performed using PNP-Capylate as substrate as follows:

10 mg of substrate solved in 1 ml ethanol and was mixed with 9 ml of 50 mM Tris-HCL buffer (pH 7.3) containing 0.4% TX100.

240 μl of substrate was pre-incubated at 35 degree C. The reaction was initiated by the addition of 25 μl of sample/blank. The mixture was incubated at 35° C. for 5 min with shaking. Using a spectrophotometer, the formation of PNP was measured continually at 410 nm. The blank run contains all the components with buffer instead of sample. One unit of lipase activity was defined as the amount of enzyme releasing 1 μl of free caprylic acid per minute at 35° C.

Determination of Molecule Weight and Purity.

SDS-PAGE was carried out on a 4-12% Nu-PAGE gel (+DTT) and Coomassie stained according to the manufacturers instructions (Novex, USA). The standard marker was See Blue Plus2 and was obtained from Novex, USA.

Results

Figure 1:
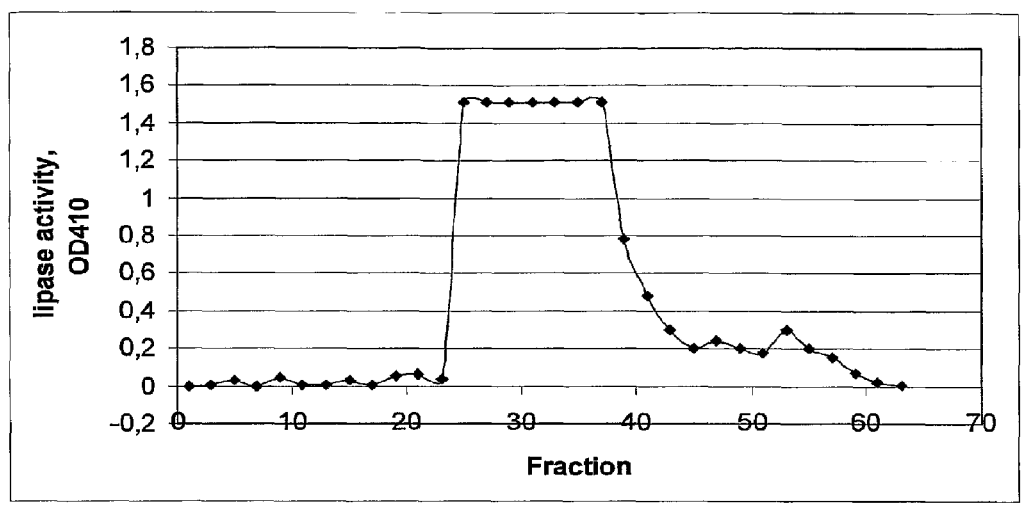
FIG. 1 shows the profile of the lipid acyltransferase activity (PNP-caprylate assay) obtained after anion exchange chromatography (IEC)

The chromatogram from Ion Exchange Chromatography (IEC) purification of the lipid acyltransferase mutant N80D is shown in FIG. 1. The fractions collected were analyzed for lipase activity (based on PNP-Caprylate assay). The activity of the fractions is illustrated in FIG. 1-a.

The fractions containing lipid acyltransferase activity (27-39, 195 ml) were pooled. The final recovery of the partly purified lipid acyltransferase was approx. 80% (based on pNP-Caprylate assay).

Fractions of the purified lipid acyltransferase were subjected to SDS-PAGE gel electrophoresis.

Figure 2:
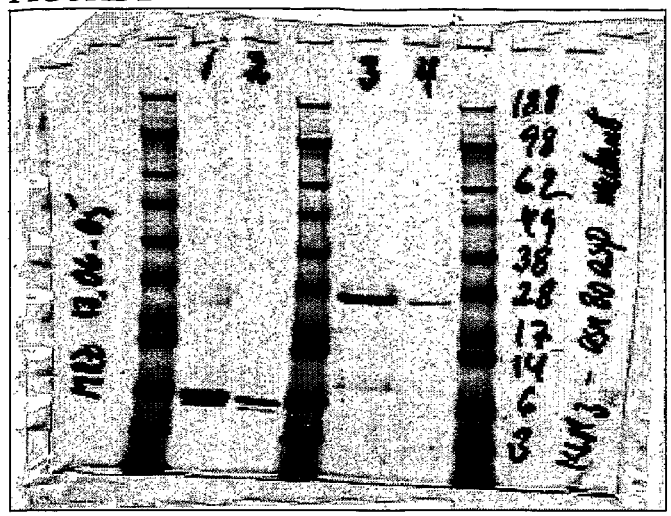
FIG. 2 shows the results of SDS-PAGE analyses of purified the lipid acyltransferase fractions (4-12% Mes, +DTT, 40/10 μl sample was applied to the gel)

The SDS-PAGE gel revealed lipid acyltransferase protein with a molecular weight of approx. 28 KDa. The partly purified lipid acyltransferase contained a minor impurity at approx 10 KDa (see FIG. 2).

The lipid acyltransferase pool 27-39 after IEC was analysed for phospholipase activity with the result of 20.4 PLU-7/ml.

The overall purification scheme is presented in Table 1, in which the lipid acyltransferase was partly purified with a recovery of 80%.

TABLE 1

| Purification of the lipid acyltransferase | | | | | |
|---|---|---|---|---|---|
| Sample | Vol. | $V_{Max}$ | Dilution | Tot. Units | % Recovery |
| Crude (Q3 + Q4) | 510 | 1.150 | 100 | 58650 | 100 |
| Desalted crude | 815 | 0.697 | 100 | 56806 | 97 |
| Pool 27-39, Q-Sep. | 195 | 1.203 | 200 | 46898 | 80 |

Example 2

Degumming Experiment

The lipid acyltransferase sample from Example 1 was used for degumming studies in the formulations shown in Table 2.

Plant sterol, alpha-tocopherol and phosphatidylcholine were dissolved in soya bean oil by heating the oil to 90° C. The oil was then cooled to approx 40° C. and the enzyme was added. The sample was placed at 40° C. for 17 hours during agitation and then a sample was taken out for HPTLC analysis by dissolving the sample in Chloroform:Methanol 2:1.

TABLE 2

Soya bean oil models with alpha-tocopherol and plant sterol, used for testing of the lipid acyltransferase.

| | | 1 | 2 | 3 | 4 | 5 | 6 | 7 | 8 | 9 | 10 |
|---|---|---|---|---|---|---|---|---|---|---|---|
| Soya bean oil | % | 98 | 97 | 97 | 96 | 97 | 96 | 96 | 95 | 96 | 92 |
| Alpha-tocopherol | % | | | | | 1 | 1 | 1 | 1 | 1 | 1 |
| Plant Sterol | % | | | 1 | 1 | | | 1 | 1 | 1 | 1 |
| Phosphatidylcholine | % | 2 | 2 | 2 | 2 | 2 | 2 | 2 | 2 | 2 | 2 |
| lipid acyltransferase pool 27-39 | % | | 1 | | 1 | | 1 | | 1 | | 4 |

The results from the HPTLC analysis are shown in FIG. 3 and FIG. 4.

The TLC results shown in FIG. 3 clearly show that phosphatidylcholine is almost 100% removed by adding the lipid acyltransferase to the oil. Only sample no. 10 contains small amount of phosphatidylcholine. Sample no. 10 has the highest amount of water, which indicates that for degumming the enzyme may work better in low water formulations, or it could be explained by the fact that because sample no. 10 contain 5% water a two-phase system is formed, which might cause less contact between the reactants and the enzyme.

From the results shown in FIG. 4 is was observed that small amount of fatty acids are formed, but when sterol or alpha-tocopherol is also available in the oil the amount of free fatty acids is lower, because the fatty acids from phosphatidylcholine it transferred to the sterol or tocopherol to form sterol-esters and tocopherol-esters.

The formation of sterol esters is clearly seen from the TLC results shown in FIG. 5. It should be noted that the reference material used, cholesterol ester, has the same retention time as plant-sterol-esters.

Example 3

Degumming Experiment (2)

In another experiment the lipid acyltransferase pool 27-39 from IEC chromatography, was tested at different enzyme dosages and water concentrations in soya bean oil with phosphatidylcholine and plant sterol. In this experiment a commercial phospholipase Lecitase Ultra™ was also tested in a concentration recommended by the supplier for degumming. The composition of the samples for this experiment are shown in Table 3.

TABLE 3

Soya bean oil model with plant sterol used for testing of the lipid acyltransferase, and Lecitase Ultra ™.

|  |  | 1 | 2 | 3 | 4 | 5 | 6 | 7 | 8 | 9 | 10 |
|---|---|---|---|---|---|---|---|---|---|---|---|
| Soya bean oil | % | 96.6 | 96.6 | 96 | 92 | 96 | 92 | 95 | 92 | 96 | 92 |
| Plant Sterol | % | 1 | 1 | 1 | 1 | 1 | 1 | 1 | 1 | 1 | 1 |
| Phosphatidylcholine | % | 2 | 2 | 2 | 2 | 2 | 2 | 2 | 2 | 2 | 2 |
| Lipid acyltransferase pool 27-39 | % |  | 0.4 | 0.4 | 0.4 | 1 | 1 | 2 | 2 |  |  |
| Lecitase Ultra ™, 1% solution | % |  |  |  |  |  |  |  |  | 0.3 | 0.3 |
| Water |  | 0.4 |  | 0.6 | 4.6 | 0 | 4 | 0 | 3 | 0.7 | 4.7 |
| Units/g oil (PLU-7/g) |  | 0 | 0.08 | 0.08 | 0.08 | 0.2 | 0.2 | 0.4 | 0.4 | 1.03 | 1.03 |

Plant sterol and phosphatidylcholine were dissolved in soya bean oil by heating to 95° C. during agitation. The oil was then cooled to 40° C. and the enzymes were added. The sample was maintained at 40° C. with magnetic stirring and samples were taken out after 4 and 20 hours and analysed by TLC. The results from the HPTLC analysis of samples taken out after 4 and 20 hours are shown in FIGS. 6 to 9.

The HPTLC results indicate that the lowest dosage of the lipid acyltransferase (0.4% corresponding to 0.08 PLU-7/g oil) is sufficient to remove phosphatidylcholine in soya bean oil after 20 h reaction time. It is also observed that the highest dosage of water (5%) seems to have a detrimental effect on the lipid acyltransferase for the hydrolysis of phosphatidylcholine in the oil. It is therefore expected that the lower degree of hydrolysis in the sample with highest dosage of the lipid acyltransferase conversion is explained by that fact that more water is also added to the sample. Contrary to this it is observed that Lecitase Ultra™ has a lower degree of hydrolysis of phosphatidylcholine in the lowest dosage of water (1%), whereas Lecitase Ultra™ almost completely removes phosphatidylcholine in the sample with 5% water.

The results from FIG. 7 also indicate that the main part of the plant sterol is converted to plant sterol ester in samples treated with the lipid acyltransferase whereas no sterol esters are formed in the samples treated with Lecitase Ultra™. FIG. 7 indicates that Lecitase Ultra™ produce more free fatty acids (FFA) than the lipid acyltransferase.

Conclusion

Degumming experiments with a model soya bean oil containing phosphatidylcholine, plant sterol and tocopherol has shown that a partially purified lipid acyltransferase enzyme is able to remove all phosphatidylcholine concomitant with the formation of plant sterol esters, and only to a small extent free fatty acids are formed.

One further advantage of the lipid acyltransferase is the formation of sterol esters, and in particular tocopherol ester, because sterols esters (including tocopherol ester) provide beneficial health properties. In conventional edible oil processing, following degumming the aqueous phase containing the hydrolysed polar lipid (e.g. phospholipid and/or glycolipid) is separated from the oil. Conventionally sterols are removed from the edible oil during the oil refining process (this is sometimes referred to as deodorising). However, the sterol esters (and tocopherol ester) resist deodorisation and thus remain in the oil. Accumulation of sterol esters in the oil is attractive because it has been shown that higher intake of plant sterol esters reduces the risk for cardiovascular diseases in humans.

The experiment also indicates that the lipid acyltransferase is able to make tocopherol esters, which will also accumulate in the oil.

This will contribute to improved oxidative stability of the oil and thus is a further benefit to using the lipid acyltransferase in accordance with the present invention for degumming Example 4

Degumming Experiment in Crude Oil

In another experiment, the lipid acyltransferase pool 27-39 from IEC chromatography was tested at different enzyme dosages and water concentrations in crude soya oil (before degumming) obtained from The Solae Company, Aarhus, Denmark. In this experiment, a commercial phospholipase Lecitase Ultra™ was also tested in a concentration recommended for degumming by the supplier. The composition of the samples for this experiment is shown in Table 4.

The samples were placed in a heating block at 40° C. during agitation with a magnetic stirrer. Samples were taken out after 20 hours for analysis.

TABLE 4

|  |  | 1 | 2 | 3 | 4 | 5 | 6 | 7 | 8 | 9 | 10 |
|---|---|---|---|---|---|---|---|---|---|---|---|
| Crude soya oil | % | 99.5 | 99.5 | 99 | 98 | 97 | 98 | 95 | 99.7 | 99 | 95 |
| Lipid Acyltransferase | % |  | 0.5 | 1 | 1 | 1 | 2 | 5 |  |  |  |
| Lecitase Ultra ™ #3108, 1% solution | % |  |  |  |  |  |  |  | 0.3 | 0.3 | 0.3 |
| Water | % | 0.5 | 0 | 0 | 1 | 2 | 0 | 0 | 0 | 0.7 | 4.7 |

The oil samples were analysed by HPTLC with the results shown in FIGS. 26 and 27.

The TLC analysis in FIG. 26 indicate that the lipid acyltransferase efficiently removes the phospholipids in crude soya oil without leaving any lysolecithin in the sample (sample 3, 4, 6 and 7). Lecitase Ultra™ also removes the phospholipid (PC), but some bands are remaining in the chromatogram, which is expected to be lysolecithin. It is also observed that lipid acyltransferase works in very low water environment, but Lecitase Ultra™ needs 1% to 5% water to work.

The results in FIG. 27 confirm that lipid acyl transferase converts the free sterol to sterolesters and Lecitase Ultra™ has no effect on sterols. FIG. 27 also indicates that some free fatty acids are formed both in samples with lipid acyl transferase and Lecitase Ultra™. The reason for the free fatty acid formation with lipid acyl transferase is explained by the fact that there is not enough acyl-donor (sterol) available, and therefore some hydrolysis also occurs.

Sample 1, 2, 3, 6, 8 and 10 from table 4 were analysed by GLC and the amount of sterol and sterol esters were quantified. The results are shown in Table 5.

TABLE 5

GLC analysis of sterol and sterol esters
In crude soya oil treated with enzyme (Table 4)

| Sample no | Enzyme | Sterol % | Sterolester % |
|---|---|---|---|
| 1 | Control | 0.25 | 0.07 |
| 2 | 0.5% Lipid acyltransferase pool 27-39 | 0.13 | 0.13 |
| 3 | 1% Lipid acyltransferase pool 27-39 | 0 | 0.26 |
| 6 | 2% Lipid acyltransferase pool 27-39 | 0 | 0.22 |
| 8 | 0.3% Lecitase Ultra ™ 1% solution | 0.25 | 0.03 |
| 10 | 0.3% Lecitase Ultra ™ 1% solution + 5% water | 0.27 | 0.05 |

The results in Table 5 confirm the ability of the lipid acyl transferase of the present invention to convert all sterol in crude soya oil to sterol ester, and a commercial phospholipase Lecitase Ultra™ showed no effect on sterol.

Conclusion

The effect of the lipid acyl transferase of the present invention on crude soya oil confirms that the lipid acyl transferase of the present invention effectively removes phospholipids in the crude soya oil concomitant with the formation of sterol esters.

Example 5

In another experiment, phospholipase from *Streptomyces thermosacchari* L131 was tested in crude soya oil.

The results confirm that phospholipase *Streptomyces thermosacchari* L131 effectively hydrolyses phospholipids in crude soya oil and is a suitable alternative enzyme for degumming of plant oils.

Enzymatic degumming processes of plant oils including soya oil and rape seed oil are currently expanding because this process is a less expensive and better process to remove lecithins from plant oils. The enzyme commercially used for oil degumming is a microbial phospholipase A1 or an animal derived phospholipase A2.

A (phospho)lipid acyl transferase *Streptomyces thermosacchari* L131 is another enzyme, which can be used for degumming.

Introduction

The purpose of this study was to investigate the possible use of a lipid acyltransferase from *Streptomyces thermosacchari* L131 for degumming of vegetable oil like soya oil, sunflower oil, and rape seed oil.

Traditionally, two processes have been used for degumming of oils, namely the physical degumming and the chemical degumming. Back in the 1990's, the enzymatic degumming process was developed, based on the use of pancreatic phospholipase. Because this enzyme was non-kosher, the phospholipase was substituted by microbial phospholipase A1. The enzymatic process has several advantages over the chemical or the physical degumming processes including cost savings, higher yield, and a more environmentally desirable process.

The purpose of this study was to investigate whether lipid acyltransferase from *Streptomyces thermosacchari* L131 would be a suitable enzyme for degumming. From the studies described above *Streptomyces thermosacchari* L131 is known to have hydrolytic properties against galactolipids and phospholipids without showing any activity on triglycerides, and it is expected that this enzyme also facilitates transferase reactions in certain environments with low water content. This study was conducted in crude soya oil with the natural content of phospholipids.

Materials and Methods

Enzyme

K371(jour 2390-30): *Streptomyces thermosacchari* L131/*S. lividans* freeze dried on starch.
(Activity: 108 PLU-7/g).
Lecitase Ultra (#3108) from Novozymes, Denmark
Cholesterolester, Fluka 26950
Plant Sterol Generol 122 N from Henkel, Germany
Crude soya oil from The Solae Company, Aarhus Denmark
Lecithin: L-α Phosphatidylcholine 95% Plant (Avanti #441601)

Phospholipase Activity

Substrate:
0.6% L-α Phosphatidylcholine 95% Plant (Avanti #441601), 0.4% Triton-X 100 (Sigma X-100), and 5 mM $CaCl_2$ were dissolved in 0.05M HEPES buffer pH 7.

Assay Procedure:
400 μl substrate was added to a 1.5 ml Eppendorf tube and placed in an Eppendorf Thermomixer at 37° C. for 5 minutes. At time T=0 min, 500 enzyme solution was added. Also a blank with water instead of enzyme was analyzed. The sample was mixed at 10*100 rpm in an Eppendorf Thermomixer at 37° C. for 10 minutes. At time T-10 min the reaction was stopped by placing the Eppendorf tube in another thermomixer at 99° C. for 10 minutes.

The free fatty acid content of samples was analyzed by using the NEFA C kit from WAKO GmbH.

Enzyme activity PLU-NEFA pH 7 was calculated as micromole fatty acid produced per minute under assay conditions.

GLC (Gas Chromatography)

Perkin Elmer 8420 Capillary Gas Chromatography equipped with WCOT fused silica column 12.5 m×0.25 mm ID×0.1 μm 5% phenyl-methyl-silicone (CP Sil 8 CB from Crompack).
Carrier: Helium.
Injection: 1.5 μL with split.
Detector: FID. 385° C.

| Oven program: | 1 | 2 | 3 | 4 |
|---|---|---|---|---|
| Oven temperature [° C.] | 80 | 200 | 240 | 360 |
| Isothermal, time [min] | 2 | 0 | 0 | 10 |
| Temperature rate [° C./min] | 20 | 10 | 12 | |

Sample preparation: Lipid extracted from 0.2 gram sample was dissolved in 2 mL heptane:pyridine 2:1 containing an internal standard heptadecane, 2 mg/mL. 500 μL of the sample was transferred to a crimp vial. 100 μl MSTFA (N-Methyl-N-trimethylsilyl-trifluoracetamid) was added and the reaction incubated for 15 minutes at 90° C.

HPTLC
Applicator: Automatic TLC Sampler 4, CAMAG
HPTLC plate: 20×10 cm, Merck no. 1.05641. Activated 30 minutes at 160° C. before use.
Application: 1 μl of a 8% solution of oil in buffer was applied to the HPTLC plate using Automatic TLC applicator.
Running buffer 4: Chloroform:Methanol:Water 75:25:4
Running buffer 5: P-ether:Methyl-tert-butyl-ether:Acetic acid 70:30:1
Application/Elution Time:
Running buffer 4: 20 min
Running buffer 5: 10 min
Development
The plate was dried in an oven for 10 minutes at 160° C., cooled, and dipped into 6% cupri acetate in 16% $H_3PO_4$. Dried additionally 10 minutes at 160° C. and evaluated directly.
Results.
Degumming Experiment.
*Streptomyces thermosacchari* L131 was used for degumming studies in the formulations shown in table 6.

The samples were placed at 40° C. for 18 hours with agitation, after which time a sample was collected for HPTLC analysis by dissolving the sample in Chloroform:Methanol 2:1

TABLE 6

Degumming of crude soya oil with *Streptomyces thermosacchari* L131 And Lecitase Ultra

|  |  | 1 | 2 | 3 | 4 | 5 | 6 |
|---|---|---|---|---|---|---|---|
| Crude soya oil | % | 99 | 99 | 98 | 97 | 99.7 | 99 |
| K371, 10% in water | % |  | 1 | 2 | 3 |  |  |
| Lecitase Ultra ™ #3108, 1% in water | % |  |  |  |  | 0.3 | 0.3 |
| Water | % | 1 | 0 | 0 | 0 |  | 0.7 |

The results from the HPTLC analysis are shown in FIGS. 59 and 60.

FIG. 59 TLC (Solvent 4) of reaction products from enzyme treatment of crude soya oil samples according to table 6. As reference, phosphatidylcholine (PC) was also analysed. PE (phosphatydylethanolamine (PE) and lysophosphatidylcholine (LPC) are also indicated.

FIG. 60 TLC (Solvent 5) of reaction products from enzyme treatment of crude soya oil samples according to table 6. References Cholesterolester, monoglyceride, diglyceride, triglyceride and plant sterol. Free fatty acid (FFA) is also indicated The TLC results in FIG. 59 clearly show that phosphatidylcholine was completely removed by adding *Streptomyces thermosacchari* L131 to the oil. Only the lowest dosage (sample 2) did not completely hydrolyse the phospholipids. Lecitase Ultra™ also hydrolysed the phospholipids in the oil when 5% water was available (sample 6) but without adding extra water (sample 5) only part of the phospholipids were hydrolysed.

The results shown in FIG. 60 indicate that the hydrolysis of phospholipids is coincident with the formation of free fatty acid.

Conclusion.

The lipid acyltransferase from *Streptomyces thermosacchari* L131 effectively hydrolysis phospholipids in crude soya oil during formation of free fatty acids.

All publications mentioned in the above specification are herein incorporated by reference. Various modifications and variations of the described methods and system of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention will now be further described by the following numbered paragraphs:

1. A process of enzymatic degumming edible oils, comprising treating the edible oil with a lipid acyltransferase so as to transfer an acyl group from a major part of the phospholipid to one or more acyl acceptors, wherein the acyl acceptor is one or more of sterol and/or stanol and wherein the lipid acyltransferase is characterized in that:
   (a) the lipid acyltransferase possesses acyltransferase activity which is defined as ester transfer activity whereby the acyl part of an original ester bond of a lipid acyl donor is transferred to an acyl acceptor to form a new ester; and
   (b) the enzyme comprises the amino acid sequence motif GDSX, wherein X is one or more of the following amino acid residues L, A, V, I, F, Y, H, Q, T, N, M or S, and wherein when aligned to either the pfam 00657 consensus sequence and/or SEQ ID NO: 37 the lipid acyltransferase has a GANDY block.
2. A process according to paragraph 1 wherein a sterol ester and/or a stanol ester is formed.
3. A process according to paragraph 2 wherein the acyl acceptor is a sterol.
4. A process according to any one of the preceding paragraphs wherein the phospholipid is a lecithin.
5. A process according to any one of the preceding paragraphs wherein the lipid acyl transferase, as well as being able to transfer an acyl group from a lipid to a sterol and/or a stanol, additionally transfers the acyl group from a lipid to one or more of a carbohydrate, a protein, a protein subunit, and glycerol.
6. A process according to any one of the preceding paragraphs wherein the lipid acyltransferase is a natural lipid acyltransferase.
7. A process according to any one of the preceding paragraphs wherein the lipid acyltransferase is a variant lipid acyltransferase.
8. A process according to any one of the preceding paragraphs wherein said lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.
9. A process according to any one of the preceding paragraphs wherein said lipid acyltransferase is obtainable from one or more of *Aeromonas hydrophila, Aeromonas salmonicida, Streptomyces coelicolor, Streptomyces rimosus, Streptomyces thermosacchari, Streptomyces avermitilis, Mycobacterium, Streptococcus pyogenes, Lactococcus lactis, Streptococcus pyogenes, Streptococcus thermophilus, Lactobacillus helveticus, Desulfitobacterium dehalogenans, Bacillus* sp, *Campylobacter jejuni, Vibrionaceae, Xylella fastidiosa, Sulfolobus solfataricus, Saccharomyces* cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis, Thermobifida fusca and Corynebacterium efficiens.

10. A process according to any of the preceding paragraphs wherein the X of the GDSX motif is L.

11. A process according to any one of the preceding paragraphs wherein the lipid acyltransferase comprises one or more of the following amino acid sequences: SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, or SEQ ID No. 15, SEQ ID No. 16, SEQ ID No. 17, SEQ ID No. 18, SEQ ID No. 36, SEQ ID No. 38, SEQ ID No. 40, SEQ ID No. 41, SEQ ID No 45, SEQ ID No. 47, SEQ ID No. 50 or an amino acid sequence which has 75% or more identity thereto.

12. A process according to paragraph 11 wherein the lipid acyltransferase comprises one or more of the following amino acid sequences: SEQ ID No. 3, SEQ ID No. 4, SEQ ID No. 1 or SEQ ID No. 15, or an amino acid sequence which has 75% or more identity thereto.

13. A process according to paragraph 11 wherein the lipid acyltransferase comprises one or more of the following amino acid sequences: SEQ ID No. 36, SEQ ID No. 38, SEQ ID No. 40, SEQ ID No. 41, SEQ ID No 45, SEQ ID No. 47, SEQ ID No. 50, or an amino acid sequence with at least 70% identity thereto.

14. A process according to paragraph 11 wherein the lipid acyltransferase comprises one or more of SEQ ID No. 17 or SEQ ID No. 18, or an amino acid sequence with 70% or more homology thereto.

15. A process according to paragraph 11 wherein the lipid acyltransferase comprises the amino acid sequence shown as SEQ ID No. 16, or an amino acid sequence which has 75% or more homology thereto.

16. A process according to paragraph 11 wherein the lipid acyltransferase comprises the amino acid sequence shown as SEQ ID No. 16.

17. A process according to paragraph 7 wherein the lipid acyltransferase is characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7.

18. A process according to paragraph 17 wherein the lipid acyltransferase comprises an amino acid sequence shown as SEQ ID No. 34, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 31, SEQ ID No. 32, or SEQ ID No. 33 except for one or more amino acid modifications at any one or more of the amino acid residues defined in set 2 or set 4 or set 6 or set 7 identified by sequence alignment with SEQ ID No. 34.

19. A process according to paragraph 18 wherein the lipid acyltransferase comprises the sequence shown as SEQ ID No. 34 or SEQ ID No. 35 except for one or more amino acid modifications at any one or more of the amino acid residues defined in set 2 or set 4 or set 6 or set 7.

20. A process according to any one of paragraphs 7, 17 or 18 wherein the lipid acyltransferase comprises the amino acid sequence shown as SEQ ID No. 16 or an amino acid sequence with 75% or more homology thereto.

21. A process according to any one of paragraphs 7, 17 or 18 wherein the lipid acyltransferase comprises the amino acid sequence shown as SEQ ID No. 16.

22. A process according to any one of the preceding paragraphs wherein there is less than 1% water in the edible oil during treatment.

23. A process according to paragraph 22 wherein there is less than 0.5% water.

24. A process according to paragraph 22 wherein there is less than 0.1% water.

25. A process according to any one of the preceding paragraphs wherein the process comprises removing the lysophospholipids produced by the action of the lipid acyltransferase by filtration.

26. Use of a lipid acyltransferase characterized in that:
   (a) the lipid acyltransferase possesses acyltransferase activity which is defined as ester transfer activity whereby the acyl part of an original ester bond of a lipid acyl donor is transferred to an acyl acceptor to form a new ester; and
   (b) the enzyme comprises the amino acid sequence motif GDSX, wherein X is one or more of the following amino acid residues L, A, V, I, F, Y, H, Q, T, N, M or S, and wherein when aligned to either the pfam 00657 consensus sequence and/or SEQ ID NO: 37 the lipid acyltransferase has a GANDY block in the degumming of edible oils to remove phospholipids and to increase the formation of sterol esters and/or stanol esters in the oil.

27. Use according to paragraph 26 where there is no significant increase in the free fatty acids in the oil following treatment.

28. Use according to paragraph 26 or paragraph 27 wherein the phospholipid is a lecithin.

29. Use according to any one of paragraphs 26-28 wherein the lipid acyltransferase is a natural lipid acyltransferase.

30. Use according to any one of paragraphs 26-29 wherein the lipid acyltransferase is a variant lipid acyltransferase.

31. Use according to any one of paragraphs 26-30 wherein said lipid acyltransferase is obtainable from organisms from one or more of the following genera: Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida and Corynebacterium.

32. Use according to any one of paragraphs 26-31 wherein the lipid acyltransferase is obtainable from one or more of Aeromonas hydrophila, Aeromonas salmonicida, Streptomyces coelicolor, Streptomyces rimosus, Streptomyces thermosacchari, Streptomyces avermitilis, Mycobacterium, Streptococcus pyogenes, Lactococcus lactis, Streptococcus pyogenes, Streptococcus thermophilus, Lactobacillus helveticus, Desulfitobacterium dehalogenans, Bacillus sp, Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis Candida parapsilosis, Thermobifida fusca and Corynebacterium efficiens.

33. Use according to any one of paragraphs 26-32 wherein the X of the GDSX motif is L.
34. Use according to any one of paragraphs 26-33 wherein the lipid acyltransferase comprises one or more of the following amino acid sequences: SEQ ID No. 1, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, or SEQ ID No. 15, SEQ ID No. 16, SEQ ID No. 17, SEQ ID No. 18, SEQ ID No. 36, SEQ ID No. 38, SEQ ID No. 40, SEQ ID No. 41, SEQ ID No 45, SEQ ID No. 47, SEQ ID No. 50 or an amino acid sequence which has 75% or more identity thereto.
35. Use according to paragraph 34 wherein the lipid acyltransferase comprises one or more of the following amino acid sequences: SEQ ID No. 3, SEQ ID No. 4, SEQ ID No. 1 or SEQ ID No. 15 or SEQ ID No. 15, or an amino acid sequence which has 75% or more identity thereto.
36. Use according to paragraph 34 wherein the lipid acyltransferase comprises one or more of the following amino acid sequences: SEQ ID No. 36, SEQ ID No. 38, SEQ ID No. 40, SEQ ID No. 41, SEQ ID No 45, SEQ ID No. 47, SEQ ID No. 50, or an amino acid sequence with at least 70% identity thereto.
37. Use according to paragraph 34 wherein the lipid acyltransferase comprises one or more of SEQ ID No. 17 or SEQ ID No. 18, or an amino acid sequence with 70% or more homology thereto.
38. Use according to paragraph 34 wherein the lipid acyltransferase comprises the amino acid sequence shown as SEQ ID No. 16, or an amino acid sequence which has 75% or more homology thereto.
39. Use according to paragraph 34 wherein the lipid acyltransferase comprises the amino acid sequence shown as SEQ ID No. 16.
40. Use according to paragraph 30 wherein the lipid acyltransferase is characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7.
41. Use according to paragraph 40 wherein the lipid acyltransferase comprises an amino acid sequence shown as SEQ ID No. 34, SEQ ID No. 35, SEQ ID No. 3, SEQ ID No. 4, SEQ ID No. 5, SEQ ID No. 6, SEQ ID No. 7, SEQ ID No. 8, SEQ ID No. 19, SEQ ID No. 10, SEQ ID No. 11, SEQ ID No. 12, SEQ ID No. 13, SEQ ID No. 14, SEQ ID No. 1, SEQ ID No. 15, SEQ ID No. 25, SEQ ID No. 26, SEQ ID No. 27, SEQ ID No. 28, SEQ ID No. 29, SEQ ID No. 30, SEQ ID No. 31, SEQ ID No. 32, or SEQ ID No. 33 except for one or more amino acid modifications at any one or more of the amino acid residues defined in set 2 or set 4 or set 6 or set 7 identified by sequence alignment with SEQ ID No. 34.
42. Use according to paragraph 41 wherein the lipid acyltransferase comprises the sequence shown as SEQ ID No. 34 or SEQ ID No. 35 except for one or more amino acid modifications at any one or more of the amino acid residues defined in set 2 or set 4 or set 6 or set 7.
43. Use according to paragraph 30 wherein the lipid acyltransferase comprises the amino acid sequence shown as SEQ ID No. 16 or an amino acid sequence with 75% or more homology thereto.
44. Use according to paragraph 43 wherein the lipid acyltransferase comprises the amino acid sequence shown as SEQ ID No. 16.
45. Use according to any one of paragraphs 26 to 44 wherein there is less than 1% water in the edible oil during treatment.
46. Use according to paragraph 45 wherein there is less than 0.5% water.
47. Use according to paragraph 46 wherein there is less than 0.1% water.
48. A method as hereinbefore described with reference to the accompanying description and the figures.
49. A use as hereinbefore described with reference to the accompanying description and figures.

The invention claimed is:

1. A method comprising:
   enzymatically degumming an edible oil comprising:
   providing one or more lipid acyltransferases to the edible oil;
   transferring an acyl group from a phospholipid to one or more acyl acceptors selected from sterol and stanol to form one or more esters;
   wherein the one or more lipid acyltransferases have at least 5% acyltransferase activity, wherein:
   an edible oil to which no enzyme has been added is a control;
   (ii) in an enzymatic reaction with an edible oil, lipid material from the reaction and control are analyzed;
   (iii) acyltransferase activity is calculated as a percentage of total enzymatic activity using the formula:

$$(A \times 100)/((A + \Delta\% \text{ fatty acid})/\text{Mv fatty acid}),$$

wherein:
   $\Delta\%$ fatty acid=% fatty acid(enzyme)−% fatty acid(control);

Mv fatty acid=average molecular weight of the fatty acids; and

A=Δ% sterol ester/Mv sterol ester, wherein:

Δ% sterol ester=% sterol/stanol ester(enzyme)−% sterol/stanol ester(control); and Mv sterol ester=average molecular weight of the sterol/stanol esters.

2. The method of claim 1 wherein a sterol ester and/or a stanol ester is formed.

3. The method of claim 2 wherein the acyl acceptor is a sterol.

4. The method of claim 1 wherein the phospholipid is a lecithin.

5. The method of claim 1 wherein the lipid acyl transferase, as well as being able to transfer an acyl group from a lipid to a sterol and/or a stanol, additionally transfers the acyl group from a lipid to one or more of a carbohydrate, a protein, a protein subunit, and glycerol.

6. The method of claim 1 wherein the lipid acyltransferase is a natural lipid acyltransferase.

7. The method of claim 1 wherein the lipid acyltransferase is a variant lipid acyltransferase.

8. The method of claim 1 wherein said lipid acyltransferase is obtainable from an organism from one or more of the following genera: *Aeromonas, Streptomyces, Saccharomyces, Lactococcus, Mycobacterium, Streptococcus, Lactobacillus, Desulfitobacterium, Bacillus, Campylobacter, Vibrionaceae, Xylella, Sulfolobus, Aspergillus, Schizosaccharomyces, Listeria, Neisseria, Mesorhizobium, Ralstonia, Xanthomonas, Candida, Thermobifida* and *Corynebacterium*.

9. The method of claim 1 wherein said lipid acyltransferase is obtainable from one or more of *Aeromonas hydrophila, Aeromonas salmonicida, Streptomyces coelicolor, Streptomyces rimosus, Streptomyces thermosacchari, Streptomyces avermitilis, Mycobacterium, Streptococcus pyogenes, Lactococcus lactis, Streptococcus pyogenes, Streptococcus thermophilus, Lactobacillus helveticus, Desulfitobacterium dehalogenans, Bacillus sp, Campylobacter jejuni, Vibrionaceae, Xylella fastidiosa, Sulfolobus solfataricus, Saccharomyces cerevisiae, Aspergillus terreus, Schizosaccharomyces pombe, Listeria innocua, Listeria monocytogenes, Neisseria meningitidis, Mesorhizobium loti, Ralstonia solanacearum, Xanthomonas campestris, Xanthomonas axonopodis, Candida parapsilosis, Thermobifida fusca* and *Coynebacterium efficiens*.

10. The method of claim 1 wherein the lipid acyltransferase comprises a GDSX motif.

11. The method of claim 10 wherein X of the GDSX motif is L.

12. The method of claim 1 wherein the lipid acyltransferase comprises an amino acid sequence shown as SEQ ID NO: 16 or an amino acid sequence which has 75% or more identity thereto.

13. The method of claim 12 wherein the lipid acyltransferase comprises the amino acid sequence shown as SEQ ID NO: 16.

14. Previously presented) The method of claim 7 wherein the lipid acyltransferase is characterised in that the enzyme comprises the amino acid sequence motif GDSX, wherein X is one or more of the following amino acid residues L, A, V, I, F, Y, H, Q, T, N, M or S, and wherein the variant enzyme comprises one or more amino acid modifications compared with a parent sequence at any one or more of the amino acid residues defined in set 2 or set 4 or set 6 or set 7.

15. The method of claim 7 wherein the lipid acyltransferase comprises the amino acid sequence shown as SEQ ID NO: 16 or an amino acid sequence with 75% or more homology thereto.

16. The method of claim 7 wherein the lipid acyltransferase comprises the amino acid sequence shown as SEQ ID NO: 16.

17. The method of claim 1 wherein there is less than 1% water in the edible oil during treatments.

18. The method of claim 17 wherein there is less than 0.5% water.

19. The method of claim 18 wherein there is less than 0.1% water.

20. The method of claim 1 wherein the process comprises removing the lysophospholipids produced by the action of the lipid acyltransferase by filtration.

* * * * *